US010500274B2

(12) United States Patent
Olson et al.

(10) Patent No.: US 10,500,274 B2
(45) Date of Patent: Dec. 10, 2019

(54) METHODS FOR REDUCING VIRAL LOAD IN HIV-1 INFECTED PATIENTS

(71) Applicant: CytoDyn Inc., Lake Oswego, OR (US)

(72) Inventors: William C. Olson, Yorktown Heights, NY (US); Paul J. Maddon, Scarsdale, NY (US); Daniel C. Pevear, Medford, MA (US); Robert J. Israel, Suffern, NY (US); Jose D. Murga, Rosedale, NY (US)

(73) Assignee: CytoDyn Inc., Vancouver, WA (US)

( * ) Notice: Subject to any disclaimer, the term of this patent is extended or adjusted under 35 U.S.C. 154(b) by 0 days.

(21) Appl. No.: 13/621,590

(22) Filed: Sep. 17, 2012

(65) Prior Publication Data

US 2013/0216526 A1    Aug. 22, 2013

Related U.S. Application Data

(63) Continuation of application No. 12/590,005, filed on Oct. 30, 2009, now abandoned, and a continuation-in-part of application No. PCT/US2008/005564, filed on Apr. 30, 2008.

(60) Provisional application No. 61/211,488, filed on Mar. 31, 2009, provisional application No. 61/206,850, filed on Feb. 4, 2009.

(51) Int. Cl.
*C07K 16/28* (2006.01)
*A61K 39/395* (2006.01)
*A61K 39/00* (2006.01)

(52) U.S. Cl.
CPC .... *A61K 39/3955* (2013.01); *A61K 39/39541* (2013.01); *C07K 16/2812* (2013.01); *C07K 16/2866* (2013.01); *A61K 39/001121* (2018.08)

(58) Field of Classification Search
CPC .................. C07K 16/2866; A61K 39/001121
See application file for complete search history.

(56) References Cited

U.S. PATENT DOCUMENTS

| 7,122,185 | B2* | 10/2006 | Olson ................ C07K 16/2866 424/143.1 |
| 7,666,419 | B2* | 2/2010 | Olson ................ C07K 16/2866 424/143.1 |
| 7,851,600 | B2* | 12/2010 | Olson ................ C07K 16/2866 424/143.1 |
| 8,821,877 | B2* | 9/2014 | Olson .............. A61K 39/39541 424/156.1 |
| 2003/0228306 | A1 | 12/2003 | Olson et al. |
| 2006/0154857 | A1 | 7/2006 | Redfield et al. |
| 2007/0026441 | A1* | 2/2007 | Olson .............. A61K 39/39541 435/5 |
| 2007/0031408 | A1 | 2/2007 | Olson et al. |
| 2013/0216526 | A1 | 8/2013 | Olson et al. |

OTHER PUBLICATIONS

Murga, J. D., et al., 2006, Potent antiviral synergy between monoclonal antibody and small-molecule CCR5 inhibitors of human immunodeficiency virus type 1, Antimicrob. Agents Chemother. 50(10):3289-3296.*

Lundin, J., et al., 2002, Phase II trial of subcutaneous anti-CD52 monoclonal antibody alemtuzumab (Campath-1H) as first-line treatment for patients with B-cell chronic lymphocytic leukemia (B-CLL), Blood 100:768-773.*

Hanauer, S. B., et al., 2006, Human Anti-Tumor Necrosis Factor Monoclonal Antibody (Adalimumab) in Crohn's Disease: the CLASSIC—I Trial, Gastroenterol. 130:323-333.*

Murga, J. D., et al., Oct. 2006, Potent Antiviral Synergy between Monoclonal Antibody and Small-Molecule CCR5 Inhibitors of Human Immunodeficiency Virus Type 1, Antimicrob. Agents Chemother. 50(10):3289-3296.*

Bekker, P. J., et al., 2004, A single-dose placebo-controlled study of AMG 162, a fully human monoclonal antibody to RANKL, in postmenopausal women, J. Bone Mineral Res., 19(7):1059-1066.*

International Search Report issued by the International Searching Authority (ISA/US) in connection with International Application No. PCT/US2008/005564.

Written Opinion of the International Searching Authority issued by the International Searching Authority (ISA/US) in connection with International Application No. PCT/US2008/005564.

Nelson et al., Efficacy and Safety of Maraviroc plus Optimized Background Therapy in Viremic, ART-experienced Patients Infected with CCR5-tropic HIV-1 in Europe, Australia, and North America: 24-Week Results. Abstract 104aLB.14$^{th}$. Conference of Feb. 25-Feb. 28, 2008. Two pages (All). Annual Conference on Retroviruses and Opportunistic Infection, Los Angeles California. Accessed electronically, Oct. 30, 2009 at http://www.retroconference.org/2007/Abstracts/30636.html.

Office Action dated Dec. 6, 2011 in connection with U.S. Appl. No. 12/590,005, filed Oct. 30, 2009.

Office Action dated Mar. 20, 2012 in connection with U.S. Appl. No. 12/590,005, filed Oct. 30, 2009.

Castor et al., "The role of chemokines in mediating graft versus host disease: opportunities for novel therapeutics," *Front. Pharm.* 3:1-13, 2012.

Gilliam et al., "Clinical use of CCR5 inhibitors in HIV and beyond," *J. Trans. Med.* 9(Suppl. 1):S9, 2010. (14 pages).

Reshef et al., "Blockade of Lymphocyte Chemotaxis in Visceral Graft-versus-Host Disease," *N. Engl. J. Med* 367:135-145, 2012.

Yuan et al., "Prophylaxis of acute graft-versus-host disease by CCR5 blockade combined with cyclosporine A in murine model," *Inflamm. Res.* 64:137-144, 2015.

Jacobson et al., "Anti-HIV-1 Activity of Weekly or Biweekly Treatment with Subcutaneous PRO 140, a CCR5 Monoclonal Antibody." Journal of Infectious Diseases, vol. 201, No. 10, May 15, 2010, pp. 1481-1487.

* cited by examiner

*Primary Examiner* — Jeffrey S Parkin
(74) *Attorney, Agent, or Firm* — Seed IP Law Group LLP

(57) ABSTRACT

This invention provides a method of reducing viral load in an HIV-1-infected human subject which comprises administering to the subject an effective HIV-1 viral load reducing dose of a CCR5 receptor antagonist, such as a humanized antibody designated PRO 140 or an anti-CCR5 receptor monoclonal antibody, wherein the viral load reducing dose achieves an average maximum decrease of viral load in the subject of at least 1.83 $\log_{10}$ to 2.5 $\log_{10}$ at about ten days following administration of the CCR5 receptor antagonist and wherein the viral load reducing dose further achieves a mean viral load reduction of 1.7 $\log_{10}$ at about nine days following administration of the CCR5 receptor antagonist.

12 Claims, 34 Drawing Sheets

Triangle = PRO140-treated
Square = Untreated

Scheme 1. The S$_N$2 Displacement Route

Figure 1. Structures of lead compounds (A, B) and design of anilide derivatives 1 with quarternary ammonium moiety.

Scheme 1ᵃ

ᵃ (a) (1) (COCl)₂, cat. DMF/CH₂Cl₂, (2) 5, NEt₃/THF or 5, HOBt, WSC, NEt₃/DMF; (b) MeI/DMF; (c) Ion-exchange resin (Cl⁻)/aq MeOH.

Scheme 2ᵃ

ᵃ (a) (1) (COCl)₂, cat. DMF/CH₂Cl₂, (2) 7, NEt₃/THF ; (b) HCl/acetone; (c) SOCl₂, pyridine/CHCl₃; (d) NR²R³R⁴/DMF.

PRO140-1101 CCR5 Lymphocyte Coating
5mg/kg cohort

FIGURE 18

|  | Placebo (n=9) | 0.5 mg/kg (n=10) | 2.0 mg/kg (n=10) | 5.0 mg/kg (n=10) |
|---|---|---|---|---|
| Mean maximum $\log_{10}$ change in HIV RNA | -0.39 | -0.58 (p=0.34) | -1.20 (p=0.0002) | -1.83 (p<0.0001) |
| Mean $\log_{10}$ change in HIV RNA 9 days post-treatment | -0.13 | -0.37 (p=0.26) | -1.04 (p=0.0001) | -1.70 (p<0.0001 |
| Number of patients With a ≥1.0 $\log_{10}$ Decrease in HIV RNA at any time | 0/9 | 1/10 (p=1.0) | 6/10 (p=0.011) | 10/10 (p<0.0001) |

A.

B.

METHODS FOR REDUCING VIRAL LOAD IN HIV-1 INFECTED PATIENTS

This application is a continuation of U.S. Ser. No. 12/590,005, filed Oct. 30, 2009, which claims the benefit of U.S. Provisional Application No. 61/211,488, filed Mar. 31, 2009; U.S. Provisional Application No. 61/206,850, filed Feb. 4, 2009; is a continuation-in-part of PCT International Application No. PCT/US2008/005564, filed Apr. 30, 2008; and claims the benefit of U.S. Provisional Applications Nos. 61/009,351, filed Dec. 28, 2007, 60/967,758, filed Sep. 7, 2007, 60/961,325, filed Jul. 19, 2007 and 60/927,021, filed Apr. 30, 2007, the contents of all of which are hereby incorporated by reference into this application.

This invention was made with support under United States Government Grant Nos. AIO46871 and AIO66329 from the National Institute of Allergy and Infectious Diseases. Accordingly, the United States Government has certain rights in the subject invention.

Throughout this application, various publications are referenced in parentheses by author name and date, or by a patent or patent publication number. Full citations for these publications may be found at the end of the specification immediately preceding the claims. The disclosures of each of these publications in its entirety are hereby incorporated by reference into this application in order to more fully describe the state of the art as known to those skilled therein as of the date of this application.

BACKGROUND OF THE INVENTION

Infection of cells by human immunodeficiency virus type I (HIV-1) is mediated by the viral envelope (Env) glycoproteins gp120 and gp41, which are expressed as a noncovalent, oligomeric complex on the surface of virus and virally infected cells. Entry of the virus into target cells proceeds through a cascade of events at the cell surface that include (1) binding of the viral surface glycoprotein gp120 to a cell surface receptor, (2) Env binding to fusion coreceptors, and (3) multiple conformational changes in gp41.

The first high-affinity interaction between the virion and the cell surface is the binding of gp120 to cell surface CD4, which is the primary receptor for HIV-1 (Dalgleish et al.; 1984; Klatzmann et al., 1984; Maddon et al., 1986; McDougal et al., 1986). This binding induces conformational changes in gp120, which enable it to interact with one of several chemokine receptors (Berger, 1997; Bieniasz et al., 1998; Dragic et al., 1997; Littman, 1998). The CC-chemokine receptor 5 (CCR5) is the major co-receptor for macrophage-tropic (R5) strains, and plays a crucial role in the transmission of HIV-1 (Berger, 1997; Bieniasz et al., 1998; Dragic et al., 1997; Littman, 1998). T cell line-tropic (X4) viruses use CXCR4 to enter target cells, and usually, but not always, emerge late in disease progression or as a consequence of virus propagation in tissue culture. Some primary HIV-1 isolates are dual-tropic (R5X4) since they can use both co-receptors, though not always with the same efficiency (Connor et al., 1997; Simmons et al., 1996). Binding of gp120 to a chemokine receptor in turn triggers conformational changes in the viral transmembrane glycoprotein gp41, which mediates fusion of the viral and cellular membranes.

Each stage of this multi-step process can be blocked with inhibitors of the appropriate viral or cellular protein, and the inhibitors of gp120, gp41, CD4 and coreceptor are collectively known as entry inhibitors. Entry inhibitors represent at least 4 distinct classes of agents based on their molecular targets and determinants of viral resistance (Olson and Maddon, 2003). Table 1 lists HIV-1 entry inhibitors known to be in clinical development or approved for clinical use.

PRO 542 is a tetravalent, third-generation CD4-IgG2 fusion protein comprising the DID2 domains of CD4 genetically fused to the heavy and light chain constant regions of human IgG2 (Allaway et al., 1995; Zhu et al., 2001). This agent binds the HIV-1 envelope glycoprotein gp120 with nanomolar affinity and may inhibit virus attachment both by receptor blockade and by detaching gp120 from the virion surface, thereby irreversibly inactivating the virus.

TABLE 1

HIV-1 entry inhibitors

| Compound | Molecular Class | Target | Stage of Entry | Developer |
| --- | --- | --- | --- | --- |
| PRO542 | CD4-Ig Fusion Protein | gp120 | Attachment | Progenics |
| BMS-488043 | Small Molecule | gp120 | Attachment | Bristol-Myers Squibb |
| TNX-355 | Humanized antibody | CD4 | Post-Attachment | Genentech (Tanox) |
| PRO 140 | Humanized antibody | CCR5 | Coreceptor | Progenics |
| CCR5mAb004 | Human antibody | CCR5 | Coreceptor | Human Genome Sciences |
| SCH-D (vicriviroc) | Small Molecule | CCR5 | Coreceptor | Schering-Plough |
| UK-427,857 (maraviroc) | Small Molecule | CCR5 | Coreceptor | Pfizer |
| GW873140 | Small Molecule | CCR5 | Coreceptor | GlaxoSmithKline |
| TAK-652 | Small Molecule | CCR5 | Coreceptor | Takeda |
| AMD070 | Small Molecule | CXCR4 | Coreceptor | AnorMed |
| T-20 (enfuvirtide) | Peptide | gp41 | gp41 Fusion | Trimeris/Roche |

BMS-488043 is an optimized analog of BMS-378806 (see PCT International Publication Nos. WO 01/62255 A1 and WO 03/082289 A1), which has been variously reported to block gp120 attachment to CD4 (Lin et al., 2002; 2003) and post-attachment events (Si et al., 2004).
TNX-355 is a humanized IgG4 version of the anti-CD4 monoclonal antibody (mAb) 5A8, which blocks fusion events that occur post-attachment of gp120 to CD4 (Burkly et al., 1992; Moore et al., 1992).
PRO 140, a humanized anti-CCR5 mAb, and the small-molecule CCR5 antagonists, SCH-D (also now designated SCH 417670 or vicriviroc), UK-427,857 (also designated maraviroc) and GW873140, are discussed below.
CCR5mAb004 is a fully human mAb, generated using the Abgenix XenoMouse ® technology, that specifically recognizes and binds to CCR5 (Roschke et al., 2004). CCR5mAb004 has been reported to inhibit CCR5-dependent entry of HIV-1 viruses into human cells, and recently entered Phase 1 clinical trials (HGS Press Release, 2005).

The first small-molecule anti-CCR5 antagonist identified as capable of inhibiting HIV-1 infection was TAK-779 (Baba et al., 1999). However, TAK-779 exhibited poor oral bioavailability (Baba et al., 2005) and local injection site irritation (Iizawa et al., 2003), and has been replaced in clinical development by a TAK-779 derivative, TAK-652 (Baba et al., 2005). TAK-652 is an orally bioavailable CCR5 antagonist with potent anti-HIV-1 activity in the nanomolar range in vitro and promising pharmacological profiles in vivo (Baba et al., 2005).

AMD070 is a second-generation CXCR4 inhibitor; the first-generation CXCR4 inhibitor AMD3100 did not demonstrate a favorable safety window for HIV-1 therapy (Schols et al., 2002).

Finally, T-20 was approved for salvage therapy of HIV-1 infection following favorable antiviral and safety profiles in each of two pivotal Phase 3 studies (Lalezari et al., 2003; Lazzarin et al., 2003).

CCR5 as a Target for Anti-HIV-1 Therapy

As first demonstrated in 1986, HIV-1 binds to target cells via the CD4 receptor but requires additional host cell factors to mediate entry (Maddon et al., 1986). Over the next decade, a number of candidate coreceptors were proposed, but none reproducibly mediated viral entry when coexpressed with CD4 in otherwise nonpermissive cells. However, in 1996, certain chemokine receptors, mainly CCR5 and CXCR4, were shown to serve as requisite fusion coreceptors for HIV-1.

Cocchi et al. (1995) provided the first link between HIV-1 and chemokines, which are small (~8 kDa) homologous soluble proteins. Chemokines mediate the recruitment and activation of immune cells. They are classified as CC-, CXC-, $CX_3C$- and XC-chemokines based on the number and sequential relationship of the first two of four conserved cysteine residues; most are either CC- or CXC-chemokines. The CC-chemokines RANTES, MIP-1α and MIP-1β, were shown to block replication of primary macrophage-tropic strains of HIV-1 (Cocchi et al., 1995). Using expression cloning techniques, Feng et al. (1996) discovered that the chemokine receptor fusin (later renamed CXCR4) was a fusion coreceptor for strains of HIV-1 adapted to growth on T cell lines. Shortly thereafter, several groups reported the cloning of CCR5, a CC chemokine receptor with specificity for RANTES, MIP-1α and MIP-1β (Combadiere et al., 1996; Raport et al., 1996; Samson et al., 1997), and others then demonstrated that CCR5 was the main entry cofactor used by primary macrophage-tropic HIV-L isolates (Alkhatib et al., 1996; Choe et al., 1996; Deng et al., 1996; Doranz et al., 1996; Dragic et al., 1996). The patterns of CCR5 and CXCR4 expression helped solve long-standing riddles concerning the tropism of different strains of HIV-1. Macrophage-tropic, T-cell-line-tropic and dual-tropic viruses could be more descriptively classified as being R5, X4 and R5X4 viruses based on their abilities to utilize CCR5, CXCR4 or both receptors, respectively, for entry.

A variety of other chemokine receptors can function as HIV-1 coreceptors when over-expressed in vitro. The list includes CCR8, Apj, V28, US28, CCR2b, CCR3, gpr1, Bonzo (STRL33, TYMSTR), and BOB (gpr15). Clearly, proteins belonging to the chemokine receptor family have biochemical properties that promote HIV-1 membrane fusion. However, most of the above-mentioned coreceptors are not very efficient, are not normally coexpressed with CD4, and function only with certain strains of HIV-1, HIV-2 or SIV. The in vive relevance of these alternative coreceptors has not been established.

Several factors make CCR5 an attractive target for new antiretroviral therapies. CCR5 plays a central role in HIV-1 transmission and pathogenesis, and naturally-occurring mutations in CCR5 confer protection from HIV-1 infection and disease progression. The most notable CCR5 polymorphism involves a 32 bp deletion in the coding region of CCR5 (A32) (Liu et al., 1996). The A32 allele encodes a nonfunctional receptor that fails to reach the cell surface. Individuals who possess one normal and one mutant CCR5 gene express lower levels of CCR5, and their T cells are less susceptible to R5 virus infection in vitro (Liu et al., 1996; Wu et al., 1997). A32 heterozygotes experience a milder course of disease characterized by reduced viral burdens and delayed progression to AIDS (Huang et al., 1996; Michael et al., 1997). These results support the concept that reducing CCR5 availability can lower viral replication and slow disease progression.

Individuals with two mutant CCR5 genes comprise a significant fraction of people of northern European descent; the demography is suggestive of a prior pandemic of a CCR5-using pathogen. Such individuals represent human CCR5 "knockouts" in that they do not express a functional CCR5 protein. Except in rare instances (Balotta et al., 1997; Biti et al., 1997; O'Brien et al., 1997), these individuals are resistant to HIV-1 infection (Huang et al., 1996; Liu et al., 1996; Michael et al., 1997; Samson et al., 1997), and their T cells cannot be infected with R5 viruses in vitro (Liu et al., 1996). These findings underscore the central role of CCR5 in HIV-1 transmission. In fact, it is now known that R5 viruses mediate transmission in nearly all cases and mediate progression to AIDS in most cases.

Importantly, individuals who lack CCR5 enjoy normal health and display no obvious immunologic or other defects. This may reflect the redundancy of chemokine signaling pathways and the rather limited pattern of expression of CCR5. CCR5 expression is largely confined to activated T cells and macrophages, which represent the primary targets for HIV-1 infection in vivo, although low-level CCR5 expression has been reported on other tissues, such as smooth muscle (Schecter et al., 2000).

CCR5 knockout mice have been generated and provide further insight into the effects of abrogating CCR5 function. CCR5 knockout mice develop normally and are ostensibly healthy, although minor alterations in immune responses can be observed upon challenge with particular pathogens (Huffnagle et al., 1999; Schuh et al., 2002; Tran et al., 2000; Zhou et al., 1998). In contrast, the CXCR4 knockout is a lethal phenotype in mice (Lapidot et al., 2001), and has not been observed in humans.

Taken together, these genetic analyses strongly support a new therapeutic approach based on CCR5 as a drug target. The error-prone nature of reverse transcriptase generates immense genetic diversity that fosters the development of drug-resistant isolates, and HIV-1's ability to utilize multiple fusion coreceptors provides one path to resistance. Drug-resistant viruses have been isolated for all marketed antiretrovirals, which nevertheless provide important therapeutic benefit when used in appropriate combinations. Thus, despite the potential emergence of drug-resistant viruses, CCR5-targeting agents may serve as a new treatment paradigm for HIV-1 infection.

Although the apparent non-essential nature of CCR5 suggests that CCR5 antagonists may be well tolerated in vivo, further studies are required to determine that long-term effects of abrogating CCR5 function in individuals whose immune systems developed in its presence. Such potentially deleterious effects may be mitigated by use of agents that bind to CCR5 and inhibit binding of HIV-1 thereto, but do not impair normal CCR5 function. One agent demonstrated to have such properties is the humanized anti-CCR5 mAb, PRO 140, which effectively blocks HIV-1 replication at concentrations that do not inhibit the physiologic activity of CCR5 (Olson et al., 1999). PRO 140 was identified using a fluorescence resonance energy transfer (RET) assay screen for anti-HIV activity. It is potently antiviral, having an $IC_{90}$ of about 4 µg/ml (Olson et al., 1999; Trkola et al., 2001) and protects diverse primary target cell types (Ketas et al., 2003; Olson and Maddon, 2003). Repeated administration of PRO 140 led to prolonged control of HIV-1 replication without viral escape in the hu-PBL SCID mouse model, and PRO 140 is currently in Phase 1 human clinical trials.

Subsequent to the identification of the small-molecule CCR5 antagonist, TAK-779 (Baba et al., 1999), several other small-molecule CCR5 antagonists have been identified. Four of these (SCH-C, SCH-D, UK-427,857, GW873140) have completed similarly designed Phase 1 studies in HIV-infected individuals (Reynes et al., 2002; Schurmann et al., 2004; Dorr et al., 2003; Lalezari et al., 2004). Each of these agents mediated dose-dependent ~1 $log_{10}$ mean reductions in HIV-1 RNA levels during the treatment period of 10-14 days. As expected, viral loads rebounded to baseline levels following cessation of therapy. The most common drug-related side-effects were neurologic (headache, dizziness) and gastrointestinal (nausea, diarrhea, flatulence), and these were not dose limiting. With the exception of SCH-C (Reyes et al., 2001), none of the above-identified agents induced clinically significant changes in QTc intervals.

A double-blind, placebo-controlled, single oral dose study has also been conducted to evaluate the safety, tolerability, and pharmacokinetics of TAK-652, the successor compound to TAK-779, in healthy male volunteers (Baba et al., 2005). The single administration of TAK-652 solution was reportedly safe and well tolerated (Baba et al., 2005).

Overall, these studies provide preliminary validation of CCR5 as a target for HIV-1 therapy. While the small-molecule CCR5 antagonists represent patentably distinct chemical series with differing pharmacokinetic and metabolic properties, the compounds share many properties in their inhibition of CCR5 function, binding site on CCR5, resistance profiles, and dosing regimen. These similarities may conceivably limit the number of genuine treatment options afforded by small-molecule CCR5 antagonists. Moreover, it remains to be determined whether there are untoward consequences of chronic blockade of CCR5 function, and the utility of small-molecule CCR5 antagonists for HIV-1 therapy remains to be established by demonstration of appropriate safety and efficacy in Phase 3 clinical studies.

Monoclonal Antibody Therapeutics

In recent years, mAb products have provided new standards of care in diverse disease settings.

Currently, 18 mAbs are approved by the U.S. Food and Drug Administration (FDA) for indications including cancer, autoimmune disease, transplant rejection and viral infection. Notably, 14 mAbs have been approved since 2000. In many instances, mAbs provide safety, efficacy and ease-of-use profiles that are unrivalled by small-molecule compounds. Examples include Synagis (MedImmune, Inc., Gaithersburg, Md.), a humanized mAb to respiratory syncytial virus (RSV), and Rituxan (Genentech, San Francisco, Calif.), an anti-CD20 mAb that provides the standard of care for non-Hodgkin's lymphoma.

The humanized anti-CCR5 mAb, PRO 140, is structurally, functionally and mechanistically distinct from the small-molecule CCR5 antagonists and therefore represents a unique CCR5 inhibitor class. PRO 140 is a humanized version of the murine mAb, PA14, which was generated against $CD4^+CCR5^+$ cells (Olson et al., 1999). PRO 140 binds to CCR5 expressed on the surface of a cell, and potently inhibits HIV-1 entry and replication at concentrations that do not affect CCR5 chemokine receptor activity in vitro and in the hu-PBL-SCID mouse model of HIV-1 infection (Olson et al., 1999; Trkola et al., 2001). The latter finding provides in vivo proof-of-concept for PRO 140 anti-HIV-L therapy, and PRO 140 is currently undergoing Phase 1a clinical studies.

Important differences between PRO 140 and small-molecule CCR5 antagonists are summarized in Table 2. It is evident from Table 2 that, whereas small-molecule CCR5 antagonists in development share many properties, PRO 140 is clearly distinct from these small-molecule inhibitors. The differences between the two CCR5 inhibitor classes reveal that PRO 140 may offer a fundamentally distinct, and in many ways complementary, product profile from that of small-molecule CCR5 antagonists. Indeed, PRO 140 represents a novel therapeutic approach to treating HIV-1 infection and could play an important role in HIV-1 therapy irrespective of whether small-molecule CCR5 antagonists are ultimately clinically approved.

Synergistic Inhibition of HIV-1 Infection by Different Classes of Inhibitors

Synergistic inhibition of HIV-1 entry has previously been demonstrated using certain anti-Env antibodies in combination with other anti-Env antibodies (Thali et al., 1992; Tilley et al., 1992; Laal et al., 1994; Vijh-Warrier et al., 1996; Li et al., 1997; Li et al., 1998), anti-CD4 antibodies (Burkly et al., 1995), or CD4-based proteins (Allaway et al., 1993). Similarly, synergies have been observed using anti-CCR5 antibodies in combination with other anti-CCR5 antibodies, CC-chemokines, or CD4-based proteins (Olson et al., 1999). Prior studies described in PCT International Publication No. WO 00/35409, published Jun. 22, 2000, examined combinations of HIV-1 attachment inhibitors and CCR5 coreceptor inhibitors. Prior studies described in PCT International Publication No. WO 01/55439, published Aug. 2, 2001, examined combinations of inhibitors of gp41 fusion intermediates and HIV-1 attachment. Prior studies described in PCT International Publication No. WO 02/22077, published Mar. 21, 2002, examined combinations of fusion inhibitors and CCR5 coreceptor inhibitors, as well as the triple combination of fusion inhibitors, CCR5 coreceptor inhibitors and HIV-1 attachment inhibitors. However, no prior study has examined the combination of different classes of CCR5 coreceptor inhibitors, such as anti-CCR5 mAbs and non-antibody CCR5 antagonists.

TABLE 2

Comparison of PRO 140 and small-molecule CCR5 antagonists

| | Small Molecules | PRO 140 |
|---|---|---|
| Identification Screen | Chemokine Binding | HIV-1 Entry |
| Block Natural Activity of CCR5 | Yes | No |
| Potential for Immune Suppression/Dysregulation | Yes | No |

TABLE 2-continued

Comparison of PRO 140 and small-molecule CCR5 antagonists

| | Small Molecules | PRO 140 |
|---|---|---|
| Tolerability | Cardiac, Neurological Toxicities for some | No Toxicity |
| Binding site on CCR5 | Common Hydrophobic Pocket defined by Transmembrane Regions of CCR5 | Extracellular Epitope that spans Multiple Hydrophilic Domains |
| Viral Cross-Resistance | Significant | Limited |
| Development of Resistance In Vitro | 6 to 19 weeks | None at 40 weeks |
| Drug-Drug Interactions | Significant | Unlikely |
| Food Interactions | Significant | Unlikely |
| Dosing | Once or Twice Daily | Biweekly to Monthly |

SUMMARY OF THE INVENTION

This invention provides a method of reducing viral load in an HIV-1-infected human subject which comprises administering to the subject an effective HIV-1 viral load reducing dose of a CCR5 receptor antagonist, wherein the viral load reducing dose of the CCR5 receptor antagonist achieves an HIV RNA reduction of up to about 2.5 $\log_{10}$ in the subject following administration of the CCR5 receptor antagonist. In an embodiment, the HIV RNA reduction of up to about 2.5 $\log_{10}$ is achieved by about day nine to about day 15 following administration of the CCR5 receptor antagonist to the subject. In an embodiment, the HIV RNA reduction of up to about 2.5 $\log_{10}$ is achieved by about day nine to about day 10 following administration of the CCR5 receptor antagonist to the subject.

This invention also provides a method of reducing viral load in an HIV-1-infected human subject which comprises administering to the subject an effective HIV-1 viral load reducing dose of a CCR5 receptor antagonist, wherein the viral load reducing dose of the CCR5 receptor antagonist achieves an HIV RNA reduction of from 1.20 $\log_{10}$ to 1.83 $\log_{10}$ in the subject following administration of the CCR5 receptor antagonist. In an embodiment, the HIV RNA reduction of from 1.20 $\log_{10}$ to 1.83 $\log_{10}$ is achieved by about day nine to about day 15 following administration of the CCR5 receptor antagonist to the subject. In an embodiment, the HIV RNA reduction of from 1.20 $\log_{10}$ to 1.83 $\log_{10}$ is achieved by about day nine to about day 10 following administration of the CCR5 receptor antagonist to the subject.

This invention also provides a method of reducing viral load in an HIV-1-infected human subject which comprises administering to the subject an effective HIV-1 viral load reducing dose of a CCR5 receptor antagonist, wherein the viral load reducing dose of the CCR5 receptor antagonist achieves a mean $\log_{10}$ HIV RNA change of from about −1.0 to about −1.7 in the subject by about day five to about day ten following administration of the CCR5 receptor antagonist.

This invention also provides a method of reducing viral load in an HIV-1-infected human subject which comprises administering to the subject an effective HIV-1 viral load reducing dose of a CCR5 receptor antagonist, wherein the effective HIV-1 viral load reducing dose results in a greater than ten-fold decrease in HIV RNA in the subject at about ten days following administration of the CCR5 receptor antagonist.

The invention also provides a method of reducing viral load in an HIV-1-infected human subject which comprises administering to the subject an effective HIV-1 viral load reducing dose of a CCR5 receptor antagonist, wherein the effective HIV-1 viral load reducing dose results in a ≥1 $\log_{10}$ decrease in HIV RNA in the subject at about day 5 to about day 15 following administration of the CCR5 receptor antagonist. In an embodiment, the ≥1 $\log_{10}$ decrease in HIV RNA in the subject persists for about two to three weeks.

In the above methods, the reduction of viral load or of HIV RNA in the subject persists at or below a level of reduction of about 1.0 $\log_{10}$ for about ten days to about three weeks, or for about two to three weeks. In one embodiment, the viral load reducing dose of the CCR5 receptor antagonist is a single dose administered intravenously. In one embodiment, the viral load reducing dose of the CCR5 receptor antagonist is a multiple dose administered intravenously. In one embodiment, the viral load reducing dose of the CCR5 receptor antagonist is administered subcutaneously. In one embodiment, the viral load reducing dose of the CCR5 receptor antagonist is administered subcutaneously once or twice a week. In another embodiment of the above methods, the CCR5 receptor antagonist is (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099).

In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

This invention provides a method of reducing viral load in an HIV-1-infected human subject which comprises: administering to the subject an effective HIV-1 viral load reducing dose of (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:Hu-PRO140 (mut B+D+I)-VH (ATCC Deposit Designation PTA-4099), wherein the effective HIV-1 viral load-reducing dose is selected from 2 mg per kg to 25 mg per kg of the subject's body weight, so as to thereby reduce the subject's HIV-1 viral load. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098). In an embodiment, the effective viral load-reducing dose is 5 mg per kg of the subject's body weight. In an embodiment, the effective viral load-reducing dose is 10 mg/kg of the subject's body weight. In an embodiment, the effective viral load-reducing dose is 15 mg/kg of the subject's body weight. In an embodiment, the effective viral load-reducing dose is 20 mg/kg or 25 mg/kg of the subject's body weight.

This invention also provides method of elevating CD4+ cell count in an HIV-1-infected human subject which comprises: administering to the subject an effective CD4+ cell count-elevating dose of (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:Hu-PRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In an embodiment, PRO 140 comprises (i) two light chains, each light chain comprising the light chain variable ($V_L$) and constant ($C_L$) regions encoded by the plasmid designated pVK:Hu-PRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

This invention further provides a method of reducing viral load in an HIV-1-infected human subject which comprises: administering to the subject an effective HIV-1 viral load reducing dose of (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:Hu-PROt40-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099), wherein the effective HIV-1 viral load-reducing dose is administered subcutaneously, so as to thereby reduce the subject's HIV-1 viral load. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:Hu-PRO140 HG2-VH (ATCC Deposit Designation PTA-4098). In another embodiment, the viral load-reducing dose is administered subcutaneously every week. In one embodiment, the viral load-reducing dose is administered subcutaneously every two weeks. In one embodiment, the viral load-reducing dose is administered subcutaneously every three weeks. In one embodiment, the viral load-reducing dose is administered subcutaneously one or more times per week. In one embodiment, the viral load-reducing dose is administered subcutaneously twice per week. In one embodiment, the viral load-reducing dose is administered subcutaneously more than twice per week. In one embodiment, the subcutaneous viral load-reducing dose is from 1.5 mg per kg to 25 mg per kg of the subject's body weight. In one embodiment, the subcutaneous viral load-reducing dose is from 2 mg per kg to 10 mg per kg of the subject's body weight. In one embodiment, the subcutaneous viral load-reducing dose is from 2 mg per kg to 7.5 mg per kg of the subject's body weight.

This invention also provides methods of reducing viral load in an HIV-1-infected human subject by multiple dosing of the subject. The invention provides a method of maintaining a reduction of viral load in an HIV-1-infected human subject, which comprises (a) administering to the subject a first effective HIV-1 viral load reducing dose of (1) a humanized antibody designated PRO 140, or of (2) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099), wherein the first effective HIV-1 viral load-reducing dose results in a viral load reduction of up to about 2.5 $\log_{10}$ in the subject by about day 9 to about day 15 following dosing of the subject; and (b) administering to the subject one or more subsequent effective HIV-1 viral load reducing doses of the humanized antibody designated PRO 140 of (1) or the anti-CCR5 receptor monoclonal antibody of (2) at repeated intervals thereafter. For example, further doses may be administered to the subject at a time when the subject's viral load reduction is determined to be from about 0.7 to 1.5 $\log_{10}$, or 1.0 $\log_{10}$, relative to baseline, after a first or subsequent dose, so as to thereby maintain a reduced viral load in the subject. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

This invention also provides a method of maintaining a reduced viral load in an HIV-1-infected human subject, which comprises (a) administering to the subject a first effective HIV-1 viral load reducing dose of a CCR5 receptor antagonist, wherein the first effective HIV-1 viral load-reducing dose results in an up to 2.5 $\log_{10}$ reduction in HIV-1 RNA by about day 9 to about day 15 following dosing of the subject; and (b) administering to the subject one or more subsequent effective HIV-1 viral load reducing doses of the CCR5 receptor antagonist at repeated intervals thereafter, for example, at a time when the subject's viral load reduction is determined to be about 0.7 to 1.5 $\log_{10}$, or 1.0 $\log_{10}$, so as to thereby maintain a reduced viral load in the subject.

This invention also provides a method of reducing viral load in an HIV-L-infected subject, which comprises (a) determining that the subject is infected with a CCR5-tropic HIV-1 strain; and (b) administering to the subject an effective HIV-1 viral load reducing dose of a CCR5 receptor antagonist which is selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In an embodiment of the method, the CCR5 receptor antagonist achieves an average maximum decrease of viral load in the subject of up to 2.5 $\log_{10}$ by about day nine or day ten following administration. In another embodiment of the method, the CCR5 receptor antagonist achieves an HIV RNA reduction of from 1.20 $\log_{10}$ to 1.83 $\log_{10}$ by about day nine or day ten following administration. In another embodiment of the method, the CCR5 receptor antagonist achieves a $\log_{10}$ HIV RNA change of from about −1.0 to about −1.7 in the subject by about day five to about day ten following administration. In another embodiment of the method, the CCR5 receptor antagonist achieves a greater than ten-fold decrease in HIV RNA in the subject at about ten days following administration. In another embodiment of the method, the CCR5 receptor antagonist achieves a greater than or equal to 1 $\log_{10}$ decrease in HIV RNA in the subject at about day five to about day fifteen following administration. In an embodiment, the CCR5 receptor antagonist is administered intravenously or subcutaneously. In an embodiment, the effective HIV-1 viral load reducing dose of the CCR5 receptor antagonist is selected from 2 mg/kg. 5 mg/kg, 7.5 mg/kg, 10 mg/kg, 15 mg/kg, 20 mg/kg, or 25 mg/kg of the subject's body weight. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

The invention provides a method in which an HIV-infected subject who is to receive a viral load reducing dose of a CCR5 receptor antagonist is tested diagnostically prior to the administration of the CCR5 receptor antagonist to determine if the subject is infected with a CCR5-tropic strain of HIV. In an embodiment, the subject is monitored at predetermined intervals during the administration of the CCR5 receptor antagonist to determine one or more of viral load, CD4 cell count, HIV tropism, HIV resistance, and/or the development of tumors, malignancies, or infections. In an embodiment, the monitoring is carried out about once every three weeks, once a month, twice a month, once every six weeks, once every two to six months, or two to six times a year. In an embodiment, the CCR5 receptor antagonist is selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating 3-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In an embodiment, PRO 140 comprises (i) two light chains, each light chain comprising the light chain variable ($V_L$) and constant ($C_L$) regions encoded by the plasmid designated pVK:Hu-PRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

This invention further provides a CCR5 receptor antagonist which, when administered to an HIV-infected subject, achieves an average maximum decrease of viral load in the subject of up to 2.5 $\log_{10}$ by about day nine or day ten following administration. The invention also provides a CCR5 receptor antagonist which, when administered to an HIV-infected subject, achieves an HIV RNA reduction of from 1.20 $\log_{10}$ to 1.83 $\log_{10}$ by about day nine or day ten following administration. Also provided is a CCR5 receptor antagonist which, when administered to an HIV-infected subject, achieves a $\log_{10}$ HIV RNA change of from about −1.0 to about −1.7 in the subject by about day five to about day ten following administration. The invention also provides a CCR5 receptor antagonist which, when administered to an HIV-infected subject, results in a greater than ten-fold decrease in HIV RNA in the subject at about ten days following administration. The invention also provides a CCR5 receptor antagonist which, when administered to an HIV-infected subject, results in a greater than or equal to 1 $\log_{10}$ decrease in HIV RNA in the subject at about day five to about day fifteen following administration. In an embodiment, the CCR5 receptor antagonist of the above is selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:Hu-PRO140 (mut B+D+I)-VH (ATCC Deposit Designation PTA-4099). In an embodiment, administration of the CCR5 receptor antagonist results in a viral load reduction in the subject that persists for about two to three weeks. In an embodiment, the CCR5 receptor antagonist is administered in a dose selected from 2 mg/kg, 5 mg/kg, 10 mg/kg, 15 mg/kg, or 20 mg/kg of the subject's body weight. In another embodiment, the CCR5 receptor antagonist is administered intravenously or subcutaneously. In an embodiment, a composition is provided which comprises any of the CCR5 receptor antagonists as described herein and a pharmaceutically acceptable carrier, excipient, or diluent. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:Hu-PRO140 HG2-VH (ATCC Deposit Designation PTA-4098).

The invention further provides the use of a viral load reducing amount of a CCR5 antagonist, e.g., PRO 140, in combination with one or more HIV-1 entry inhibitors or therapeutics, for example, as presented in Table 1. In an embodiment the HIV-L entry inhibitor is a monoclonal or humanized antibody or a portion thereof. In an embodiment, the HIV-1 entry inhibitor is TNX-355 (Genentech/Tanox), a humanized antibody that is directed against CD4 and prevents HIV-1 entry at the post-attachment stage of virus infection.

The invention further provides the use of a humanized antibody designated PRO 140, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099) as a salvage therapy for the treatment of HIV-1 infection or AIDS in a subject requiring such treatment or therapy. In an embodiment, PRO 140 is provided as a salvage therapy after a subject has been found not to respond to one or more standard anti-HIV drug treatments or regimens. In an embodiment, PRO 140 is provided in combination with other anti-HIV drugs as a salvage therapy. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:Hu-PRO140 HG2-VH (ATCC Deposit Designation PTA-4098).

BRIEF DESCRIPTION OF THE FIGURES

FIG. 18: Table showing results of Phase 1b Study.

FIG. 33 presents the duration of time (in days) below a 1 $\log_{10}$ drop in viral load. In the 162 mg, Days 1, 8 and 15 group, N=11; in the 324 mg, Days 1, 15 group, N=12; and in the 324 mg, Days 1, 8, 15 group, N=11.

DETAILED DESCRIPTION AND EMBODIMENTS OF THE INVENTION

Figure 1:
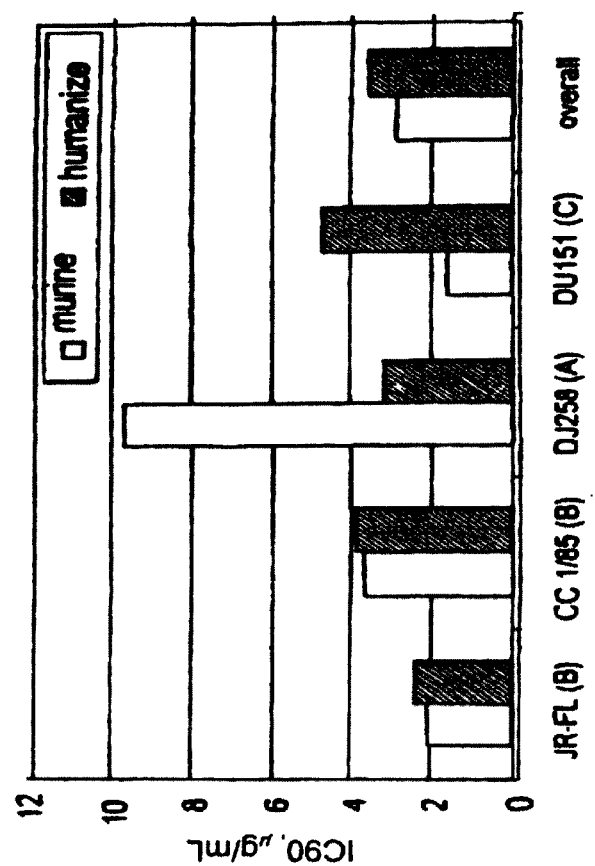
FIG. 1: Humanized PRO140 is potently antiviral. The in vitro neutralization activity of murine and humanized PRO 140 was tested against four primary R5 HIV-1 isolates using a whole virus replication assay. The data reflect the median values from 8 or more independent assays. The genetic subtypes of the viruses are indicated in parentheses.

Terms:

As used in this application, except as otherwise expressly provided herein, each of the following terms shall have the meaning set forth below.

"Administering" refers to delivering in a manner which is effected or performed using any of the various methods and delivery systems known to those skilled in the art. Administering can be performed, for example, topically, intravascularly, intravenously, pericardially, orally, parenterally, via implant, transmucosally, dermally, transdermally, intradermally, intramuscularly, subcutaneously, intraperitoneally, intrathecally, intralymphatically, intralesionally, epidurally, rectally, intravaginally, intraocularly, intrasinally, nasally, intraspinally, mucosally, transmucosally, transplacentally or by in vive electroporation. An agent or composition may also be administered in an aerosol, such as for pulmonary and/or intranasal delivery. Administering can also be performed, for example, once, a plurality of times, and/or over one or more extended periods.

An "antibody" shall include, without limitation, an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. "Antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Methods for humanizing antibodies are well known to those skilled in the art. "Antibody" also includes, without limitation, a fragment or portion of any of the afore-mentioned immunoglobulin molecules and includes a monovalent and a divalent fragment or portion. Antibody fragments include, for example, Fc fragments and antigen-binding fragments (Fab).

An "anti-chemokine receptor antibody" refers to an antibody which recognizes and binds to an epitope on a chemokine receptor. As used herein, "anti-CCR5 antibody" refers to an antibody which recognizes and binds to an epitope on the CCR5 chemokine receptor.

"Attachment" means the process that is mediated by the binding of the HIV-1 envelope glycoprotein to the human CD4 receptor, which is not a fusion coreceptor.

As used herein, "CCR5", or "R5", is a chemokine receptor which binds members of the C—C group of chemokines and whose amino acid sequence comprises that provided in Genbank Accession Number 1705896 and related polymorphic variants. As used herein, CCR5 includes, without limitation, extracellular portions of CCR5 capable of binding the HIV-1 envelope protein. "CCR5" and "CCR5 receptor" are used synonymously.

"CD4" means the mature, native, membrane-bound CD4 protein comprising a cytoplasmic domain, a hydrophobic transmembrane domain, and an extracellular domain which binds to the HIV-1 gp120 envelope glycoprotein.

"CDR", or complementarity determining region, means a highly variable sequence of amino acids in the variable domain of an antibody.

A "cell" includes a biological cell, e.g., a HeLa cell, a lymphocyte, a PBMN cell, and a non-biological cell, e.g., a phospholipid vesicle or virion. A "cell susceptible to HIV infection" may also be referred to as a "target cell" and includes a cell capable of being infected by or fusing with HIV or an HIV-infected cell.

"CXCR4" or "R4" is a chemokine receptor which binds members of the C—X—C group of chemokines and whose amino acid sequence comprises that provided in Genbank Accession No 400654 and related polymorphic variants. As used herein, CXCR4 includes extracellular portions of CXCR4 capable of binding the HIV-1 envelope protein.

"Exposed" to HIV-1 refers to contact with HIV-1 such that infection could result.

A "fully human" antibody refers to an antibody wherein all of the amino acids correspond to amino acids in human immunoglobulin molecules. "Fully human" and "human" are used synonymously.

"HIV" refers to the human immunodeficiency virus. HIV shall include, without limitation, HIV-1. HIV-1 includes but is not limited to extracellular virus particles and the forms of HIV-1 associated with HIV-1 infected cells. The human immunodeficiency virus (HIV) may be either of the two known types of HIV (HIV-1 or HIV-2). The HIV-1 virus may represent any of the known major subtypes (classes A, B, C, D, E, F, G, H, or J), outlying subtype (Group O), or an as yet to be determined subtype of HIV-1. HIV-1$_{JR\text{-}FL}$ is a strain that was originally isolated at autopsy from the brain tissue of an AIDS patient. The virus has been cloned and the DNA sequences of its envelope glycoproteins are known (GenBank Accession No. U63632). In terms of sensitivity to inhibitors of viral entry, HIV-1$_{JR\text{-}FL}$ is known to be highly representative of primary HIV-1 isolates.

A "humanized" antibody refers to an antibody wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules, whereas some, most or all amino acids within one or more CDR regions are unchanged. Small additions, deletions, insertions, substitutions or modifications of amino acids are permissible as long as they do not abrogate the ability of the antibody to bind a given antigen. Suitable human immunoglobulin molecules include IgG1, IgG2, IgG3, IgG4, IgA, IgE and IgM molecules. A "humanized" antibody retains an antigenic specificity similar to that of the original antibody.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody.

U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site-directed mutagenesis is used to graft the CDRs onto the framework.

Other approaches for humanizing an antibody are described in U.S. Pat. Nos. 5,585,089 and 5,693,761, and PCT International Publication No. WO 90/07861, which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody. The above methods are merely illustrative of some of the methods that one skilled in the art could employ to make humanized antibodies.

Methods for making fully human antibodies are also well known to one skilled in the art. For example, fully human monoclonal antibodies can be prepared by immunizing animals transgenic for large portions of human immunoglobulin heavy and light chain loci. See, e.g., U.S. Pat. Nos. 5,591,669, 5,545,806, 5,545,807, 6,150,584, and references cited therein, the contents of which are incorporated herein by reference. These transgenic animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these animals (e.g., XenoMouse® (Abgenix), HuMAb-Mouse® (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Nucleic acids encoding heavy and light chains of the humanized PRO 140 antibody have been deposited with the ATCC. Specifically, the plasmids designated pVK-HuPRO 140, pVg4-HuPRO140 (mut B+D+I) and pVg4-HuPRO140 HG2, respectively, were deposited pursuant to, and in satisfaction of, the requirements of the Budapest Treaty with the ATCC, Manassas, Va., U.S.A. 20108, on Feb. 22, 2002, under ATCC Accession Nos. PTA 4097, PTA 4099 and PTA 4098, respectively. The American Type Culture Collection (ATCC) is now located at 10801 University Boulevard, Manassas, Va. 20110-2209.

The half-life of the humanized PRO 140 antibody may be increased to prolong exposure of the drug following administration. For example, the half-life of PRO 140 in serum or plasma may be extended, and/or the amount and time that PRO 140 coats CCR5+ target cells may be extended. Illustrative methods include conjugation to polyethylene glycol (PEG), (pegylation), or monomethoxypolyethylene glycol (mPEG); and molecularly engineering PRO 140, e.g., by site directed mutagenesis, to have altered pH-dependent binding to the human neonatal Fc receptor (FcRn), an MHC class I-like Fc receptor. (See, e.g., S. B. Petkova et al., 2006, Int'l Immunol., 18(12):1759-1769; P. R. Hinton et al., 2006, J. Immunol., 176:346-356).

The production of antibody or antibody fragment-polymer conjugates having an effective size or molecular weight that confers an increase in serum half-life, an increase in mean residence time in circulation (MRT) and/or a decrease in serum clearance rate over underivatized antibody or antibody fragments. The antibody fragment-polymer conjugates can be made by derivatizing the desired antibody fragment with an inert polymer. It will be appreciated that any inert polymer which provides the conjugate with the desired apparent size, or which has the selected actual molecular weight, is suitable for use in constructing suitable antibody fragment-polymer conjugates.

Many inert polymers are suitable for use in pharmaceuticals. See, e.g., Davis et al., Biomedical Polymers: Polymeric Materials and Pharmaceuticals for Biomedical Use, pp. 441-451 (1980). A non-proteinaceous polymer is particularly advantageous. The non-proteinaceous polymer ordinarily is a hydrophilic synthetic polymer, i.e., a polymer not otherwise found in nature. However, polymers which exist in nature and are produced by recombinant or in vitro methods are also useful, as are polymers which are isolated from native sources. Hydrophilic polyvinyl polymers, e.g., polyvinylalcohol and polyvinvypyrrolidone, are suitable. Particularly useful are polyalkylene ethers such as polyethylene glycol (PEG); polyoxyalklyenes such as polyoxyethylene, polyoxypropylene and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g., polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g., hyaluronic acid, polymers of sugar alcohols such as polysorbitol and polymannitol, heparin or heparon. The polymer prior to cross-linking need not, but can be, water soluble, but the final conjugate needs to be water soluble. The conjugate exhibits a water solubility of at least about 0.01 mg/ml, or at least about 0.1 mg/ml, or at least about 1 mg/ml. In addition the polymer should not be highly immunogenic in the conjugate form, nor should it possess viscosity that is incompatible with intravenous infusion or injection if the conjugate is intended to be administered by such routes.

In one embodiment, the polymer contains only a single group that is reactive. This helps to avoid cross-linking of protein molecules. However, reaction conditions can be maximized to reduce cross-linking, or to purify the reaction products through gel filtration or ion-exchange chromatography to recover substantially homogeneous derivatives. In other embodiments, the polymer contains two or more reactive groups for the purpose of linking multiple antibody fragments to the polymer backbone. Again, gel filtration or ion-exchange chromatography can be used to recover the desired derivative in substantially homogeneous form.

The molecular weight of the polymer can range up to about 500,000 Daltons (D) and can be at least about 20,000 D, or at least about 30,000 D, or at least about 40,000 D. The molecular weight chosen can depend upon the effective size of the conjugate to be achieved, the nature (e.g., structure such as linear or branched) of the polymer and the degree of derivitization, i.e., the number of polymer molecules per antibody fragment, and the polymer attachment site or sites on the antibody fragment.

The polymer can be covalently linked to the antibody or fragment thereof through a multifunctional crosslinking agent, which reacts with the polymer and one or more amino acid residues of the antibody or fragment to be linked. The polymer may be crosslinked directly by reacting a derivatized polymer with the antibody or antibody fragment, or vice versa. The covalent crosslinking site on the antibody or antibody fragment includes the N-terminal amino group and epsilon amino groups found on lysine residues, as well other amino, imino, carboxyl, sulfhydryl, hydroxyl, or other hydrophilic groups. The polymer may be covalently bonded directly to the antibody or antibody fragment without the use of a multifunctional (ordinarily bifunctional) crosslinking agent, as described, for example, in U.S. Pat. No. 6,458,355.

The degree of substitution with such a polymer will vary depending upon the number of reactive sites on the antibody or fragment thereof, the molecular weight, hydrophilicity and other characteristics of the polymer, and the particular antibody or antibody fragment derivitization sites chosen. In general, the conjugate contains from 1 to about 10 polymer molecules, but greater numbers of polymer molecules attached to the antibodies or antibody fragments are also contemplated. The desired amount of derivitization is easily achieved by using an experimental matrix in which the time, temperature and other reaction conditions are varied to change the degree of substitution, after which the level of polymer substitution of the conjugates is determined by size exclusion chromatography or other means known and practiced in the art.

Functionalized polyethylene glycol (PEG) polymers to modify the antibody or antibody fragments are available from Shearwater Polymers, Inc. (Huntsville, Ala.). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG-vinylsulfone, PEG-maleimide, PEG-orthopyridyl-disulfide, heterofunctional PEGs, PEG vinyl derivatives, PEG silanes and PEG phospholides. The reaction conditions for coupling these PEG derivatives will vary depending on the protein, the desired degree of PEGylation and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer. The resulting conjugates are separated from the unreacted starting materials by gel filtration or ion exchange HPLC.

"Monoclonal antibodies," also designated a mAbs, are antibody molecules whose primary sequences are essentially identical and which exhibit the same antigenic specificity. Monoclonal antibodies may be produced by hybridoma, recombinant, transgenic or other techniques known to those skilled in the art.

A "non-antibody antagonist of a CCR5 (or "R5") receptor" refers to an agent that does not comprise an antibody, and which binds to a CCR5 receptor and inhibits the activity of this receptor. Such inhibition can include inhibiting the binding of HIV-1 to the CCR5 receptor. By way of example, non-antibody antagonists include nucleic acids, carbohydrates, lipids, oligopeptides, non-chemokines and non-protein, small organic molecules.

A "small-molecule" CCR5 receptor antagonist includes, for example, a small organic molecule, or a non-protein small organic molecule, which binds to a CCR5 receptor and inhibits the activity of the receptor. Such inhibition includes, e.g., inhibiting the binding of HIV-1 to the receptor or inhibiting the entry of HIV-1 into a susceptible cell. In one embodiment, the small organic molecule has a molecular weight less than 1,500 daltons. In another embodiment, the molecule has a molecular weight less than 600 daltons.

"Subject" includes any animal or artificially modified animal capable of becoming infected with HIV. Animals include, but are not limited to, humans, non-human primates, dogs, cats, rabbits, ferrets, and rodents such as mice, rats and guinea pigs. Artificially modified animals include, but are not limited to, SCID mice with human immune systems. In an embodiment, the subject is a human. In an embodiment, the subject is a human patient.

"Synergy" between two or more agents refers to the combined effect of the agents which is greater than their additive effects. Illustratively, agents may be peptides, proteins, such as antibodies, small molecules, organic compounds, and drug forms thereof. Synergistic, additive or antagonistic effects between agents may be quantified by analysis of the dose-response curves using the Combination Index (CI) method. A CI value greater than 1 indicates antagonism; a CI value equal to 1 indicates an additive effect; and a CI value less than 1 indicates a synergistic effect. In one embodiment, the CI value of a synergistic interaction is less than 0.9. In another embodiment, the CI value is less than 0.8. In a preferred embodiment, the CI value is less than 0.7.

Embodiments of the Invention

In one embodiment, the invention provides a method of reducing viral load in an HIV-1-infected human subject which comprises administering to the subject an effective HIV-1 viral load reducing dose of a CCR5 receptor antagonist, wherein the viral load reducing dose of the CCR5 receptor antagonist achieves an HIV RNA reduction of up to about 2.5 $\log_{10}$ in the subject following administration of the CCR5 receptor antagonist. In an embodiment, the HIV RNA reduction of up to about 2.5 $\log_{10}$ is achieved by about day nine or about day 10 following administration of the CCR5 receptor antagonist to the subject. In an embodiment, the viral load reducing dose of the CCR5 receptor antagonist achieves an average maximum decrease of HIV RNA viral load in the subject of at least 1.83 $\log_{10}$ to 2.5 $\log_{10}$ at about nine to ten days following administration of the CCR5 receptor antagonist.

In another embodiment, the invention provides a method of reducing viral load in an HIV-1-infected human subject which comprises administering to the subject an effective HIV-1 viral load reducing dose of a CCR5 receptor antagonist, wherein the viral load reducing dose of the CCR5 receptor antagonist achieves an HIV RNA reduction of from 1.20 $\log_{10}$ to 1.83 $\log_{10}$ in the subject following administration of the CCR5 receptor antagonist. In an embodiment, the HIV RNA reduction of from 1.20 $\log_{10}$ to 1.83 $\log_{10}$ is achieved by about day nine or about day 10 following administration of the CCR5 receptor antagonist to the subject.

In another embodiment, the invention provides a method of reducing viral load in an HIV-1-infected human subject which comprises administering to the subject an effective HIV-1 viral load reducing dose of a CCR5 receptor antagonist, wherein the viral load reducing dose of the CCR5 receptor antagonist achieves a mean $\log_{10}$ HIV RNA change of from about −1.0 to about −1.7 in the subject by about day five to about day ten following administration of the CCR5 receptor antagonist. In an embodiment, the viral load reducing dose of the CCR5 receptor antagonist achieves a mean viral load reduction of 1.7 $\log_{10}$ at about nine to ten days following administration of the CCR5 receptor antagonist.

In another embodiment, the invention provides a method of reducing viral load in an HIV-1-infected human subject which comprises administering to the subject an effective HIV-1 viral load reducing dose of a CCR5 receptor antagonist, wherein the effective HIV-1 viral load reducing dose results in a greater than ten-fold decrease in HIV RNA in the subject at about ten days following administration of the CCR5 receptor antagonist.

In another embodiment, the invention provides a method of reducing viral load in an HIV-1-infected human subject which comprises administering to the subject an effective HIV-1 viral load reducing dose of a CCR5 receptor antagonist, wherein the effective HIV-1 viral load reducing dose results in a ≥1 $\log_{10}$ decrease in HIV RNA in the subject at about day 5 to about day 15 following administration of the CCR5 receptor antagonist.

In an embodiment, in accordance with the methods of the invention, the reduction of viral load, or the reduction of HIV RNA, in the subject persists at ≥1 $\log_{10}$ for about ten days to about three weeks, or for about two to three weeks. In one embodiment, the viral load reducing dose of the CCR5 receptor antagonist is a single dose administered intravenously. In one embodiment, the viral load reducing dose of the CCR5 receptor antagonist is a multiple dose administered intravenously. In one embodiment, the viral load reducing dose of the CCR5 receptor antagonist is administered subcutaneously. In one embodiment, the viral load reducing dose of the CCR5 receptor antagonist is administered subcutaneously every week or every two weeks. In one embodiment, the viral load reducing dose of the CCR5 receptor antagonist is administered subcutaneously one or more times per week or one or more times every two weeks. In an embodiment, the SC regimen comprises q1 week. In an embodiment, the SC regimen comprises q2 weeks. In an embodiment, SC administration reduces viral load by 1-2.5 $\log_{10}$, or by 1.5-2 $\log_{10}$. In an embodiment, the q1 week and q2 weeks SC regimens reduce viral load by 1-2.5 $\log_{10}$, or by 1.5-2 $\log_{10}$.

In another embodiment of the above methods, the CCR5 receptor antagonist is (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:Hu-PRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099).

In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:Hu-PRO140 HG2-VH (ATCC Deposit Designation PTA-4098). In an embodiment, the viral load reducing dose is of the antibody is 25 mg/kg of the subject's body weight. In one embodiment, the viral load reducing dose of the antibody is 5 mg/kg of the subject's body weight. In one embodiment, the viral load reducing dose of the antibody is 7.5 mg/kg of the subject's body weight. In one embodiment, the viral load reducing dose of the antibody is 10 mg/kg of the subject's body weight. In one embodiment, the viral load reducing dose of the antibody is 15 mg/kg of the subject weight. In one embodiment, the viral load reducing dose of the antibody is 15 mg/kg of the subject's body weight. In one embodiment, the viral load reducing dose of the antibody is 20 mg/kg of the subject's body weight. In one embodiment, the viral load reducing dose of the antibody is 25 mg/kg of the subject's body weight. In one embodiment, the viral load reducing dose of the antibody, e.g., PRO 140, is administered intravenously every two weeks (q2 weeks) or every four weeks (q4 weeks). In an embodiment, the viral load reducing dose of the antibody, e.g., PRO 140, is administered intravenously weekly, every two weeks, every three weeks, every four weeks, every five weeks, every six weeks, every seven weeks, every eight weeks, every nine weeks, or every ten weeks. In an embodiment, the viral load reducing dose of the antibody, e.g., PRO 140, is a monthly intravenous dose of 300 to 1000 mg. In an embodiment, the viral load reducing dose of the antibody, e.g., PRO 140, is a monthly intravenous dose of 500 to 900 mg. In an embodiment, the viral load reducing dose of the antibody, e.g., PRO 140, is a monthly intravenous dose of 500 to 800 mg. In an embodiment, the viral load reducing dose of the antibody, e.g., PRO 140, is a monthly intravenous dose of 800 mg. In an embodiment related to the foregoing embodiments, the viral load reducing dose of the antibody, e.g., PRO 140, maintains the viral load below a 1 $\log_{10}$ decrease for 3 months to a year.

In an embodiment, the invention provides a method of reducing viral load in an HIV-1-infected human subject which comprises: administering to the subject an effective HIV-1 viral load reducing dose of (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating 3-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4: HuPRO140 HG2-VH (ATCC Deposit Designation PTA-4098) or by the plasmid designated pVg4:HuPRO140 (mut B+D+I)-VH (ATCC Deposit Designation PTA-4099), wherein the effective HIV-1 viral load-reducing dose is selected from 2 mg per kg to 25 mg per kg of the subject's body weight, so as to thereby reduce the subject's HIV-1 viral load. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

In an embodiment, the invention provides method of elevating CD4+ cell count in an HIV-1-infected human subject which comprises administering to the subject an effective CD4+ cell count-elevating dose of (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4: HuPRO140 HG2-VH (ATCC Deposit Designation PTA-4098) or by the plasmid designated pVg4:HuPRO140 (mut B+D+I)-VH (ATCC Deposit Designation PTA-4099), wherein the effective CD4+ cell count-elevating dose is from 0.1 mg to 25 mg/kg of the subject's body weight, so as to thereby elevate the subject's CD4+ cell count. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant (Cu) regions encoded by the plasmid designated pVg4:HuPRO140 HG2-VH (ATCC Deposit Designation PTA-4098). In an embodiment, the effective CD4+ cell count-elevating dose of the antibody is 5 mg/kg of the subject's body weight. In an embodiment, the effective CD4+ cell count-elevating dose of the antibody is 10 mg per kg of the subject's body weight. In an embodiment, the effective CD4+ cell count-elevating dose of the antibody is 15 mg per kg of the subject's body weight. In an embodiment, the effective CD4+ cell count-elevating dose of the antibody is 20 mg per kg of the subject's body weight. In an embodiment, the effective CD4+ cell count-elevating dose of the antibody is 25 mg per kg of the subject's body weight. In an embodiment, the administration of the humanized antibody designated PRO 140 of (a), or the anti-CCR5 receptor monoclonal antibody of (b) is via an intravenous route. In an embodiment, the administration of the humanized antibody designated PRO 140 of (a), or the anti-CCR5 receptor monoclonal antibody of (b) is via a subcutaneous route.

In an embodiment, the invention provides a method of reducing viral load in an HIV-1-infected human subject which comprises administering to the subject an effective HIV-1 viral load reducing dose of (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4: HuPRO140 HG2-VH (ATCC Deposit Designation PTA- 4098) or by the plasmid designated pVg4:HuPRO140 (mut B+D+I)-VH (ATCC Deposit Designation PTA-4099), wherein the effective HIV-1 viral load-reducing dose is administered subcutaneously, so as to thereby reduce the subject's HIV-1 viral load. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098). In one embodiment, the viral load-reducing dose is administered subcutaneously every week. In one embodiment, the viral load-reducing dose is administered subcutaneously every two weeks. In one embodiment, the viral load-reducing dose is administered subcutaneously every three weeks. In other embodiments, the SC viral load reducing dose regimen is q1 week or q2 weeks. In an embodiment, the SC viral load-reducing dose is administered subcutaneously one or more times per week. In one embodiment, the SC viral load-reducing dose is administered subcutaneously twice per week. In one embodiment, the SC viral load-reducing dose is from 1.5 mg per kg to 25 mg per kg of the subject's body weight. In one embodiment, the SC viral load-reducing dose is from 2 mg per kg to 15 mg per kg of the subject's body weight. In one embodiment, the SC viral load-reducing dose is from 2 mg per kg to 7.5 mg per kg of the subject's body weight. In one embodiment, the HIV-1 viral load-reducing dose administered subcutaneously is 2 mg/kg of the subject's body weight. In one embodiment, the HIV-1 viral load-reducing dose administered subcutaneously is 4 mg/kg of the subject's body weight. In one embodiment, the HIV-1 viral load-reducing dose administered subcutaneously is 5 mg/kg of the subject's body weight. In one embodiment, the HIV-1 viral load-reducing dose administered subcutaneously is 7.5 mg/kg of the subject's body weight. In various embodiments, the SC viral load-reducing dose is 50 mg, 100 mg, 150 mg, 200 mg, 250 mg, 300 mg, 350 mg, 360 mg, or 400 mg. In one embodiment, one or more subcutaneously administered HIV-1 viral load-reducing doses is/are delivered weekly, once per week, twice per week, three times per week, every two weeks (biweekly), once every two weeks, twice every two weeks, three times every two weeks, every three weeks, two times every three weeks, once a month, or twice or more a month. In an embodiment, an HIV-1 viral load reducing dosing regimen comprises 150 mg administered weekly to a subject. In an embodiment, an HIV-1 viral load reducing dosing regimen comprises 300 mg administered weekly to a subject. In an embodiment, an HIV-1 viral load reducing dosing regimen comprises 300 mg administered biweekly to a subject.

In an embodiment, this invention provides methods of reducing viral load in an HIV-1-infected human subject by multiple dosing of the subject. The invention provides a method of maintaining a reduction of viral load in an HIV-1-infected human subject, which comprises (a) administering to the subject a first effective HIV-1 viral load reducing dose of (1) a humanized antibody designated PRO 140, or of (2) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099), wherein the first effective HIV-1 viral load-reducing dose results in a viral load reduction of up to about 2.5 $\log_{10}$ in the subject by about day 9 to about day 15 following dosing of the subject; and (b) administering to the subject one or more subsequent effective HIV-1 viral load reducing doses of the humanized antibody designated PRO 140 of (1) or the anti-CCR5 receptor monoclonal antibody of (2) at repeated intervals thereafter. Illustratively, and without intending to be limiting, the additional doses may be administered at a time when the subject's HIV viral load reduction is determined to be about 0.7 to 1.5 $\log_{10}$, or 1.0 $\log_{10}$, relative to baseline, so as to thereby maintain a reduced viral load in the subject for prolonged time periods. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

In another embodiment, the invention provides a method of maintaining a reduced viral load in an HIV-1-infected human subject, which comprises (a) administering to the subject a first effective HIV-1 viral load reducing dose of a CCR5 receptor antagonist, wherein the first effective HIV-1 viral load-reducing dose results in an up to 2.5 $\log_{10}$ reduction in HIV-1 RNA by about day 9 to about day 15 following dosing of the subject; and (b) administering to the subject one or more subsequent effective HIV-1 viral load reducing doses of the CCR5 receptor antagonist at repeated intervals thereafter. For example, the one or more subsequent doses may be administered at a time when the subject's HIV viral load reduction is determined to be about 0.7 to 1.5 $\log_{10}$, or 1.0 $\log_{10}$, so as to thereby maintain a reduced viral load in the subject.

In another embodiment, the invention provides a method of reducing viral load in an HIV-1-infected subject, which comprises (a) determining that the subject is infected with a CCR5-tropic HIV-L strain; and (b) administering to the subject an effective HIV-1 viral load reducing dose of a CCR5 receptor antagonist which is selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating 3-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:Hu-PRO140 (mut B+D+I)-VH (ATCC Deposit Designation PTA-4099). In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098)

In an embodiment of the above-described method, the CCR5 receptor antagonist achieves an average maximum decrease of viral load in the subject of up to 2.5 $\log_{10}$ by about day nine or day ten following administration. In another embodiment of the method, the CCR5 receptor antagonist achieves an HIV RNA reduction of from 1.20 $\log_{10}$ to 1.83 $\log_{10}$ by about day nine or day ten following administration. In another embodiment of the method, the CCR5 receptor antagonist achieves a $\log_{10}$ HIV RNA change of from about −1.0 to about −1.7 in the subject by about day four to about day ten following administration. In another embodiment of the method, the CCR5 receptor antagonist achieves a greater than ten-fold decrease in HIV RNA in the subject at about ten days following administration. In another embodiment of the method, the CCR5 receptor antagonist achieves a greater than or equal to 1 $\log_{10}$ decrease in HIV RNA in the subject at about day five to about day fifteen following administration. In an embodiment, the CCR5 receptor antagonist is administered intravenously or subcutaneously. In an embodiment, the effective HIV-1 viral load reducing dose of the CCR5 receptor antagonist is selected from 2 mg/kg, 5 mg/kg, 7.5 mg/kg, 10 mg/kg, 15 mg/kg, 20 mg/kg, or 25 mg/kg of the subject's body weight.

In another embodiment, the invention provides a method in which an HIV-infected subject who is to receive a viral load reducing dose of a CCR5 receptor antagonist is tested diagnostically prior to the administration of the CCR5 receptor antagonist to determine if the subject is infected with a CCR5-tropic strain of HIV. In an embodiment, the subject is monitored at predetermined intervals during the administration of the CCR5 receptor antagonist to determine one or more of viral load, CD4 cell count, HIV tropism (e.g., CCR5, CXCR4, or both), HIV resistance, and/or the development of tumors, malignancies, or infections. In an embodiment, the monitoring is carried out every week, every two weeks, every three weeks, once a month, twice a month, once every six weeks, once every two to six months, or two to eight times a year. In an embodiment, the CCR5 receptor antagonist is selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

In an embodiment, the invention further provides a CCR5 receptor antagonist which, when administered to an HIV-infected subject, achieves an average maximum decrease of viral load in the subject of up to 2.5 $\log_{10}$ by about day nine or day ten following administration. In another embodiment, the invention provides a CCR5 receptor antagonist which, when administered to an HIV-infected subject, achieves an HIV RNA reduction of from 1.20 $\log_{10}$ to 1.83 $\log_{10}$ by about day nine or day ten following administration. In another embodiment, the invention provides a CCR5 receptor antagonist which, when administered to an HIV-infected subject, achieves a $\log_{10}$ HIV RNA change of from about −1.0 to about −1.7 in the subject by about day five to about day ten following administration. In an embodiment, the invention provides a CCR5 receptor antagonist which, when administered to an HIV-infected subject, results in a greater than ten-fold decrease in HIV RNA in the subject at about ten days following administration. In an embodiment, the invention provides a CCR5 receptor antagonist which, when administered to an HIV-infected subject, results in a greater than or equal to 1 $\log_{10}$ decrease in HIV RNA in the subject at about day five to about day fifteen following administration. In an embodiment, the CCR5 receptor antagonist of the above is selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In an embodiment, administration of the CCR5 receptor antagonist results in a viral load reduction in the subject that persists for about two to three weeks. In an embodiment, the CCR5 receptor antagonist is administered in a dose selected from 2 mg/kg, 5 mg/kg, 10 mg/kg, 15 mg/kg, 20 mg/kg, or 25 mg/kg of the subject's body weight. In an embodiment, the CCR5 receptor antagonist is administered in a dose selected from 5 mg/kg, 10 mg/kg, 15 mg/kg, or 20 mg/kg of the subject's body weight. In another embodiment, the CCR5 receptor antagonist is administered intravenously or subcutaneously. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

In an embodiment, the invention provides a composition comprising the CCR5 receptor antagonist as described herein and a pharmaceutically acceptable carrier, excipient, or diluent. In an embodiment, the CCR5 receptor anatagonist is the humanized antibody PRO 140 and a single 5 mg/kg dose of PRO 140 administered intravenously to HIV-infected subjects results in a 1.8 $\log_{10}$ mean reduction in HIV RNA in the HIV-1-infected subject.

In another embodiment, this invention also provides a method of reducing viral load in an HIV-1-infected human subject which comprises administering to the subject an effective HIV-1 viral load reducing dose of a CCR5 receptor antagonist, wherein the viral load reducing dose of the CCR5 receptor antagonist results in a suppression of mean viral load by about 1.0 $\log_{10}$ within about five days following administration of the CCR5 receptor antagonist. In one embodiment, the suppression of viral load in the subject persists at or greater than 1.0 $\log_{10}$ reduction for about two to four weeks. In one embodiment, the viral load reducing dose of the CCR5 receptor antagonist is a single dose administered intravenously. In related embodiments, the single intravenous dose of the CCR5 receptor antagonist is selected from 5 mg/kg, 10 mg/kg, 15 mg/kg, 20 mg/kg, or 25 mg/kg of the subject's body weight.

In an embodiment, the viral load reducing dose of the CCR5 receptor antagonist is a multiple dose administered intravenously. In one embodiment, each intravenous dose of the CCR5 receptor antagonist is 5 mg/kg of the subject's body weight. In one embodiment, each intravenous dose of the CCR5 receptor antagonist is 10 mg/kg of the subject's body weight. In one embodiment, each intravenous dose of the CCR5 receptor antagonist is 15 mg/kg of the subject's body weight. In one embodiment, each intravenous dose of the CCR5 receptor antagonist is 20 or 25 mg/kg of the subject's body weight. In one embodiment, the multiple viral load reducing doses of the CCR5 receptor antagonist are administered intravenously at repeated intervals of about every week, about every two weeks, about every three weeks, about every four weeks, about every five weeks, or about every six weeks after administration of a first dose. In one embodiment, each dose of the CCR5 receptor antagonist is administered intravenously at repeated intervals of about every two weeks, about every three weeks, about every four weeks, about once a month, about every five weeks, or about every six weeks, or longer after administration of the first dose. In another embodiment, the viral load reducing dose of the CCR5 receptor antagonist is administered subcutaneously. In one embodiment, the viral load reducing dose of the CCR5 receptor antagonist is administered subcutaneously in multiple doses. In one embodiment, the CCR5 receptor antagonist is administered subcutaneously once a week, twice a week, once every two weeks, twice every two weeks, or once or twice a month, at SC doses described herein.

In accordance with the present invention, the CCR5 receptor antagonist may be selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In one embodiment, the anti-CCR5 receptor monoclonal antibody binds to the same CCR5 epitope as that to which PRO 140 binds. In one embodiment, the anti-CCR5 receptor monoclonal antibody is a humanized, human, or chimeric antibody. In one embodiment, the antibody administered to the subject is the humanized antibody designated PRO 140. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098). In one embodiment, the humanized PRO 140 antibody is modified to increase its serum half-life. In one embodiment, the humanized PRO 140 antibody is modified by pegylation to increase its serum half life. In one embodiment, the present method further comprises co-administering to the subject at least one antiretroviral agent effective against HIV-1. In one embodiment, the antiretroviral agent is a nonnucleoside reverse transcriptase inhibitor (NNRTI), a nucleoside reverse transcriptase inhibitor (NRTI), a protease inhibitor (PI), a fusion inhibitor, or any combination thereof. In one embodiment, the humanized PRO 140 antibody is administered in conjunction with UK-427,857 (maraviroc). In one embodiment, the subject is treatment-naïve. In one embodiment, the subject is treatment-experienced.

In an embodiment of the above-described methods, (a) prior to administering the monoclonal antibody to the subject, the subject has received treatment with at least one additional anti-HIV-1 antiretroviral agent, and/or (b) concurrent with administering the monoclonal antibody, at least one antiretroviral agent is administered to the subject, so as to enhance the reduction of HIV-1 viral load in the subject. In one embodiment, the antiretroviral agent is a nonnucleoside reverse transcriptase inhibitor (NNRTI), a nucleoside reverse transcriptase inhibitor (NRTI), a protease inhibitor (PRI), a fusion inhibitor, or any combination thereof. In one embodiment, the antiretroviral agent is UK-427,857 (maraviroc).

In one embodiment, the present methods further comprise concurrently administering to the subject a non-antibody CCR5 receptor antagonist, which (a) has an effect additive to that of the HIV-1 viral load reducing CCR5 receptor antagonist, or (b) has an effect synergistic to that of the HIV-1 viral load reducing CCR5 receptor antagonist. In one embodiment, the non-antibody CCR5 receptor antagonist is SCH-D, TAK-779, TAK-652, UK-427,857, RANTES, GW873140, or a combination thereof. In one embodiment, the non-antibody CCR5 receptor antagonist is a small organic molecule that competes with SCH-D in binding to the CCR5 receptor. In one embodiment, the non-antibody CCR5 receptor antagonist is a small organic molecule that competes with UK-427,857 in binding to the CCR5 receptor. In an embodiment, the non-antibody CCR5 receptor antagonist is a small organic molecule that competes with TAK-779 in binding to the CCR5 receptor. In one embodiment, the non-antibody CCR5 receptor antagonist is a small organic molecule that competes with TAK-652 in binding to the CCR5 receptor. In one embodiment, the non-antibody CCR5 receptor antagonist is a small organic molecule that competes with GW873140 in binding to the CCR5 receptor. In one embodiment, the antiretroviral agent is a monoclonal antibody that binds CCR5.

In embodiments of the methods of the invention, a viral load-reducing dose is sufficient to achieve in the subject a serum concentration of the antibody of at least 100 to 400 ng/ml. In one embodiment, the doses are sufficient to achieve and maintain in the subject a serum concentration of the antibody of at least 1 µg/ml. In one embodiment, the doses are sufficient to achieve and maintain in the subject a serum concentration of the antibody of about 3 to about 12 µg/ml. In one embodiment, the doses are sufficient to achieve and maintain in the subject a serum concentration of the antibody of at least 5 µg/ml. In one embodiment, the doses are sufficient to achieve and maintain in the subject a serum concentration of the antibody of at least 10 µg/ml. In one embodiment, the doses are sufficient to achieve and maintain in the subject a serum concentration of the antibody of at least 25 µg/ml. In one embodiment, the doses are sufficient to achieve and maintain in the subject a serum concentration of the antibody of at least 50 µg/ml. In one embodiment, the reduction of the subject's HIV-1 viral load is maintained for at least one week. In one embodiment, the reduction of the subject's HIV-1 viral load is maintained for two to three weeks. In one embodiment, the reduction of the subject's HIV-1 viral load is maintained for at least two weeks. In one embodiment, the reduction of the subject's HIV-1 viral load is maintained for at least three weeks. In one embodiment, the reduction of the subject's HIV-1 viral load is maintained for at least four weeks. In one embodiment, the reduction of the subject's HIV-1 viral load is maintained for at least three months. In one embodiment, the reduction of the subject's HIV-1 viral load is maintained for greater than three months.

In another embodiment of the methods of the invention, the subject's HIV-1 viral load is reduced by at least 50% following administration of the CCR5 receptor antagonist or the antibody. In another embodiment, the subject's HIV-1 viral load is reduced by at least 70% following administration of the antibody. In another embodiment, the subject's HIV-1 viral load is reduced by at least 90% following administration of the antibody. In another embodiment, the subject's HIV-1 viral load is reduced by at least 95% following administration of the antibody. In another embodiment, the subject's HIV-1 viral load is reduced by at least 98.5% following administration of the antibody. In another embodiment, the subject's HIV-1 viral load is reduced by at least 99.7% following administration of the antibody.

The invention also provides a method of reducing and maintaining reduced viral load in an HIV-1-infected human subject by multiple dosing of the subject, which comprises (a) administering to the subject a first effective HIV-1 viral load reducing dose of (1) a humanized antibody designated PRO 140, or of (2) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:Hu-PRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099), wherein the first effective HIV-1 viral load-reducing dose results in a 1.8 $\log_{10}$ mean reduction in viral load in the subject by about day 9 or 10 following dosing of the subject; and (b) administering to the subject one or more subsequent effective HIV-1 viral load reducing doses of the humanized antibody designated PRO 140 of (1) or the anti-CCR5 receptor monoclonal antibody of (2) at a time when the viral load in the subject is at or about a 0.7 to 1.5 logic reduction, or a 1.0 $\log_{10}$ reduction, relative to baseline, so as to thereby reduce and maintain the reduction of the subject's viral load by multiple dosing of the subject. In an embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

This invention also provides a method of reducing viral load in an HIV-1-infected human subject by multiple dosing of the subject, which comprises: (a) administering to the subject a first effective HIV-1 viral load reducing dose of a CCR5 receptor antagonist, wherein the first effective HIV-1 viral load-reducing dose results in a viral load decrease of from 1.2 to about 1.83 logic in the subject following dosing of the subject; and (b) administering to the subject one or more subsequent effective HIV-1 viral load reducing doses of the CCR5 receptor antagonist at repeated intervals, such as at a time when the viral load in the subject is at or about a 0.7 to 1.5 $\log_{10}$ reduction, or a 1.0 $\log_{10}$ reduction, so as to thereby reduce the subject's HIV-1 viral load by multiple dosing of the subject. In an embodiment, the first HIV-1 viral load reducing dose is selected from 5 mg/kg, 10 mg/kg, 15 mg/kg, mg/kg, or 25 mg of the subject's body weight. In one embodiment, the one or more subsequent HIV-1 viral load reducing doses are the same as or different from the first dose and are administered once a week, every two weeks, every three weeks, every four weeks, every five weeks, or longer, after the first dose. In one embodiment, the first and subsequent HIV-1 viral load reducing doses are administered intravenously to the subject. In one embodiment, the first and subsequent HIV-1 viral load reducing doses are administered subcutaneously to the subject. In one embodiment, the CCR5 receptor antagonist is the humanized antibody designated PRO 140 or the anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140, (iii) coats CD4+CCR5+ cells in the subject without reducing the number of such cells in the subject, and/or (iv) binds to the subject's CD4+CCR5+ cells without inducing an increase in the subject's plasma concentration of circulating 3-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In an embodiment, the CCR5 receptor antagonist is PRO 140 which comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098). In an embodiment, the CCR5 receptor antagonist is a protein. In an embodiment, the protein CCR5 receptor antagonist is a second antibody which is not PRO 140. In an embodiment, the second antibody CCR5 receptor antagonist is a monoclonal antibody. In one embodiment, the second monoclonal antibody CCR5 receptor antagonist is humanized. In an embodiment, the CCR5 receptor antagonist, e.g., humanized PRO 140 antibody, is co-administered with one or more additional CCR5 receptor antagonists. In an embodiment, the additional CCR5 receptor antagonist is a non-protein, small organic molecule which binds CCR5. In an embodiment, the additional CCR5 receptor antagonist, which is a non-protein, small organic molecule which binds CCR5, does not compete with PRO 140's binding and activity. In another embodiment, at least one antiretroviral agent is concurrently administered to the subject, so as to enhance the reduction of HIV-1 viral load in the subject. In one embodiment, the antiretroviral agent is a nonnucleoside reverse transcriptase inhibitor (NNRTI), a nucleoside reverse transcriptase inhibitor (NRTI), a protease inhibitor (PI), a fusion inhibitor, or any combination thereof.

In accordance with an embodiment of the methods of the present invention, the HIV-1 infected subject is a pregnant woman or a nursing mother.

This invention further provides a CCR5 receptor antagonist which, when administered to an HIV-infected subject, achieves an average maximum decrease of viral load in the subject of at least 1.83 $\log_{10}$ to 2.5 $\log_{10}$ following administration to the subject.

This invention further provides a CCR5 receptor antagonist which, when administered to an HIV-infected subject, achieves a mean viral load reduction of about 1-1.7 $\log_{10}$ by ten days following administration to the subject.

This invention also provides a CCR5 receptor antagonist which, when administered to an HIV-infected subject, results in a suppression of mean viral load by 1.0 $\log_{10}$ at a dose of 5 mg/ml following administration to the subject. In an embodiment, the suppression of viral load in the subject persists at or below a level of reduction of 1.0 $\log_{10}$ for about two to three weeks.

In an embodiment related to the foregoing, the CCR5 receptor antagonist is selected from (a) a humanized antibody designated PRO 140, or (b) an anti-CCR5 receptor monoclonal antibody which (i) binds to CD4+CCR5+ cells in the subject and inhibits fusion of HIV-1 with such cells, (ii) inhibits HIV-1 fusion with CD4+CCR5+ cells with a potency equal or greater than that of PRO 140. (iii) coats CD4+CCR5+ cells in the subject without reducing the number of such cells in the subject, and/or (iv) binds to the subject's CD4+CCR5+ cells without inducing an increase in the subject's plasma concentration of circulating β-chemokines, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant (Cu) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099).

In one embodiment, the CCR5 receptor antagonist is the humanized antibody designated PRO 140. In another embodiment, PRO 140 comprises (i) two light chains, each light chain comprising the light chain variable ($V_L$) and constant ($C_H$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

In an embodiment of the methods described herein, the humanized PRO 140 antibody is pegylated to increase its serum half-life. In an embodiment, the serum half-life of the humanized PRO 140 antibody is from about 72 hours to about 250 hours. In an embodiment, the serum half-life of the humanized PRO 140 antibody is sustained for about 216 to 220 hours.

In an embodiment of the instant methods described herein, the monoclonal antibody is a CCR5 receptor antagonist and is the humanized antibody designated PRO 140, or is an antibody that competes with PRO 140's binding to the CCR5 receptor, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099). In a further embodiment, the monoclonal antibody is a humanized or human antibody that binds to the same epitope as that to which antibody PRO 140 binds. In another embodiment, the monoclonal antibody is the humanized antibody designated PRO 140. In a further embodiment, the monoclonal antibody is the human antibody designated CCR5 mAb004 (Roschke et al., 2004; HGS Press Release, 2004; 2005). In a further embodiment, PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded by the plasmid designated pVg4:HuPRO140 HG2-VH (ATCC Deposit Designation PTA-4098).

In other embodiments of the instant methods, the anti-CCR5 antibody (or CCR5 receptor antagonist) is administered to the subject a plurality of times and each administration of the antibody delivers from 0.01 mg per kg body weight to 50 mg per kg body weight of the antibody to the subject. In another embodiment, each administration of the antibody delivers from 0.05 mg per kg body weight to 25 mg per kg body weight of the antibody to the subject. In a further embodiment, each administration of the antibody delivers from 0.1 mg per kg body weight to 10 mg per kg body weight of the antibody to the subject. In a still further embodiment, each administration of the antibody delivers from 0.5 mg per kg body weight to 5 mg per kg body weight of the antibody to the subject. In another embodiment, each administration of the antibody delivers from 1 mg per kg body weight to 3 mg per kg body weight of the antibody to the subject. In a preferred embodiment, each administration of the antibody delivers about 2 mg per kg body weight of the antibody to the subject.

In yet other embodiments of the methods, the anti-CCR5 antibody or CCR5 receptor antagonist is administered a plurality of times, and a first administration of the antibody is separated from the subsequent administration of the antibody by an interval of less than one week. In another embodiment, the first administration of the antibody is separated from the subsequent administration of the antibody by an interval of at least one week. In a further embodiment, the first administration of the antibody is separated from the subsequent administration of the antibody by an interval of one week. In another embodiment, the first administration of the antibody is separated from the subsequent administration of the antibody by an interval of two to four weeks. In another embodiment, the first administration of the antibody is separated from the subsequent administration of the antibody by an interval of two weeks. In a further embodiment, the first administration of the antibody is separated from the subsequent administration of the antibody by an interval of four weeks. In yet another embodiment, the antibody is administered a plurality of times, and a first administration of the antibody is separated from the subsequent administration of the antibody by an interval of at least one month.

In further embodiments of the methods of the invention, the antibody is administered to the subject via intravenous infusion. In another embodiment, the antibody is administered to the subject via subcutaneous injection. In another embodiment, the antibody is administered to the subject via intramuscular injection.

In another embodiment of the invention, the antibody is administered alone, or in combination with other antiretroviral drugs. For example, the antibody may be administered with a protease inhibitor (e.g., ritonavir (Abbott), or with another CCR5 receptor antagonist, e.g., maraviroc (Pfizer), each used alone or in a fixed-dose combination with the protease inhibitor lopinavir (Kaletra), and others.

In another embodiment of the invention, the antibody is administered alone, or in combination with other CCR5 receptor antagonists that inhibit or block HIV entry. Such CCR5 receptor antagonists may include proteins, such as other monoclonal antibodies, such as, for example, TNX-355 (Genentech/Tanox), or non-proteins, e.g., small organic molecules, such as maraviroc (Pfizer). The antibody of the invention as a CCR5 receptor antagonist may act additively or synergistically with other protein and/or non-protein CCR5 receptor antagonists or with other antiretroviral drugs that target or do not target the CCR5 receptor. According to an embodiment of the invention, a viral load reducing amount of the CCR5 receptor antagonist, e.g., the humanized antibody PRO 140, is used in combination with one or more HIV-1 entry inhibitors or therapeutics, for example, as presented in Table 1. In another embodiment, the HIV-1 entry inhibitor is TNX-355 (Genentech/Tanox), an anti-CD4 humanized antibody, which prevents HIV-1 entry at the post-attachment stage of virus infection. In an embodiment, PRO 140 and TNX-355 are administered to a subject, either at the same time, or sequentially, at different times. Effective doses of the two humanized antibodies may be administered separately or together to a subject, either by the same route of administration, e.g., IV, or by different routes of administration. For a combined effect, one embodiment encompasses the administration of the two humanized antibodies to a subject as separate infusions at predetermined times. Another embodiment encompasses the co-formulation of the two humanized antibodies, which are administered together to a subject as a co-formulation.

Embodiments of the invention encompass single and multiple dosing HIV treatment regimens using the humanized antibody PRO 140. Single dosing regimens encompass, for example, a 5 mg/kg, 10 mg/kg, or 15 mg/kg dose of PRO 140 delivered intravenously to an HIV-infected subject. Multiple dosing regimens are performed to achieve a more prolonged reduction in viral load in an HIV-infected subject for a period of time of about two or three weeks and longer, e.g., one month and longer between doses. The HIV-infected subjects receiving single or multiple doses of PRO 140 may be treatment-naive or treatment-experienced. Without wishing to be bound by theory, it is to be appreciated that multiple dosing of HIV-1 infected subjects is performed with the desire to achieve maximum exposure of drug and maximum durability of response in the subject receiving drug, e.g., a statistically significant decrease in viral load over time, with the fewest number of injections possible.

More specific multiple dosing embodiments of the invention include a 5 mg/kg, 10 mg/kg, 15 mg/kg, mg/kg, or 25 mg/kg dose of the humanized antibody PRO 140 administered intravenously to a subject. This dose is optionally followed by the administration of one or more subsequent doses of PRO 140. For example, subsequent dosing may occur at day 12 after the first dose; at day 14 after the first dose; at day 15 after the first dose; at day 18 after the first dose; at day 20 or 21 after the first dose; at day 30 or 31 after the first dose, or at day 40 or 45 after the first dose. In accordance with the invention, for a multiple dosing regimen, PRO 140 can be administered to a subject at repeated intervals over time, such as for example, about every two weeks, about every three weeks, about every four weeks (once a month), or about every six weeks after the subject receives the first dose. In this way, a patient's HIV viral load may be maintained at a decreased level for a prolonged time period or indefinitely.

Illustratively, in a multiple dosing embodiment, a first dose of PRO 140, e.g., 5 mg/kg, is administered intravenously to a subject, followed by administration of one or more subsequent doses of PRO 140, which can be the same as the first dose, or a higher dose, such as 10 mg/kg, 15 mg/kg, or mg/kg. In another embodiment, a first dose of PRO 140, e.g., 10 mg/kg, is administered intravenously to a subject, followed by administration of one or more subsequent doses of PRO 140, which can be the same as the first dose, or a higher dose, such as 15 mg/kg, 20 mg/kg, 25 mg/kg, or mg/kg. In an embodiment, the subsequent dose is a 5 to 30 mg/kg IV dose. In an embodiment, the subsequent dose is a 5 to 30 mg/kg IV dose delivered about every two weeks (q2 wks), or about every three weeks (q3 wks), or about every two to three weeks, about every four weeks (q4 wks), or about every six weeks (q6 wks). Ideally, re-dosing is performed about every two weeks, about every three weeks, about every four weeks, or longer, in order to minimize or alleviate the potential of a subject to develop resistance to drug (e.g., PRO 140). In an embodiment, a 5 mg/kg IV dose of PRO 140 is administered every two to three weeks (about every 14 to 21 days) to maintain effective antibody coating on target cells. In an embodiment, an intravenous dose of PRO 140, e.g., 2 mg/kg, 5 mg/kg, mg/kg, 15 mg/kg, 20 mg/kg, or 25 mg/kg, is administered at a predetermined time to a patient who is concurrently receiving one or more other antiretroviral drugs. In an embodiment, a first dose of PRO 140, e.g., 5 mg/kg or 10 mg/kg, is administered to a subject, followed by one or more subsequent doses of PRO 140. In an embodiment, a 5 mg/kg, a 10 mg/kg, or a 15 mg/kg intravenous dose of PRO 140 is administered in conjunction with another antiretroviral agent (drug), such as UK-427,857 (maraviroc). As described, the co-administration of antiretroviral compounds may achieve enhanced and/or prolonged reductions in viral load over time.

In various embodiments, a 10 mg/kg dose of PRO 140 is administered to a subject intravenously about every 14-31 days in a multiple dosing regimen. In an embodiment, a 10 mg/kg dose of PRO 140 is administered to a subject intravenously about every 14-15 days, or about every two weeks. In an embodiment, a 10 mg/kg dose of PRO 140 is administered to a subject intravenously about every 20-21 days, or about every three weeks. In another embodiment, a 10 mg/kg dose of PRO 140 is administered to a subject intravenously about every 30-31 days, or about once a month. In an embodiment, a 10 mg/kg dose of PRO 140 is administered to a subject intravenously about every six weeks. In an embodiment, a first 10 mg/kg dose of PRO 140 is administered to a subject, followed by one or more subsequent 5 mg/kg, 10 mg/kg, or 15 mg/kg doses of PRO 140. In an embodiment, a 15 mg/kg dose of PRO 140 is administered to a subject about every three weeks, about every 4 weeks, or about every 6 weeks, or longer.

In another embodiment encompassing a multiple dosing regimen, the humanized antibody PRO 140 is administered subcutaneously to a subject. In one embodiment, multiple subcutaneous doses of PRO 140 are administered to a subject as an HIV treatment regimen one or more times per week. In an embodiment, one SC injection of PRO 140 per week is administered to an HIV-infected subject. In an embodiment, two or more SC injections of PRO 140 per week are administered to an HIV-infected subject. In an embodiment, three SC injections of PRO 140 per week are administered to an HIV-infected subject. In an embodiment, weekly 2 or 3×1.0 ml doses of PRO 140 are administered to an HIV-infected subject. In an embodiment, weekly 2 or 3×1.2 ml doses of PRO 140 are administered to an HIV-infected subject. In an embodiment, a SC dose of 100-500 mg is administered to an HIV-infected subject. In an embodiment a SC dose of 100, 150, or 180 mg is administered to an HIV-infected subject. In an embodiment, a SC dose of 300, 350, or 360 mg is administered to an HIV-infected subject. In an embodiment, a 100 mg, 150 mg, 180 mg, 300 mg, 350, or 360 mg dose of PRO 140 is administered SC to an HIV-infected subject on a weekly basis, or every two, four, or six weeks. In an embodiment, a dose of PRO 140, e.g., 100 mg, 150 mg, 180 mg, 300 mg, 350, or 360 mg, is administered SC to an HIV-infected subject as a single dose or multiple doses, e.g., two or three doses, one or multiple times. The SC injection times may vary and may encompass, for example, two or three times per week, or every two, four, or six weeks. In an embodiment, the 2 mg/kg to 10 mg/kg SC dose of PRO 140 is injected into the HIV-infected subject once, twice, or three times per week. In an embodiment, one or two SC injections of PRO 140 every week or every two weeks are administered to an HIV-infected subject. In an embodiment, one, two, or three SC injections of PRO 140 per month are administered to an HIV-infected subject. In one embodiment, PRO 140 is administered as a SC infusion of 162 mg for three doses, e.g., three single doses administered on days 1, 8 and 15. In one embodiment, PRO 140 is administered as a SC infusion of 324 mg for three doses, e.g., three single doses administered on days 1, 8, and 15. In an embodiment, PRO 140 is administered as a SC infusion of 324 mg for two doses, e.g., two single doses administered on days 1 and 15. A SC infusion may constitute the injection of a parenteral solution of PRO 140 subcutaneously into the patient over a predetermined period of time; thereafter, endpoint analyses may be performed. In an embodiment, each SC dose of PRO 14 is in a volume of 1-1.5 ml per injection, in a volume of 1-1.2 ml per injection, or in a volume of ≤1 ml per injection. In an embodiment, one or more 2 mg/kg SC doses of PRO 140 are administered to a subject every week or every two weeks.

In an embodiment, one or more 3 mg/kg SC doses of PRO 140 are administered to a subject every week or every two weeks. In an embodiment, one or more 4 mg/kg SC doses of PRO 140 are administered to a subject every week or every two weeks. In an embodiment, one or more 5 mg/kg SC doses of PRO 140 are administered to a subject every week or every two weeks. In an embodiment, one or more 7.5 mg/kg SC doses of PRO 140 are administered to a subject every week or every two weeks. In an embodiment, a subcutaneous dose of PRO 140 is administered to a patient who is concurrently receiving one or more other antiretroviral drug medications. The one or more other antiretroviral drug medications are administered to the patient according to a predetermined time schedule. The patient may be receiving the one or more other antiretroviral drug medications, for example, one or more times per day or per week, or one or more times per two weeks, etc. In an embodiment, the other antiretroviral drug medication is UK-427,857 (maraviroc).

In another embodiment, the invention provides a long-acting home therapy for chronic use to treat HIV infection. In accordance with the invention, the potent and prolonged single dose antiviral effects and the high aqueous solubility of PRO 140 as an exemplary CCR5 receptor antagonist are advantageous to home therapy. Preclinical studies of PRO 140 support its clinical use, a repeat SC dosing schedule and good bioavailability. Illustratively, q1 week and q2 week SC dosing regimens may drop the HIV viral load by 1.5-2 $\log_{10}$ in patients undergoing SC administration of PRO 140. In an embodiment, the home therapy comprises self-injection.

In an embodiment, an HIV-1 infected subject is able to self-administer subcutaneously a prepackaged dose of PRO 140. In an embodiment, the prepackaged dose of PRO 140 is provided in one or more pre-filled syringes, which may be supplied in a kit that includes instructions for use. In an embodiment, PRO 140 may be supplied for use in an automated or preprogrammed injection device. In an embodiment, each prepackaged subcutaneous dose of PRO 140 is 2 mg/kg to 10 mg/kg of the subject's body weight. In an embodiment, each prepackaged subcutaneous dose of PRO 140 is one-half of the total dose, (e.g., 2 mg/kg to 10 mg/kg of the subject's body weight), for twice per day or twice per week delivery. In an embodiment, each prepackaged subcutaneous dose of PRO 140 is one-third of the total dose, (e.g., 2 mg/kg to 10 mg/kg of the subject's body weight), for three times per day or three times per week delivery. In an embodiment, the prepackaged subcutaneous dose of PRO 140 is 2 mg/kg, 3 mg/kg, 4 mg/kg, 5 mg/kg, 7.5 mg/kg, 10 mg/kg, 15 mg/kg, or 20 mg/kg of the subject's body weight. In an embodiment, one or more pre-filled syringes containing a subcutaneous dose of PRO 140 is/are contained in a kit, such that the subject is able to self-inject the dose of PRO 140 at predetermined time intervals. In an embodiment, two or more pre-filled syringes, each containing a subcutaneous dose of PRO 140 are contained in a kit, such that the subject is able to self-inject two or more doses of PRO 140 at predetermined time intervals. In another embodiment, PRO 140 is admixed with other antiretroviral drugs, e.g., as a cocktail, in a pre-filled syringe or automated device for subcutaneous administration. In another embodiment, separate pre-filled syringes or automated devices containing the appropriate viral load reducing amounts of PRO 140 and one or more pre-filled syringes or injection devices containing one or more other antiretroviral drugs are supplied in a kit for self-administration, along with instructions for use. In an embodiment, PRO 140 is administered via an auto-injector device or a slow infusion device for subcutaneously delivery. In an embodiment, the auto-injector device or slow infusion device is for one time use. In an embodiment, the slow infusion device may deliver PRO 140 subcutaneously to a subject in a time period of approximately 2, 3, 4, 5, 6, 7, 8, 9, or 10 minutes. In an embodiment, PRO 140 is delivered subcutaneously to a subject at a dose of 162 mg or 324 mg weekly or biweekly, for example at days 1, 8 and 15, or at days 1 and 15.

In all of the above-described multiple dosing regimens, viral load can be monitored at periodic intervals as part of treating a subject with a CCR5 receptor antagonist such as the humanized antibody PRO 140. In an embodiment, re-dosing with the CCR5 receptor antagonist, e.g., PRO 140, is performed, or subsequent doses of the CCR5 receptor antagonist, e.g., PRO 140, are administered, when the subject's HIV RNA decrease (viral load reduction) is determined to be of a value that indicates or warrants further dosing of the subject. Illustratively, subsequent dosing of the CCR5 receptor antagonist, e.g., PRO 140, could be administered to a subject whose viral load is $-0.7 \log_{10}$ to $1.5 \log_{10}$ relative to baseline, or $~1 \log_{10}$ relative to baseline, to provide a further reduction in viral load in the subject and to maintain a reduced viral load in the subject.

In an embodiment, a $\geq 1 \log_{10}$ decrease in viral load occurs after about day 5 to about day 10 following administration of PRO 140 to an HIV-1 infected subject. In an embodiment, a $\geq 1 \log_{10}$ decrease in viral load occurs after about day 5 following administration of PRO 140 at a dose of 5 mg/kg to an HIV-1 infected subject. In an embodiment, the maximum effect of the administration of PRO 140 to an HIV-1-infected subject is on day 10 following administration (e.g., a 5 mg/kg single dose of PRO 140). In an embodiment, decreased viral load persists in the subject for about two to three weeks post dose. In an embodiment, the amount of virus in a subject who is undergoing treatment with PRO 140 and is receiving a 5 mg/kg dose of PRO 140 is <400 copies by about day 5 to about day 15 following treatment with PRO 140.

It will be understood by the skilled practitioner that if an anti-PRO 140 antibody response should be detected in a subject, such a response can be assessed to determine if it is a neutralizing antibody response. If a PRO 140 neutralizing antibody response is detected in a subject treated with PRO 140, then the subject's treatment regimen may be modified and/or another antiretroviral drug treatment course, or treatment combination, may be used or continued in the subject. If the anti-PRO 140 antibody response is determined not to be a neutralizing response, and the subject's viral load is successfully reduced by PRO 140 treatment, the current PRO 140 dosing regimen may be maintained or modified as determined by the skilled medical practitioner, and the subject may be further monitored periodically thereafter.

Another embodiment of the invention encompasses a method of preventing or reducing the transmission of HIV-1 infection from an HIV-1-infected nursing mother to her nursing child. In accordance with this method, an HIV-1-infected mother is treated therapeutically with PRO 140 before giving birth, after giving birth, or both before and after giving birth by one of the above-described dosing regimens. In accordance with this method, the transmission of HIV-1 from mother to child through breast milk while the child is nursing is prevented or significantly reduced. Pediatric treatment using PRO 140 is therefore envisioned in accordance with this invention. In an embodiment, a nursing child is also prophylactically treated with PRO 140 to prevent HIV-1 infection through the breast milk of an HIV-1-infected mother. In an embodiment, the therapeutic treatment of a nursing mother with PRO-140 prevents transmission of virus to her child through the breast milk. In an embodiment, the prophylactic treatment of the nursing child with PRO-140 prevents HIV-1 infection of the child through its mother's breast milk. In an embodiment, a combination of therapeutic treatment of a nursing mother with PRO-140 and prophylactic treatment of her nursing child with PRO-140 prevents transmission of virus from mother to child through breast milk and concomitantly protects the child from HIV-1 infection. In an embodiment, treatment with PRO 140 may be continued in the children of HIV-infected mothers. In an embodiment, pediatric treatment with PRO 140 may decrease viral load and inhibit infection of HIV in HIV-infected babies (e.g., following birth to age 3), young children (e.g., ages 3-10) pre-teens (e.g., ages 10-12); teens/adolescents (e.g., ages 13-17) and young adults (e.g., ages 18-25). Pediatric use may include both treatment-experienced and treatment naïve pediatric patient populations.

Another embodiment of the present invention embraces a method in which HIV-1 infected patients who are undergoing surgical procedures and have been required to suspend or cease some or all of their prescribed anti-HIV-1 (antiretroviral) drugs and medications for a time before, during, or after surgery may be treated with PRO 140 in the interim time period to maintain their reduction of viral load. In an embodiment, the HIV-1 infected patient is treated with an intravenous dose of PRO 140 during surgery. In an embodiment, the HIV-1 infected patient is treated with an intravenous dose of PRO 140 before surgery. In an embodiment, the HIV-1 infected patient is treated with an intravenous dose of PRO 140 directly after surgery and during the recovery period until the patient is able to resume his or her prescribed antiretroviral drug medication(s). In an embodiment the intravenous dose of PRO 140 administered to the patient before, during, or after surgery is 5 mg/kg of the patient's body weight. In an embodiment the intravenous dose of PRO 140 is administered to the patient before or after surgery is 10 mg/kg of the patient's body weight. In an embodiment the intravenous dose of PRO 140 is administered to the patient before or after surgery is 15 mg/kg of the patient's body weight. In another embodiment, the HIV-1 infected patient is treated with one or multiple subcutaneous doses of PRO 140 directly after surgery and during the recovery period until the patient is able to resume his or her prescribed antiretroviral drug medication. In an embodiment the subcutaneous dose of PRO 140 administered to the patient either before or after surgery is, for example, 2-10 mg/kg of the patient's body weight, administered to the patient weekly or every two weeks, for example.

In related, additional embodiments of the methods described herein, the CCR5 receptor antagonist is administered a plurality of times and each administration of the CCR5 receptor antagonist delivers from 0.5 mg to 2,500 mg of the antagonist to the subject. In another embodiment, each administration of the CCR5 receptor antagonist delivers from 5 mg to 1,250 mg of the antagonist to the subject. In yet another embodiment, each administration of the CCR5 receptor antagonist delivers from 5 mg to mg of the antagonist to the subject. In a further embodiment, each administration of the CCR5 receptor antagonist delivers from 50 mg to 1,250 mg of the antagonist to the subject. In a still further embodiment, each administration of the CCR5 receptor antagonist delivers from 200 mg to 800 mg of the antagonist to the subject. In another embodiment, each administration of the CCR5 receptor antagonist delivers from 300 mg to 600 mg of the antagonist.

As described herein, according to the present invention, the humanized antibody PRO 140 may be administered in conjunction with one or more non-antibody, small molecule compounds for enhanced and prolonged viral load reduction. In an embodiment, the one or more non-antibody, small molecule compound is a CCR5 receptor antagonist. Illustratively, the non-antibody CCR5 receptor antagonist is a small organic molecule. In another embodiment, the CCR5 receptor antagonist is selected from the group consisting of SCH-D, UK-427,857, TAK-779, TAK-652, GW873140 and RANTES. In a further embodiment, the CCR5 receptor antagonist is an agent that competes with SCH-D's binding to the CCR5 receptor. In a still further embodiment, the CCR5 receptor antagonist is an agent that competes with UK-427,857's binding to the CCR5 receptor. In another embodiment, the CCR5 receptor antagonist is an agent that competes with TAK-779's binding to the CCR5 receptor. In yet another embodiment, the CCR5 receptor antagonist is an agent that competes with TAK-652's binding to the CCR5 receptor. In a further embodiment, the CCR5 receptor antagonist is an agent that competes with GW873140's binding to the CCR5 receptor.

Because of their rapid clearance, small-molecule CCR5 receptor antagonists require at least daily or twice-daily dosing in order to maintain selective pressure on the virus. Table 3 summarizes the dosing regimens employed with various small-molecule CCR5 antagonists currently undergoing clinical trials. In one embodiment of the present methods, the CCR5 receptor antagonist is administered orally to the subject at least once per day. In another embodiment, the CCR5 receptor antagonist is administered orally to the subject once or twice per day. In a further embodiment, the CCR5 receptor antagonist is administered orally three or fewer times per day.

TABLE 3

Dosing regimens of small-molecule CCR5 receptor antagonists undergoing clinical trials

| Compound | Dosage[a] | Clinical Trial |
|---|---|---|
| SCH-D | 5-15 mg daily | Phase II |
| UK-427,857 | 300 mg daily or twice daily | Phase II and III |
| GW873140 | 50-1200 mg once daily, or 200-800 mg daily or twice daily | Phase II |

Dosages are indicated for the CCR5 antagonists at www.clinicaltrials.gov web site sponsored by the National Institute of Allergy and Infectious Diseases (NIAID). Dosage information for GW873140 was obtained from Demarest et al. (2004).

Additionally, one embodiment of the instant methods further comprises administering to the subject at least one anti-HIV-1, antiretroviral agent. Since the approval of the nucleoside-analog reverse transcriptase inhibitor (NRTI) AZT (zidovudine) in 1987, the HIV-1 armamentarium has grown to at least 21 drugs and prodrugs representing 4 treatment classes: eight NRTIs, three non-nucleoside reverse transcriptase inhibitors (NNRTIs), nine protease inhibitors (PIs), and one fusion inhibitor (FI) (see Table 4). In another embodiment, the antiretroviral agent is a nonnucleoside reverse transcriptase inhibitor (NNRTI), a nucleoside reverse transcriptase inhibitor (NRTI), a protease inhibitor (PI), a fusion inhibitor, or any combination thereof. In further embodiments, the at least one antiretroviral agent is one of the agents listed in Table 4 or any combination of these agents. Various antiretroviral agents are marketed in combinations (see Table 5 for such combinations and dosing regimens) for more efficacious therapy. In embodiments of the present methods, antiretroviral agents are administered to the subject in amounts shown in Table 5. In another embodiment, the antiretroviral agent is a NNRTI or a PI.

In some embodiments of the instant invention, the subject is treatment-naïve, i.e., the subject has not previously undergone treatment with any anti-HIV-1, antiretroviral agents. In other embodiments, the subject is treatment-experienced, i.e., the subject has undergone, and/or is undergoing, treatment with one or more anti-HIV-1, antiretroviral agents, such as one or more agents listed in Table 4. In a particular embodiment, the instant methods are used in a program of combination therapy for treating HIV-1 infection, wherein an anti-CCR5 mAb and a non-antibody CCR5 antagonist are administered in combination with one or more antiretroviral agents to a subject in need of such treatment.

TABLE 4

Approved HIV-1 inhibitors

| Inhibitor | Manufacturer |
|---|---|
| Nucleoside Reverse Transcriptase Inhibitors (NRTIs) | |
| Retrovir ® (AZT) | GlaxoSmithKline |
| Epivir ® (3TC) | GlaxoSmithKline |
| Emtriva ® (emtricitabine) | Gilead Sciences |
| Hivid ® (ddC) | Hoffmann-La Roche |
| Videx ® (ddI) | Bristol-Myers Squibb |
| Viread ® (tenofovir DF) | Gilead Sciences |
| Zerit ® (d4T) | Bristol-Myers Squibb |
| Ziagen ® (abacavir) | GlaxoSmithKline |
| Non-nucleoside Reverse Transcriptase Inhibitors (NNRTIs) | |
| Rescriptor ® (delavirdine) | Pfizer |
| Sustiva ® (efavirenz) | Bristol-Myers Squibb |
| Viramune ® (nevirapine) | Boehringer Ingelheim |
| Protease Inhibitors (PIs) | |
| Agenerase ® (amprenavir) | GlaxoSmithKline/Vertex |
| Aptivus ® (tipranavir)[a] | Boehringer Ingelheim |
| Crixivan ® (indinavir) | Merck & Co. |
| Invirase ® (saquinavir) | Hoffmann-La Roche |
| Lexiva ® (fosamprenavir) | GlaxoSmithKline/Vertex |
| Lopinavir[b] | Abbott Laboratories |
| Norvir ® (ritonavir) | Abbott Laboratories |
| Reyataz ® (atazanavir) | Bristol-Myers Squibb |
| Viracept ® (nelfinavir) | Pfizer |
| Fusion Inhibitors (FIs) | |
| Fuzeon ® (T-20) | Trimeris/Hoffmann-La Roche |

[a]To be co-administered with ritonavir to boost therapeutic levels of Aptivus ®.
[b]Sold only in combination with ritonavir under the trade name Kaletra ®.

TABLE 5

Dosing regimens of marketed HIV-1 antiviral agents

| Generic Name | Brand/other Name | Dosage* | Formulation | Manufacturer | Approval date |
|---|---|---|---|---|---|
| *Nonnucleoside Reverse Transcriptase Inhibitors (NNRTIs)* | | | | | |
| Delavirdine | Rescriptor, DLV | 400 (4 × 100 or 2 × 200) mg tid | Tablet | Pfizer | Apr. 04, 1997 |
| Efavirenz | Sustiva, EFV | 600 mg qd | Tablet | Bristol-Myers Squibb | Sep. 17, 1998 |
| Nevirapine | Viramune, NVP | 200 mg bid (qd first 2 wks of Rx) | Tablet | Boehringer Ingelheim | Jun. 21, 1996 |
| *Nucleoside Reverse Transcriptase Inhibitors (NRTIs)* | | | | | |
| Abacavir | Ziagen, ABC | 600 (2 × 300) mg qd or 300 mg bid | Tablet | GlaxoSmithKline | Dec. 17, 1998 |
| Abacavir, Lamivudine | Epzicom | **600/300 mg qd | Tablet | GlaxoSmithKline | Aug. 02, 2004 |
| Abacavir, Lamivudine, Zidovudine | Trizivir | **300/150/300 mg qd | Tablet | GlaxoSmithKline | Nov. 14, 2000 |
| Didanosine | Videx, ddI, Videx EC | 400 mg qd (≥60 kg) or 250 mg qd (<60 kg) | Delayed-release Capsule | Bristol-Myers Squibb | Oct. 09, 1991; Oct. 31, 2000 (EC) |
| Emtricitabine | Emtriva, FTC, Coviracil | 200 mg qd | Capsule | Gilead Sciences | Jul. 02, 2003 |
| Emtricitabine Tenofovir DF | Truvada | **200/300 mg qd | Tablet | Gilead Sciences | Aug. 02, 2004 |
| Lamivudine | Epivir, 3TC | 300 mg qd or 150 mg bid | Tablet | GlaxoSmithKline | Nov. 17, 1995 |
| Lamivudine, Zidovudine | Combivir | **150/300 mg bid | Tablet | GlaxoSmithKline | Sep. 27, 1997 |
| Stavudine | Zerit, d4T | 40 mg bid (≥60 kg) or 30 mg bid (<60 kg) | Capsule | Bristol-Myers Squibb | Jun. 24, 1994 |
| Tenofovir DF | Viread, TDF | 300 mg qd | Tablet | Gilead Sciences | Oct. 26, 2001 |
| Zalcitabine | Hivid, ddC | 0.750 mg tid | Tablet | Hoffmann-La Roche | Jun. 19, 1992 |
| Zidovudine | Retrovir, AZT, ZDV | 300 mg bid or 200 (2 × 100) mg tid | Tablet or Capsule | GlaxoSmithKline | Mar. 19, 1987 |
| *Protease Inhibitors (PIs)* | | | | | |
| Amprenavir | Agenerase, APV | 1200 (8 × 150) mg bid | Capsule | GSK, Vertex | Apr. 15, 1999 |
| Atazanavir | Reyataz, ATV | Naïve pts: 400 (2 × 200) mg qd Salvage: 300 (2 × 150) mg qd w/ ritonavir 100 mg qd | Capsule | Bristol-Myers Squibb | Jun. 20, 2003 |
| Fosamprenavir | Lexiva, FPV | 1400 (2 × 700) mg bid | Tablet | GSK, Vertex | Oct. 20, 2003 |
| Indinavir | Crixivan, IDV | 800 (2 × 400) mg tid | Capsule | Merck | Mar. 13, 1996 |
| Lopinavir, Ritonavir | Kaletra, LPV/r | **400/100 (3 × 133.3/33.3) mg bid | Capsule | Abbott Laboratories | Sep. 15, 2000 |
| Nelfinavir | Viracept, NFV | 1250 mg (5 × 250 or 2 × 625) bid or 750 mg (3 × 250) tid | Tablet | Agouron | Mar. 14, 1997 |
| Ritonavir | Norvir, RTV | 600 (6 × 100) mg bid | Capsule | Abbott Laboratories | Mar. 01, 1996 |
| Saquinavir | Fortovase, SQV Invirase | 1200 (6 × 200) mg tid 1000 (5 × 200) mg bid w/ritonavir 100 mg bid | Capsule Capsule | Hoffmann-La Roche Hoffmann-La Roche | Nov. 07, 1997 Dec. 06, 1995 |
| Tipranivir | Aptivus | 1000 (2 × 250) mg bid w/ ritonavir (2 × 100) mg bid | Capsule | Boehringer Ingelheim | Jun. 23, 2005 |
| *Fusion Inhibitors (FIs)* | | | | | |
| Enfuvirtide | Fuzeon, T-20 | sc: 90 mg (1 ml) bid | Reconstituted solution | Hoffmann-La Roche, Trimeris | Mar. 13, 2003 |

*Adult doses unadjusted for combination therapies; Route of administration: po unless otherwise indicated
**Combination therapies administered in a single formulation Legend:
qd = once daily
bid = twice daily
tid = three times daily
po = oral administration
sc = subcutaneous administration Diagnostic assessment of subjects undergoing treatment with PRO 140, alone or in combination with other antiretrovirals, including other CCR5 receptor antagonists, are encompassed by this invention. In an embodiment, a subject to be treated with PRO 140 is tested prior to treatment to assess the subject's HIV tropism. Tropism refers to the affinity of a virus for a specific co-receptor on a target cell. The subject may be treatment-experienced or treatment-naive. Viral tropism may be assessed or screened by procedures known in the art, such as the Trofile™ Assay (Monogram Biosciences, South San Francisco, Calif.), by way of nonlimiting example, which can provide an HIV profile for a subject, i.e., the strain of virus (R5, X4, or D/M (dual/mixed (R5/X4)) that infects the subject. A subject determined to be infected with CCR5-tropic HIV-1 may then undergo treatment with PRO 140. An embodiment of the invention is therefore directed to a method of treating an HIV-1-infected subject with PRO 140 to reduce viral load in the subject, wherein the subject is diagnostically determined to be infected with CCR5-tropic HIV-1 prior to treatment, and then is treated with PRO 140 in accordance with any of the treatment and dosing methods described herein. In an embodiment, a subject is screened for CCR5 viral tropism about one to six weeks before treatment with PRO 140. In an embodiment, a subject is screened for CCR5 viral tropism about three to six weeks before treatment with PRO 140. In an embodiment, a subject is screened for CCR5 viral tropism about two to five weeks before treatment with PRO 140. In an embodiment, a subject is screened for CCR5 viral tropism about a month to a month and a half before treatment with PRO 140. In an embodiment, the subject is infected with CCR5-tropic HIV-1. In an embodiment, the subject is infected with CCR5-tropic HIV-1, with undetectable levels of either CXCR4 virus or mixed virus types.

In another embodiment, a subject is monitored and screened at repeated intervals during the course of treatment with PRO 140 to determine HIV tropism according to procedures known and used by those skilled in the art. In this way, a subject's drug regimen (e.g., dosing and/or co-administration of other antiretrovirals with PRO 140) can be adjusted or modified as necessary or required according to the subject's virus tropism profile over time. In an embodiment, the subject is determined to be infected with CCR5 tropic HIV-L prior to treatment with PRO 140, with or without other antiretrovirals. Illustratively, monitoring of viral tropism in a subject who is being treated with PRO 140, alone or in combination with other antiretrovirals, may be maintained for a period of six months, one year, two years, three years, four years, five years or longer, as necessary, after treatment is begun. In an embodiment, monitoring a subject for a change in viral tropism may be correlated with other parameters, such as CD4 cell count and viral load. For example, a change in treatment may not be warranted if a change in tropism in a subject undergoing treatment occurs in the absence of any effects on viral load or CD4 cell count in that subject. In addition, a relative increase in X4 virus versus an absolute increase in X4 virus in a patient being treated can be assessed to determine optimization or assessment of a subject's HIV treatment regimen. A relative increase in X4 tropic virus may reflect an increased chance of detection, and may not be as significant if observed during monitoring as an absolute increase in X4 tropic virus, since an absolute increase in X4 tropic virus may reflect a potentially preferential expansion of the X4 virus population in the subject. One skilled in the art will further appreciate that if a subject's CCR5-tropic HIV infection is being inhibited and viral load is being reduced by the use of a CCR5 receptor antagonist, an increase in the detection of X4 virus, if present, might be expected, even in the absence of any absolute increase in the amount of X4 virus, as a result, for example, of depletion of CCR5-tropic HIV. (Report of an FDA/FCHR Joint Public Meeting, May 31, 2006, Forum for Collaborative HIV Research, Apr. 24, 2007). Thus, virus tropism monitoring should be conducted with such outcomes in mind.

In an embodiment, a subject undergoing treatment with PRO 140, alone or in combination with other antiretroviral drugs, is tested for HIV drug resistance at predetermined intervals during the course of treatment. A non-limiting example of a widely used phenotypic HIV drug resistance test is the PhenoSense™ HIV assay (Monogram Biosciences, Inc.), which measures the sensitivity of a virus to antiretroviral drugs. For example, it has been found that the in vitro susceptibility data obtained in the PhenoSense™ HIV Entry Assay is in good agreement with data obtained from testing the same patient-derived viral envelopes in PBL. Thus, this assay, or similar assays, may be used as a primary screen for testing patient samples for resistance to an antiretroviral CCR5 entry inhibitor. A clinician or practitioner is able to determine the level of susceptibility that a person has to each antiretroviral drug in order to design an individualized treatment regimen. In addition, such resistance testing and assessment may be continued in a subject receiving PRO 140 as a treatment regimen, alone or in combination with other antiretroviral drugs, to provide follow-up of the treated subjects at predetermined intervals.

In an embodiment, subjects who are undergoing treatment with PRO 140, alone, or in combination with other antiretroviral drugs, which may include other CCR5 receptor antagonists, are monitored for the development of tumors, e.g., lymphomas and sarcomas, and malignancies at repeated intervals. Without limitation, such intervals may be established to be, for example, once a month, twice a month, once every three weeks, once every six weeks, once every two to six months, or two to six times a year. In an embodiment, subjects who are undergoing treatment with PRO 140, alone or in combination with other antiretroviral drugs which may include other CCR5 receptor antagonists, are monitored for the development of infections (bacterial, viral, opportunistic, etc.). Monitoring of subjects receiving treatment with one or more CCR5 receptor antagonists may include assessment, at the same or at different times, of, for example, virus tropism changes, viral resistance, viral load (HIV RNA levels), CD4 cell count and tumor/malignancies, etc., at repeated intervals during the treatment, e.g., on a monthly basis, every six weeks, every eight weeks, every ten weeks, every twelve weeks, or 2-3 times per year. Such assessments further involve the storage of baseline samples, e.g., serum, taken from the subject prior to and/or at the time of beginning a treatment regimen. Additionally, molecular clonal analysis of the virus population(s) in a subject at baseline may be assessed using methods known and practiced in the art. In this way it can be determined that any tropism change in a subject's virus population (e.g., a CXCR4 variant or duall-mixed virus) emerged from a pre-existing reservoir in the subject not detected at baseline and not from a co-receptor use change in the subject. For each of the above embodiments directed to follow-up, monitoring and periodic screening of subjects undergoing treatment for HIV infection, those skilled in the art will be able to determine the appropriate time intervals in which such follow-up, monitoring and screening assessments should be made.

In accordance with the various methods and embodiments of the present invention, it will be appreciated that the humanized anti-CCR5 monoclonal antibody PRO 140 complements small molecule CCR5 antagonists in that PRO 140 binds a distinct site on CCR5, possesses a distinct pattern of viral resistance, synergizes with small molecule drugs, blocks HIV without significant interference with CCR5 chemokine binding in vitro, exhibits a potential for improved tolerability, enables infrequent dosing, is not expected to be involved in drug-drug or food interactions and is well tolerated in human subjects based on preclinical studies as described hereinbelow. Thus. PRO 140 is advantageously used alone or in combination with other antiretroviral drugs or agents in methods of treating HIV infection and in methods of reducing viral load in an HIV infected patient.

The present invention encompasses products and methods comprising the humanized anti-CCR5 monoclonal antibody PRO 140 for indications involving treatment-experienced, HIV-1 infected patients who have evidence of viral replication. In an embodiment, the treatment-experienced, HIV-1 infected patients are adult patients infected with only CCR5-tropic HIV-1 detectable. In an embodiment, the treatment-experienced, HIV-1 infected patients are adult patients infected with only CCR5-tropic HIV-1 detectable, who have evidence of viral replication and HIV-1 strains resistant to multiple antiretroviral agents. In an embodiment, the humanized anti-CCR5 monoclonal antibody PRO 140 is used in combination with other antiretroviral agents.

A method of reducing viral load in an HIV-1-infected human subject which comprises subcutaneously administering to the subject an effective HIV-1 viral load reducing dose of a CCR5 receptor antagonist comprising (a) a humanized antibody designated PRO 140, or (b) an anti-CCR5 receptor monoclonal antibody which inhibits HIV-L fusion with CD4+CCR5+ cells, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099), wherein the viral load reducing dose achieves an HIV RNA reduction of from about 0.99 up to about 3.5 $\log_{10}$ in the subject following administration of the effective HIV-1 viral load reducing dose.

In an embodiment the viral load reducing dose of the CCR5 receptor antagonist is about 162 mg or about 324 mg.

In an embodiment the viral load reducing dose of the CCR5 receptor antagonist achieves a $\log_{10}$ HIV RNA change of from about −1.0 to about −1.65 in the subject following administration of the CCR5 receptor antagonist.

In an embodiment the reduction of from about 0.99 up to about 3.5 $\log_{10}$ in HIV RNA persists in the subject for about ten days to about three weeks following administration of the CCR5 receptor antagonist.

In an embodiment the HIV RNA reduction occurs by about day 9 to about day 15 after administering to the subject the effective HIV-1 viral load reducing dose.

In an embodiment the viral load reducing doses of the CCR5 receptor antagonist are administered at repeated intervals of about every week after administration of a first dose.

In an embodiment the viral load reducing dose of the CCR5 receptor antagonist is 162 mg which is administered at intervals of about every week after administration of a first dose and which reduces viral load by about 0.99 $\log_{10}$.

In an embodiment the viral load reducing dose of the CCR5 receptor antagonist is 324 mg which is administered at intervals of about every week after administration of a first dose and which reduces viral load by about 1.37 $\log_{10}$.

In an embodiment the viral load reducing dose of the CCR5 receptor antagonist is 324 mg which is administered at intervals of about every week for at least two weeks after administration of a first dose and which reduces viral load by about 1.65 $\log_{10}$.

Additional Embodiments of the Invention

Short Term, Interim, or Induction Use:

Either upon initiation of first HIV therapy regimen, or upon switch of therapy (first line to second line, etc.) the objective of antiviral therapy is to maximally suppress viral load as quickly as possible. Use of PRO-140 in combination with other antiretroviral drugs, even for a short period of time (+/−3 months, for example), can help to ensure rapid and full viral suppression to <50 copies (HIV RNA/ml$^3$). Use of PRO-140 could be continued for a minimum of 12 weeks or until full viral suppression (<50 copies) is achieved. Whether dosed once monthly IV or once weekly subcutaneously, PRO-140 used in an induction format can assist in rapidly suppressing viral replication, protecting the susceptibility of concurrent HIV drugs, as well as sensitivity of patient virus to subsequent HIV drugs. Use of PRO-140 in this manner coincides with the current standard of care at the start of HIV therapy, or upon treatment switching, where frequent viral load testing is conducted (up to 1×/week in the first month, and or 1×/month in the first three months), facilitating PRO-140 administration (e.g., monthly) at the time of clinic visits for laboratory testing blood draws.

The concept of induction/maintenance is much like the model often used in cancer of ablation upfront, followed by maintenance (lower/less intensive) chemotherapy for a period thereafter. PRO-140 is used for a short period of time, e.g., 3-6 months, in combination with other antiretrovirals (or alone) in order to rapidly and completely suppress HIV viral replication and stimulate CD4+ cell proliferation. Once desired levels are achieved and confirmed through repeated lab tests (2 viral load tests indicating <50 copies/ml$^3$ and/or >100 CD4+ cell increase), PRO-140 use may be stopped, while patients continue with other antiretroviral agents to maintain these levels of suppression and CD4+ immune system status.

PRO-140 "intensifies" the potency/effectiveness of an antiretroviral regimen for patients who are either new (naive) to therapy or those who are switching therapy due to inadequate virologic or immunologic response to prior therapy. PRO-140 is used in an acute and temporary manner with this approach to achieve a desired result and then cease using it, rather than using it chronically even after an endpoint is met as with most anti-HIV drugs today. Being able to dose PRO-140 once every month is likely to coincide with normal blood draws following HIV therapy initiation or switch.

PRO 140 can be administered to HIV-1 infected patients who are transitioning from one drug regimen to another. PRO 140 can be administered to the patient during the interim time period between one drug regimen and a second drug regimen of different drugs, or different drug combinations, and/or different drug doses, etc. In an embodiment, PRO-140 is safely removed from the combination of anti-HIV drugs used to achieve full suppression once viral load has reached <50 copies following two separate lab tests. In an embodiment, at least two or three active anti-HIV drugs are used in the follow-on (maintenance or subsequent) regimen.

Intermittent Viral Load Detection:

Temporary use of PRO-140 is also appropriate in cases where patients have viral load that is generally suppressed to <50 or <400 copies, but occasionally rises to levels exceeding these thresholds. Use of PRO-140 for one to three months following two viral load tests confirming 'viral escape' may support the patients current HIV therapy and effectively re-suppress viral replication. Use of PRO-140 even in this short term modality may also afford important immune system restoration function in the form of CD4+ proliferation to further improve a patient's clinical status.

Persistent, Low Level Viral Replication:

It is common among treatment experienced patients to see incomplete viral suppression, or stable, low-level viral replication (>400 but <10,000 copies). In such cases, clinicians often allow patients to continue their HIV regimen as long as there is no change in clinical status or CD4+ count. In an embodiment, temporary (+/−3 month, for example) use of PRO-140 may assist clinicians in suppressing viral loads to <50 copies, even in patients who have never reached this objective, with or without changing some/all of the patients' other concurrent anti-HIV medications. Use of PRO-140 even in this short term modality may also afford important immune system restoration function in the form of CD4+ proliferation to further improve patients' clinical status.

Boosting CD4 Count in Patients with CCR5, Dual Mixed, or CXCR4 Tropic Virus:

In treatment experienced patients or patients infected with multi-drug resistant HIV virus, often the primary goal of therapy is not to suppress HIV viral load but to sustain or improve immune system (CD4+ cell) function. Use of PRO-140 in such patients, either alone or in combination with other antiretroviral agents and regardless of HIV virus tropism, may help boost CD4+ cell count and stabilize a patient's clinical status thus reducing the risk of HIV disease progression.

This invention provides a method of sustaining or improving immune system function in a treatment experienced subject or in a subject infected with multi-drug resistant HIV-1 virus to reduce the risk of HIV disease progression which comprises administering to the subject an effective HIV-1 viral load reducing dose of (a) a humanized antibody designated PRO 140, or of (b) an anti-CCR5 receptor monoclonal antibody which inhibits HIV-1 fusion with CD4+CCR5+ cells, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099), wherein the effective HIV-1 viral load-reducing dose achieves an up to 2.5 $\log_{10}$ HIV RNA reduction by about day nine or day ten following administration, so as to reduce the risk of HIV disease progression.

Re-Use or Recycling of PRO-140:

Other entry inhibitors, specifically enfuvirtide, may have residual activity in up to 50% of patients who have documented resistance and treatment failure to that drug. Following discontinuation of enfuvirtide therapy for 60-90 days, genetic mutations in the gp41 envelope region (36-45) appear to revert to wild-type status. Upon re-initiation of enfuvirtide therapy, up to 50% of patients achieve a response in viral load reduction of −1 log which is sustained for at least 6 months. Among patients who reinitiated enfuvirtide therapy and did not respond, resistance mutations in the gp41 envelope region differed from those seen in prior enfuvirtide therapy. In an embodiment PRO-140, which can induce conformational changes in the V3 loop region, may be reintroduced into a patient who may have become treatment resistant or may have experience treatment failure, if such V3 loop conformational changes are found to differ from prior changes upon reintroduction of the drug. Thus, recycling or reuse of PRO-140 encompasses a viable therapeutic approach.

Extracellular Only HIV Regimens:

With the development of numerous anti-HIV compounds whose mechanism of action focuses on prevention of HIV virus entry into the target (CD4+) immune system cells, it may be possible to fully suppress HIV replication by using combinations of such extra-cellularly active drugs alone. This implies the potential for simplified HIV regimens (fewer drugs needed) that block viral entry and "protect" immune system cells. This approach also has the potential to reduce drug interactions, drug related toxicities as well as exacerbation of co-morbidities often seen in HIV patients (hepatitis, etc.).

In an embodiment, the use of PRO-140 with other extracellularly active anti-HIV drugs that target either HIV or host proteins (including gp41 fusion inhibitors, CCR5, CXCR4, gp120 or other moieties) could be sufficient to fully suppress HIV replication in a sustained manner. Accordingly, the administration of PRO 140 would obviate the need for co-administration of NRTIs, nNRTI's, protease inhibitors (PIs) or integrase inhibitors.

Leveraging Synergistic Mechanistic Activity with Protease Inhibitors (PIs):

Evidence exists to support the selective use of HIV viral entry inhibitors with ritonavir boosted protease inhibitors (PIs) to achieve synergistic MOA based activity that results in enhanced viral suppression compared to combinations of anti-HIV drugs from other classes. By preventing HIV viral entry into CD4+ cells, as well as preventing HIV viral expression from CD4+ cells after intracellular incorporation, PRO-140 and PIs may induce greater, and/or more rapid, and/or more complete HIV suppression than does combination of other mechanisms of action. In an embodiment, synergy between PRO 140 and such PIs may permit the preferential use of PRO-140 with PIs, with or without other anti-HIV drugs, to achieve maximal viral suppression and CD4+ proliferation.

Co-Formulation with Other Anti-HIV Drugs:

Based on the above embodiments, as well as current HIV therapies, the co-formulation of PRO-140 with other anti-HIV drugs to result in combined administration is embraced by the invention. Such co-formulation could involve other injectable anti-HIV drugs or oral anti-HIV drugs that are reformulated into parenteral forms.

PRO 140 Use to Impair Viral Fitness and Pathogenicity:

Use of PRO-140 in doses that are lower than therapeutically necessary or that allow less frequent dosing are contemplated in order to exert a selective pressure which forces HIV to mutate and which may reduce overall efficacy of treatment; however, as a result, a virus that is less virulent, less pathogenic or less 'fit', i.e., less capable of replication, may be produced. Such a situation may be suited for patients whose virus has developed resistance to PRO-140, but who are still deriving some type of immunologic benefit or success, e.g., sustained or rising levels of CD4+ cells—also termed discordant response. Accordingly, such patients may thus still derive a benefit from continuing or maintaining PRO-140 therapeutic treatment. A debilitated HIV virus may also be more susceptible to other HIV drugs, thereby improving the other drugs' effects on HIV viral suppression or CD4+ response. Alternatively, PRO 140 may be similarly administered to patients whose previous anti-HIV drug treatment or regimen has led to a discordant response in order to further and beneficially treat the patients harboring an HIV-1 virus that has been debilitated as a result of treatment with other HIV drugs.

This invention provides a method of sustaining viral load in a human subject infected with HIV-1 which has developed resistance to a humanized antibody designated PRO 140 which comprises: administering to the subject a low dose of (a) the humanized antibody designated PRO 140, or of (b) an anti-CCR5 receptor monoclonal antibody which inhibits HIV-1 fusion with CD4+CCR5+ cells, wherein PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPRO140 HG2-VH (ATCC Deposit Designation PTA-4098) or by the plasmid designated pVg4:HuPRO140 (mut B+D+I)-VH (ATCC Deposit Designation PTA-4099), so as to sustain the subject's HIV-1 viral load.

PRO 140 in Immune Cell Mobilization:

Given the early and robust proliferation in CD4+ cells following PRO 140 treatment, PRO-140 may potently affect both active and resting CD4+ cells, as well as other immune system cells, in a manner that is different from other entry inhibitors. In an embodiment, PRO-140 is administered in single or multiple doses to stimulate or accelerate immune system cell proliferation in HIV infected patients, who are naive to HIV therapy, who are currently on therapy, or who have ceased HIV therapy due to virus resistance or other reasons.

The following Experimental Details are set forth to aid in an understanding of the subject matter of this disclosure, but are not intended to, and should not be construed to, limit in any way the claims which follow thereafter.

EXPERIMENTAL DETAILS

Part I

Materials and Methods
Compounds and Monoclonal Antibodies (MAbs):

PRO 140 was prepared by expression in Sp2/0 cells using Hybridoma serum-free medium supplemented with 2 mM L-glutamine (Invitrogen, Carlsbad, Calif.). Bulk mAb was clarified using a 5.0 µm Depth filter (Sartorius, Goettingen, Germany) followed by passage over a 0.2 µm sterilizing grade filter (Sartorius). The mAb was purified by passage first over an affinity column (MabSelect Protein A column. Amersham, Piscataway, N.J.) and then by ion exchange chromatography (SP Sepharose Cation Exchange resin, Amersham). PRO 140 was nanofiltered using a Viresolve™10 Opticap NFP capsule (Millipore, Billerica, Mass.) followed by a 0.2 µm filter and concentrated/diafiltered over disposable TFF cartridges (Millipore). The mAb was then polished over a hydroxyapatite column (Bio-Rad, Hercules, Calif.), concentrated to 10 mg/ml in phosphate-buffered saline and stored at −70° C. or colder prior to use.

RANTES was purchased from R&D Systems (Minneapolis, Minn.). The anti-CCR5 mAb 2D7 was purchased from BD Biosciences (Cat. #555993), and the anti-CCR5 mAb CTC5 was purchased from R&D Systems (Cat. #FABI1802P).

RET Assay:

The HIV-1 RET assay has been described in detail previously (Litwin et al., 1996). Briefly, fluorescein octadecyl ester (F18; Molecular Probes, Eugene, Oreg.; 5 mg/ml in ethanol), was diluted 1:800 in DMEM labeling medium (DMEM; Invitrogen, Carlsbad, Calif.) with 10% fetal bovine serum (FBS; HyClone, Logan, Utah) and adjusted to an $A_{506}$ of 0.34±10%. Octadecyl rhodamine B chloride (R18; Molecular Probes; 10 mg/ml in ethanol) was diluted 1:2050 in labeling medium and adjusted to an $A_{565}$ of 0.52±10%. Both dyes were further diluted 2-fold by addition to cells in T75-cm² flasks. HeLa-Env$_{JRFL}$ and CEM NKR-CCR5 cells were incubated overnight in F18- and R18-containing culture medium, respectively. The following day, medium from HeLa-Env$_{JRFL}$ cells was removed and 10 ml of 0.5 mM EDTA was added and incubated at 37° C. for 5 min. EDTA was removed and the flask was returned to the incubator for another 5 min followed by striking of the flask to dislodge cells. Ten ml of PBS− with 15% FBS were added to the flask and the contents were transferred to a 50-ml conical centrifuge tube. Suspension CEM NKR-CCR5 cells were added directly to a separate 50-ml conical centrifuge tube. Both cell lines were centrifuged at 300×g for 5 min. The supernatant was discarded and cells were resuspended in 10 ml of PBS−/15% FBS. The centrifugation/wash step was repeated twice, after which the cells were counted and concentrations adjusted to 1.5×10⁶ cells/ml. Ten µl of each cell type (15.000 cells) were seeded into wells of a 384-well plate. Inhibitor compounds were added immediately thereafter to bring the final well volume to 40 µl, and the plates were incubated for 4 h at 37° C. Compounds were tested individually and in combination at a fixed molar ratio or mass ratio over a range of serial dilutions. The plates were then read on a fluorescence plate reader (Victor², Perkin Elmer, Boston, Mass.) using the excitation/emission filter combinations shown in Table 6.

TABLE 6

Excitation/emission filter combinations for RET assay

| Scan No. | Excitation wavelength | Emission wavelength |
|---|---|---|
| 1 | 450 nm/50 nm | 530 nm/25 nm |
| 2 | 530 nm/25 nm | 590 nm/35 nm |
| 3 | 450 nm/50 nm | 590 nm/35 nm |

The "% Inhibition" was calculated according to the following formula:

% Inhibition=100×[(Max % RET−% RET for sample well)/(Max % RET−Min % RET)]

Where:
Max % RET=average of % RET values for HeLa and CEM cell combination without added inhibitor; and
Min % RET=average of % RET values for HeLa and CEM cell combination in presence of 500 ng/ml of Leu-3a mAb (an antibody that targets CD4 and fully blocks fusion in the RET assay at this concentration).

Fifty percent inhibition ($IC_{50}$) values were determined by fitting the inhibition data with a non-linear, four-parameter, variable slope equation (GraphPad Prism, 4.02; GraphPad Software, San Diego, Calif.). Upper and lower inhibition values were constrained to 100% and 0%, respectively for curve fitting.

Preparation of PBMCs:
Replication of Authentic HIV-1 is Measured in Activated Peripheral Blood Mononuclear Cells (PBMCs) Using the Monocyte/Macrophage-Tropic HIV-1 Clone, JRFL (HIV-1$_{JRFL}$), for These Studies.

PBMCs are isolated from 4 separate donors (Leukopacks) by centrifugation on a Ficoll gradient. CD8 cells are depleted using RosetteSep CD8 Depletion Cocktail (#15663, StemCell Research, Vancouver, BC). Cells are diluted to 4×10⁶/ml and added in equal parts to three T175-cm² flasks and then stimulated by addition of one of the following media: IL-2 Medium [RPMI 1640 (#10-040-CV, Cellgro, Herndon, Va.), 10% FBS (#35-010-CV), 2 mM L-Glutamine (#25-005-CI), 100 U/ml IL-2 (Sigma, St. Louis, Mo.)]; PHA 5 Medium: [IL-2 Medium with 5 ug/ml Phytohemagglutinin PHA-P (PHA) (#L8754, Sigma, St. Louis, Mo.), filtered]; or PHA 0.5 Medium: [IL-2 Medium with 0.5 ug/ml PHA, filtered]. Each flask receives a total of 50-150 ml of medium. Flasks are incubated for 3 days at 37° C. followed by pooling of the contents prior to use in the infection assay.

Virus Titration:

Serial dilutions of virus are tested in quadruplicate on activated PBMCs ($1.4\times10^5$ PBMC/well). Titration Medium [IL-2 Medium with 100 IU/ml penicillin/streptomycin (#30-002-CI, Cellgro)] is utilized for virus titrations. Fifty µl of diluted virus is added to 100 µl of PBMCs in flat bottom, tissue-culture treated 96-well plates (VWR#29442-054, Corning, Corning, N.Y.) and the plates are incubated at 37° C. in a humidified, 5% $CO_2$ incubator. After 7 days, 50 µl are removed from each well and tested for virus levels by p24 antigen ELISA (Perkin Elmer, Boston, Mass.). Virus titer is determined by the method of Reed and Muench (Table 11, see below).

Neutralization Assay:

Stimulated PBMCs are seeded into wells of 96-well flat bottom plates at a density of $1.4\times10^5$ cells/well. Virus is diluted to 2,000 TCID/ml and mixed with serial 0.5 $\log_{10}$ dilutions of compound for 1 h at 37° C. prior to addition to the cell plates. The final amount of virus added per well is 100 $TCID_{50}$. The final DMSO concentration in the assay is always 0.5% whenever small molecule inhibitors are being tested. Plates are incubated at 37° C. for 5 days, at which time an aliquot of supernatant is removed for p24 antigen ELISA. If control wells (virus without inhibitor) exhibit low p24 antigen levels then the plates are brought back to full volume with Titration medium and incubated for an additional 24 h.

Data Analysis:

Neutralization activity is displayed by plotting the percent inhibition of p24 antigen production (after background values are subtracted from all datapoints) versus $\log_{10}$ drug concentration. The percent inhibition is derived as follows [1−(p24 levels in the presence of drug/p24 levels in the absence of drug)]×100. $IC_{50}$ values are determined by fitting the inhibition data with a non-linear, four-parameter, variable slope equation (GraphPad Prism, ver. 4.02; GraphPad Software, San Diego, Calif.). Upper and lower inhibition values are constrained to 100% and 0%, respectively for curve fitting.

Phase 1a Clinical Study:

Individuals were treated in sequential, dose-rising cohorts of 5 subjects (4 active and 1 placebo) each and evaluated for up to 120 days post-treatment. A population of healthy, i.e., HIV-1 uninfected, male volunteers with no abnormal findings on physical exam, medical history and ECG, aged 19-50, was administered a single intravenous infusion of PRO 140 (0.1, 0.5, 2.0 and 5.0 mg per kg body weight). Safety assessments consisted of monitoring the following: vital signs (blood pressure, pulse, temperature, etc; hematology (hemoglobin, hematocrit, leukocytes, platelets, etc.); serum chemistries (AST/ALT, alkaline phosphatase, BUN, creatinine, etc.); urinalysis (pH, specific gravity, protein, glucose, leukocytes, etc.); and ECGs (12-lead).

Measurement of Coating of CCR5 Cells by PRO 140:

Whole blood specimens were combined separately with the indicated phycoerythrin-labeled anti-CCR5 antibodies or with appropriate isotype-control antibodies. Erythrocytes were lysed and leukocytes were stabilized using the ImmunoPrep Reagent System (Beckman Coulter), and the cells were analyzed on a TQ Prep™ flow cytometry workstation (Beckman Coulter). Data were expressed as the percent of CCR5 cells relative to all cells gated in the analysis. CTC5 is an anti-CCR5 antibody that does not compete with PRO 140. 2D7 is an anti-CCR5 antibody that does compete with PRO 140.

Measurement of Serum Concentrations of PRO 140:

Sera were diluted as appropriate and combined with L1.2-CCR5 cells, which are mouse pre-B lymphoma cells engineered to stably express human CCR5. In order to generate a standard curve, PRO 140 standard was tested in parallel at concentrations ranging from 0.062 to 4.0 µg/ml in 10% normal human serum (NHS). 10% NHS containing no PRO 140 was analyzed as a negative control. Following incubation with test samples, cells were washed and combined with a FITC-labeled sheep antibody against human IgG4 (The Binding Site Limited, Cat. #AF009). Cells were washed again and analyzed by flow cytometry. The concentration of PRO 140 was determined by comparing the median fluorescence intensity (MFI) of the test sample with MFI values of the standard curve.

Determination of Plasma RANTES Concentration:

The assay employed the Quantikine™ Human RANTES Immunoassay Kit (R&D Systems, Minneapolis, Minn.). Briefly, platelet-poor plasma was collected in CTAD/EDTA tubes and stored at −20° C. Test samples and RANTES standard were added to microtiter plates that were pre-coated with a mouse monoclonal antibody to RANTES. Following incubation, plates were washed and contacted with an anti-RANTES polyclonal antibody conjugated to horseradish peroxidase (HRP). Plates were washed again prior to addition of tetramethlybenzidine substrate for colorimetric detection. The Lower Limit of Quantification of the assay was 415 pg RANTES/ml plasma.

Results and Discussion

PRO 140 is a humanized IgG4,κ anti-CCR5 mAb being developed for HIV-1 therapy. Studies using this antibody have shown that PRO 140 broadly and potently inhibits CCR5-mediated fusion of HIV-1 to target cells in vitro. PRO 140 is also highly active in a therapeutic hu-PBL-SCID mouse model, and preliminary data are now available from a Phase 1a clinical study in healthy human subjects.

In Vitro Antiviral Activity of PRO 140:

Murine and humanized PRO 140 were tested against four primary R5HIV-1 isolates as described in the Methods. FIG. 1 shows that PRO 140 has potent antiviral activity in vitro, neutralizing a variety of primary R5 strains with an IC90 of 3-4 µg/ml. PRO 140 exhibited similar antiviral activity to the murine mAb, PA14, from which PRO 140 is derived.

Preliminary Data from Phase 1a Clinical Study:

The primary objective of the Phase 1a study was to evaluate the safety and tolerability of PRO 140 given as a single dose in a rising dose cohort regimen in healthy male subjects. The secondary objectives were (1) to gain information about the pharmacokinetics of intravenously administered PRO 140, and (2) to gain information on the effects of PRO 140 on blood levels of CCR5+ cells and chemokines.

Pharmacokinetics of PRO 140:

Healthy male volunteers were treated with a single intravenous infusion of PRO 140 at dose levels of 0.1, 0.5, 2.0 and 5.0 mg/kg. PRO 140 and placebo were generally well tolerated with no significant changes in ECGs and no dose-limiting toxicity.

Figure 7:
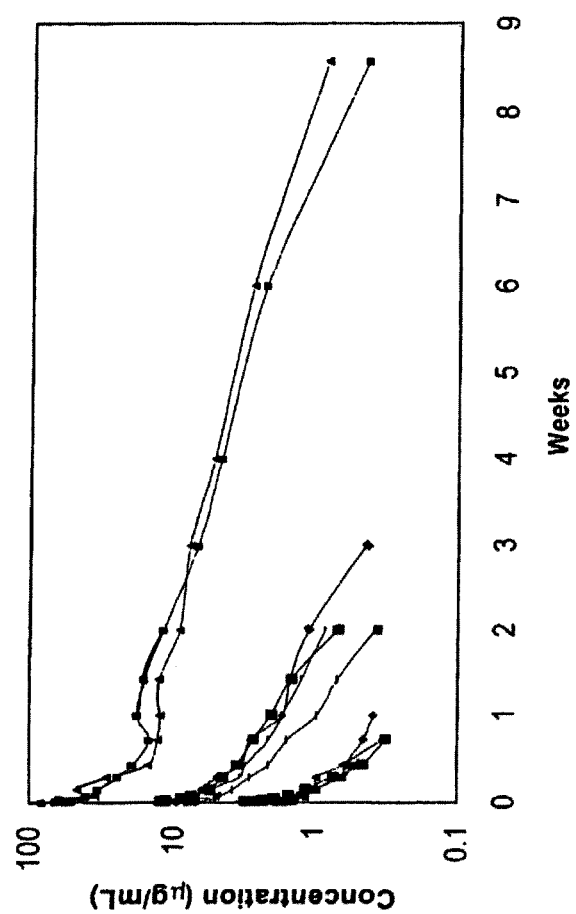
FIG. 7: Serum concentrations of PRO 140. Healthy male volunteers were treated with a single intravenous infusion of PRO 140 at dose levels of 0.1, 0.5 and 2.0 mg/kg, as indicated. At the indicated times post-treatment, serum was collected, cryopreserved, and analyzed for PRO 140 levels. Data for individual patients are indicated.

Serum was collected post-treatment, cryopreserved, and analyzed for PRO 140 levels. Peak serum concentrations ranged to 3 mg/ml at 0.1 mg/kg and 12 mg/ml at 0.5 mg/kg. Serum concentrations remained detectable (>400 ng/ml for up to 5 days at 0.1 mg/kg, 21 days at 0.5 mg/kg, and for over 60 days following a single 2 mg/kg injection (FIG. 7). Serum concentrations of PRO 140 increased proportionally with dose level, and the clearance rate was similar to that of other humanized mAbs. Pharmacokinetic (PK) metrics were determined using WinNonLin (PharSight Corporation, Mountain View, Calif.) using a noncompartmental model, and the terminal serum half-life of PRO 140 was determined to be 10-12 days. As expected, no subject developed antibodies to the humanized PRO 140.

Coating and Non-Depletion of CCR5 Lymphocytes by PRO 140:

Healthy male volunteers (n=4) were treated with a single intravenous infusion of PRO 140 at a dose level of 2 mg/kg. For up to 60 days post-treatment, at the times indicated in FIG. 6, blood was collected and analyzed for CCR5 lymphocyte levels.

Figure 6:
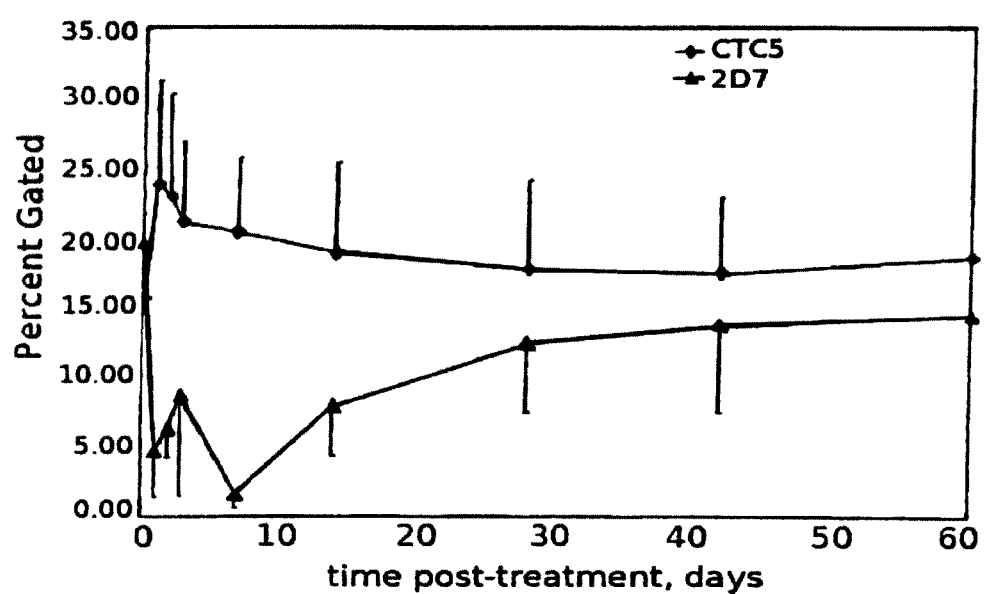
FIG. 6: PRO 140 coats but does not deplete CCR5 lymphocytes. Healthy male volunteers (n=4) were treated with a single intravenous infusion of PRO 140 at a dose level of 2 mg/kg. At the indicated times post-treatment, blood was collected and analyzed for CCR5 lymphocyte levels. The group mean values and standard deviations are indicated.

Following treatment with PRO 140, there was no decrease in the overall number of CCR5 lymphocytes at measured by CTC5 binding; however, the binding of antibody 2D7 was significantly decreased (FIG. 6). Background binding of isotype control antibodies was unchanged. Since the binding of CTC5 is not decreased by the presence of PRO 140, the CTC5-PE values are a measure of the total number of circulating CCR5 lymphocytes. Since 2D7 competes with PRO 140, the 2D7-PE values reflect the number of CCR5 lymphocytes that are not coated with PRO 140.

Figure 13:
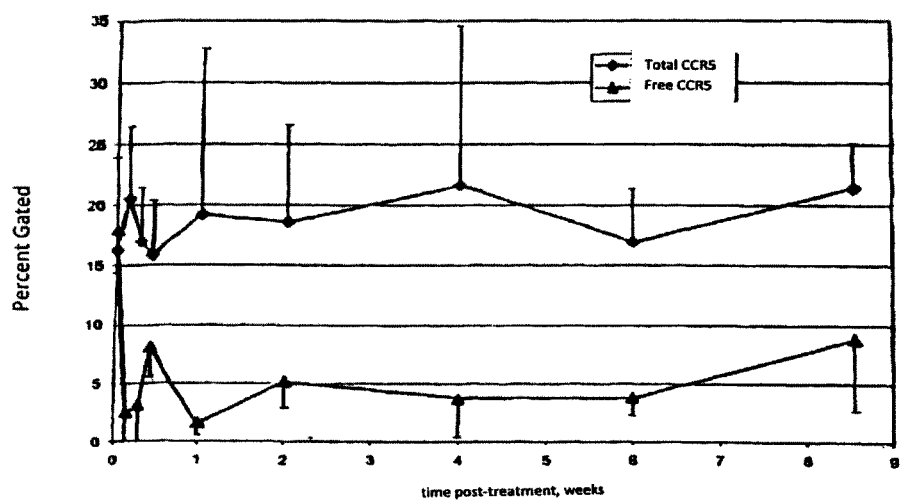
FIG. 13: PRO 140 coats but does not deplete lymphocytes. Healthy male volunteers (n=4) were treated with a single intravenous infusion of PRO 140 at a dose level of 5 mg/kg. At the indicated times post-treatment, blood was collected and analyzed for CCR5 lymphocyte levels. The group mean values and standard deviations are indicated.
Figure 14:
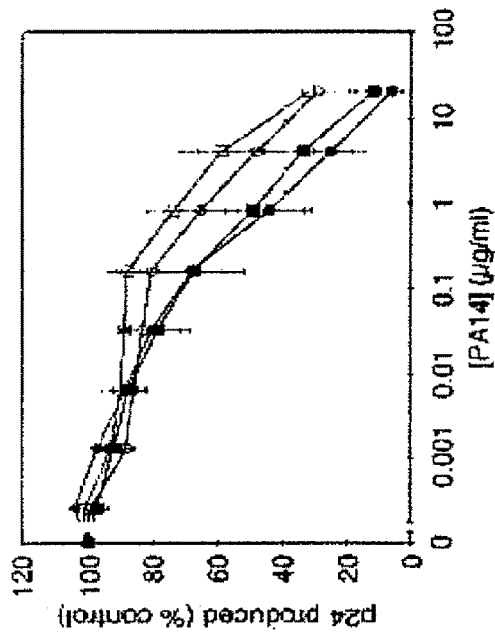
FIG. 14: PRO 140 is active against HIV-1 strains that are resistant to small-molecule CCR5 antagonists. Variants of HIV-1 resistant to AD101 (a small-molecule CCR5 inhibitor structurally related to SCH-C) and SCH-D (Kuhmann et al., 2004; Maroznan et al. 2005) were tested for sensitivity to the anti-CCR5 mAb, PA14. The extent of viral replication in primary CD4+ T-cells is represented relative to p24 antigen production in the absence of any inhibitor, which is defined as 100%. Individual data points were the average of values derived from 4 separate experiments, each performed using duplicate wells. The data show that whereas the AD101- and SCH-D-resistant HIV-1 variants were resistant to SCH-C and SCH-D, respectively, replication of these variants was potently inhibited by PA14 (Maroznan et al. 2005).
Figure 14:
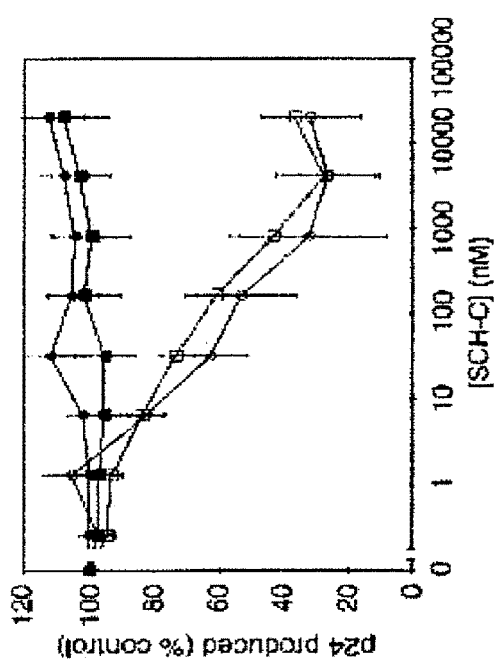
Figure 14:
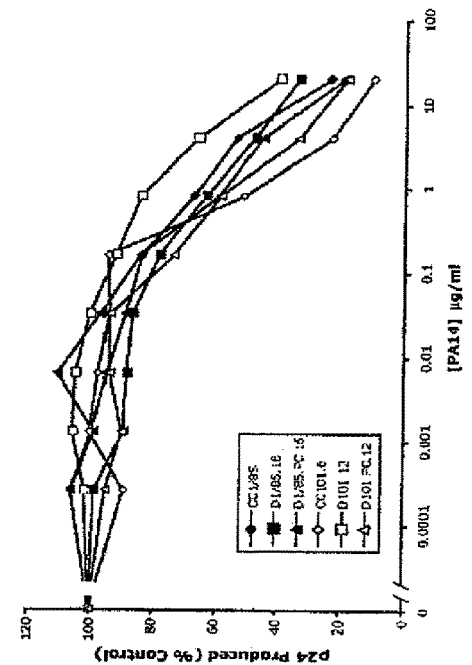
Figure 14:
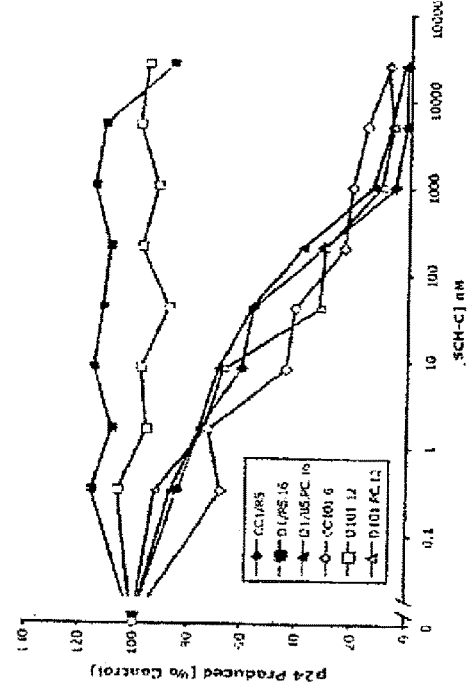

The data indicate that a single 2 mg/kg dose of PRO 140 effectively coats CCR5 lymphocytes without cellular depletion for two weeks, and cells remain partially coated for >4 weeks. In addition, CCR5 coating was more prolonged in patients treated with 5 mg/kg PRO 140. The data indicate that a single 5 mg/kg dose of PRO 140 effectively coats CCR5 lymphocytes without cellular depletion and the cells remain partially coated for >60 days (FIG. 13). Since CCR5 coating is the mechanism whereby PRO 140 inhibits HIV, viral loads in HIV-infected individuals could be expected to decrease in a similar temporal manner.

Figure 8:
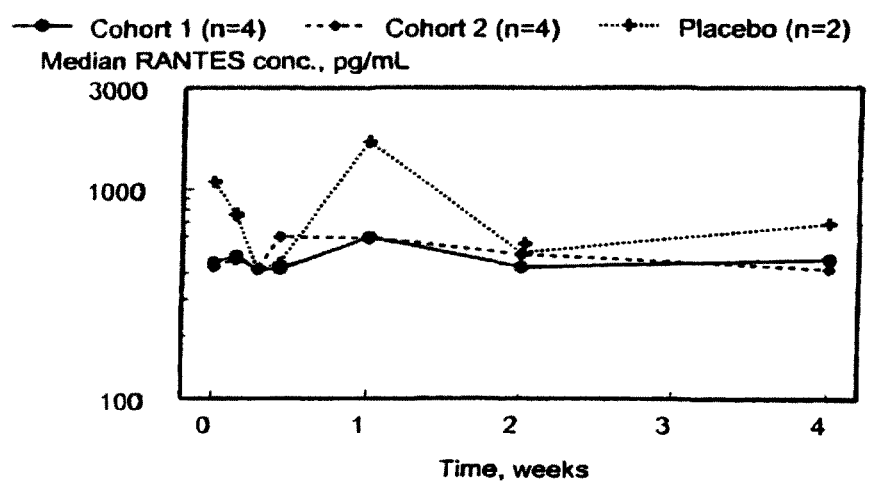
FIG. 8: PRO 140 does not affect plasma chemokine levels. Healthy male volunteers were treated with a single intravenous infusion of 0.1 mg/kg PRO 140 (Cohort 1), 0.5 mg/kg PRO 140 (Cohort 2) or matched placebo. At the indicated times post-treatment, plasma was collected, cryopreserved and analyzed for levels of RANTES. The Lower Limit of Quantification of the assay was 415 µg RANTES/mL plasma. Data represent the group mean values.
Figure 9:
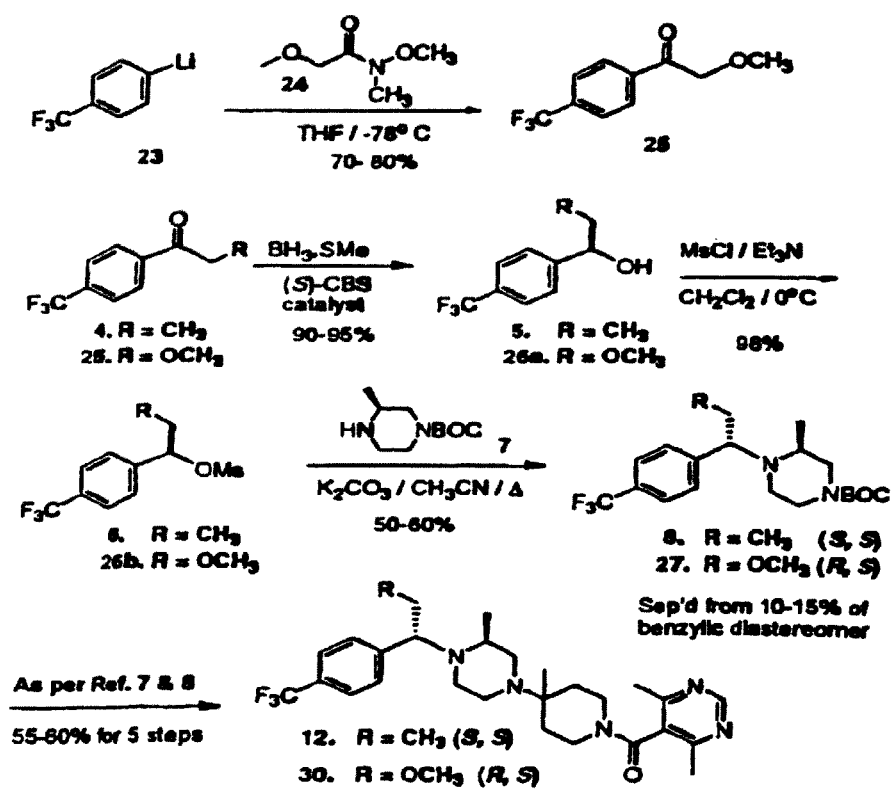
FIG. 9: Scheme for chemical synthesis of SCH-D.
Figure 10:
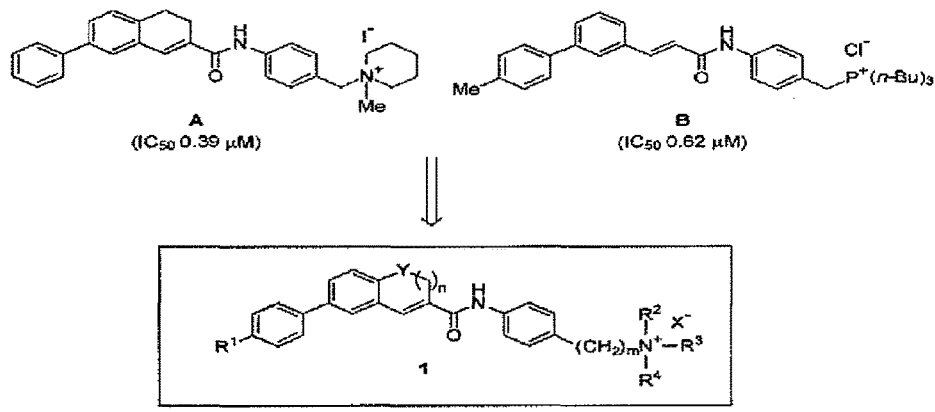
FIG. 10: Scheme for chemical synthesis of TAK-779. The method is as described in Shiraishi et al., 2000.
Figure 10:
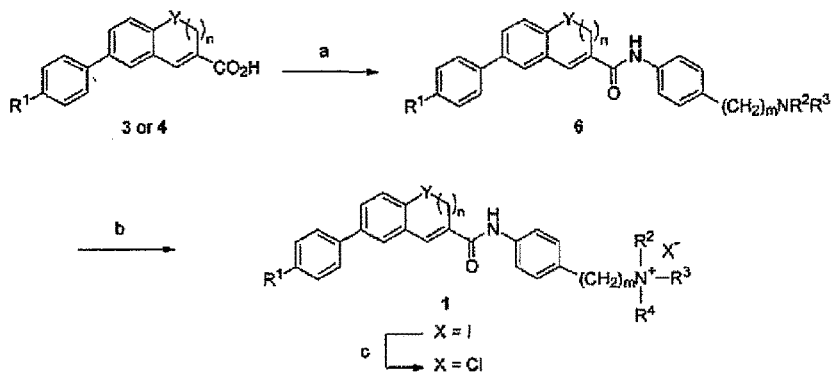
Figure 10:
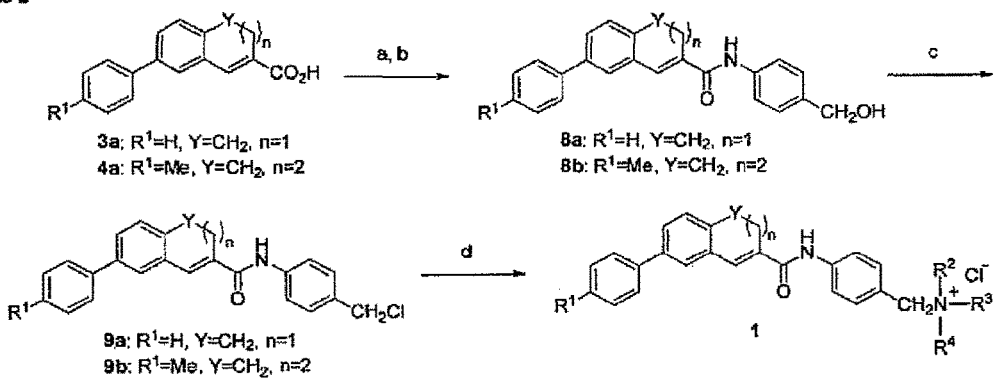
Figure 11:
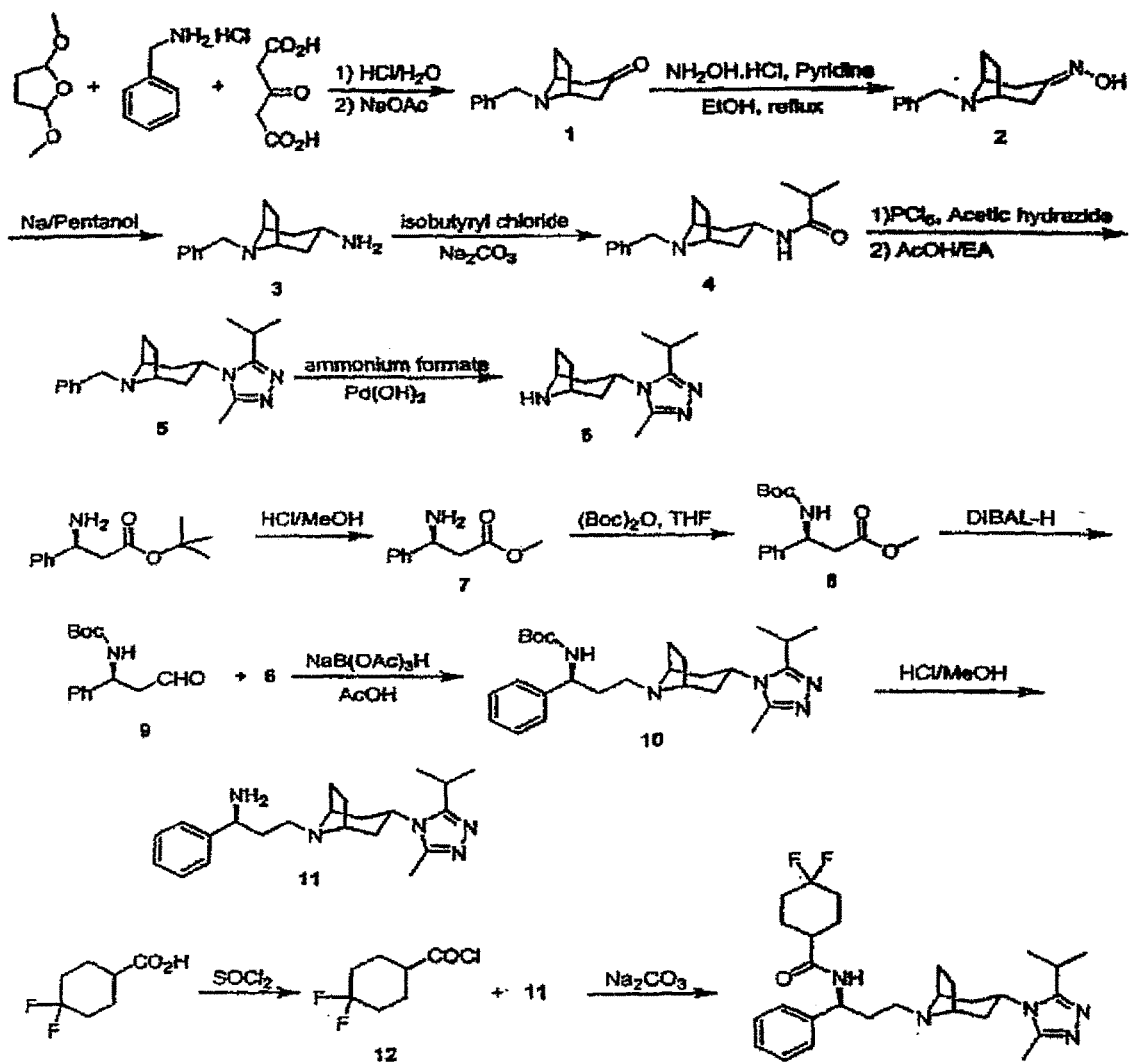
FIG. 11: Scheme for chemical synthesis of UK-427,857. The method is as described in PCT International Publication No. WO 01/90106 A2, published Nov. 29, 2001.
Figure 12:
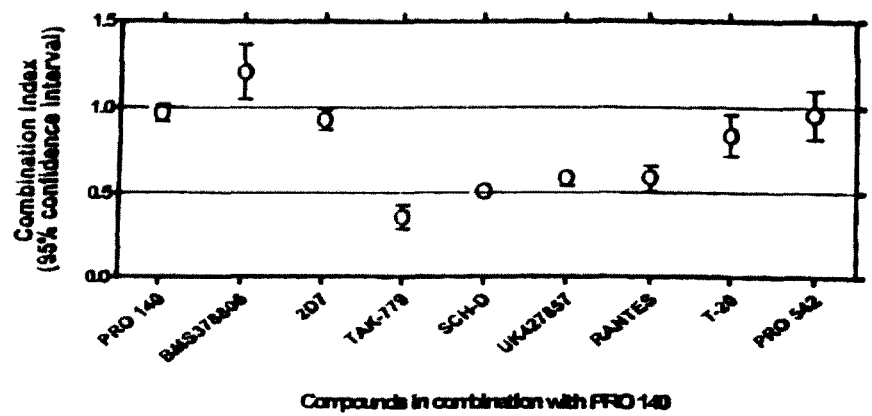
FIG. 12: Synergistic inhibition of HIV-1 fusion exhibited by PRO 140 with different compounds. Interactions between PRO 140 and small-molecule, peptide, mAb, and chimeric CD4-immunoglobulin inhibitors of CCR5, CD4, gp120 and gp41 targets for inhibiting HIV-1 fusion were assessed using the RET assay. Mean combination index (CI) values with 95% confidence intervals are plotted for data obtained using the compounds combined in a 1:1 molar ratio. A CI value of <1 indicates synergistic interactions; a CI value of 1 indicates additive interactions; and a CI value of >1 indicates antagonistic interactions.

Effect of PRO 140 on Plasma Chemokine Levels:

Healthy male volunteers were treated with a single intravenous infusion of 0.1 mg/kg PRO 140 (Cohort 1), 0.5 mg/kg PRO 140 (Cohort 2) or matched placebo. Plasma was collected post-treatment at the indicated times, cryopreserved and analyzed for levels of RANTES, a CC-chemokine that serves as a natural ligand for CCR5. RANTES levels were measured by ELISA in platelet-depleted plasma pre-dose and up to 28 days post-dose. As shown in FIG. 8, there was no significant change in RANTES levels following PRO 140 treatment (P>0.14 all times). These data are consistent with in vitro findings that PRO 140 does not antagonize CCR5 function. The findings suggest that PRO 140 does not have untoward effects on CCR5-mediated immune function in treated patients.

The results described herein indicate that in addition to PRO 140 broadly and potently inhibiting CCR5-mediated HIV-1 entry without CCR5 antagonism or other immunologic side effects in preclinical testing, this has demonstrated favorable tolerability, PK and immunologic profiles in preliminary results from an ongoing Phase 1a study in healthy volunteers. Thus, in many respects, PRO 140 offers a novel and attractive product profile for anti-HIV-1 therapy.

Moreover, the activities of anti-CCR5 mAbs are fundamentally distinct from, but complementary to, those of small-molecule CCR5 antagonists (see Table 2) which are also currently undergoing human clinical trials. PRO 140 has recently been shown to work synergistically with non-antibody CCR5 antagonists in inhibiting CCR5-mediated HIV-1 fusion to target cells.

Accordingly, combination therapy comprising administration of anti-CCR5 mAbs and non-antibody CCR5 antagonists may offer powerfully effective, new approaches to preventing and treating HIV-1 infection.

Part II

Example 1

Combination Testing of PRO 140 and HIV-1 Entry Inhibitors in the Fluorescence RET Assay Materials and Methods Compounds and mAbs:

PRO 140 was prepared by expression in Sp2/O cells using Hybridoma serum-free medium supplemented with 2 mM L-glutamine (Invitrogen, Carlsbad, Calif.). Bulk mAb was clarified using a 5.0 µm Depth filter (Sartorius, Goettingen, Germany) followed by passage over a 0.2 µm sterilizing grade filter (Sartorius). The mAb was purified by passage first over an affinity column (MabSelect Protein A column, Amersham, Piscataway, N.J.) and then by ion exchange chromatography (SP Sepharose Cation Exchange resin, Amersham). PRO 140 was nanofiltered using a Viresolve™ 10 Opticap NFP capsule (Millipore, Billerica, Mass.) followed by a 0.2 µm filter and concentrated/diafiltered over disposable TFF cartridges (Millipore). The mAb was then polished over a hydroxyapatite column (Bio-Rad, Hercules, Calif.), concentrated to 10 mg/ml in phosphate-buffered saline and stored at −70° C. or colder prior to use.

SCH-D (Schering Plough; Tagat et al., 2004), TAK-779 (Takeda Pharmaceuticals; Shiraishi et al., 2000), UK-427, 857 (Pfizer; Wood and Armour, 2005), and BMS378806 (Bristol-Myers Squibb; Lin et al., 2003) were prepared by commercial sources.

SCH-D has the following structure:

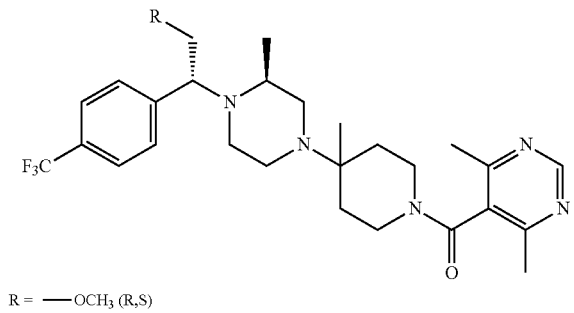

R = —OCH₃ (R,S)

SCH-D (also designated SCH-417690): 1-[(4,6-dimethyl-5-pyrimidinyl)carbonyl]-4-[4-[2-methoxy-1(R)-4-(trifluoromethyl)phenyl]ethyl-3(S)-methyl-1-piperazinyl]-4-methylpiperidine (Schering-Plough)

SCH-D was synthesized according to the procedure described in Tagat et al. (2004) and set forth in FIG. 1.

TAK-779 has the following structure:

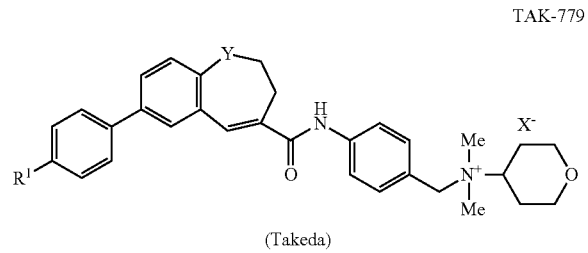

Y = —CH₂
X = —Cl
R¹ = —CH₃

Figure 2:
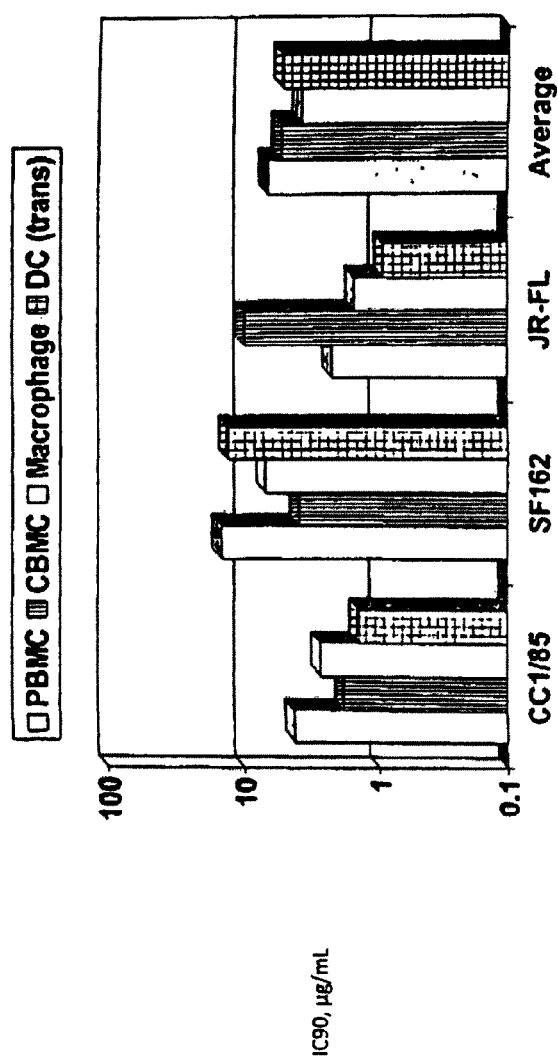
FIG. 2: Antiviral activity is independent of target cell. Inhibition of infection of four different target cells by three primary R5 HIV-1 isolates with was tested.

TAK-779 was synthesized according to the procedure described in Shiraishi et al. (2000) and set forth in FIG. 2.

TAK-652 has the following structure:

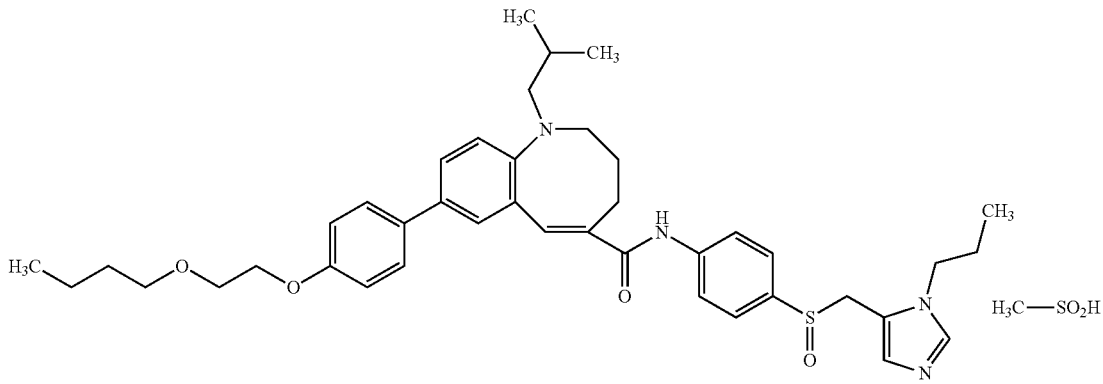

UK-427,857 (maraviroc) has the following structure:

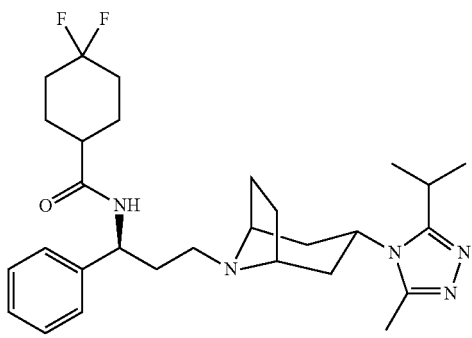 [SMILES: Cc1nnc(C(C)C)n1C1CC2CCC(C1)N2CC[C@H](NC(=O)C1CCC(F)(F)CC1)c1ccccc1]

Figure 3:
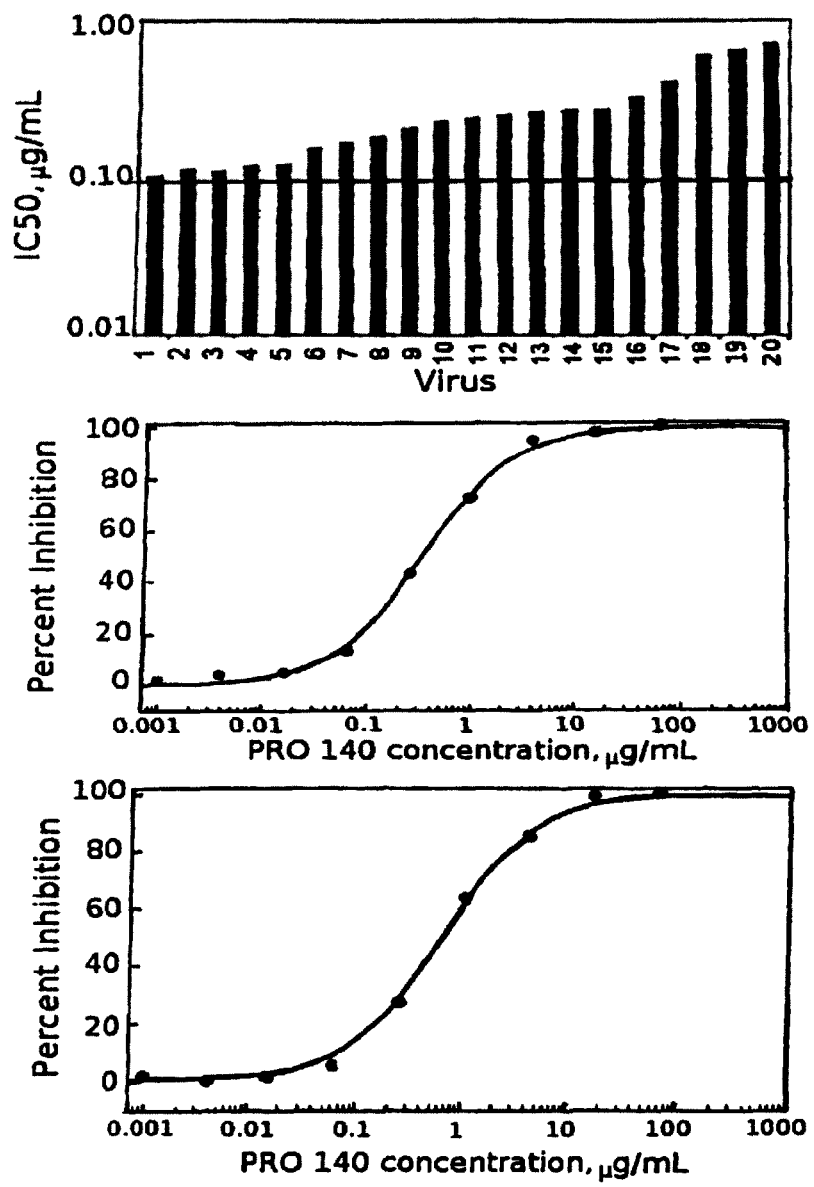
FIG. 3: In vitro HIV-1 susceptibility to PRO 140 quantified using the PhenoSense™ entry assay. PRO 140 was tested for activity against 20 primary HIV-1 isolates in the PhenoSense HIV Entry™ assay at ViroLogic, Inc. (now Monogram Biosciences, South San Francisco, Calif.). Drug susceptibility is reported as $IC_{50}$ values, which represent the concentration required for 50% inhibition of viral infectivity.

UK-427,857: (Pfizer)
UK-427,857 was synthesized according to the procedure described in PCT International Publication No. WO 01/90106 and set forth in FIG. 3.
BMS378806 has the following structure:

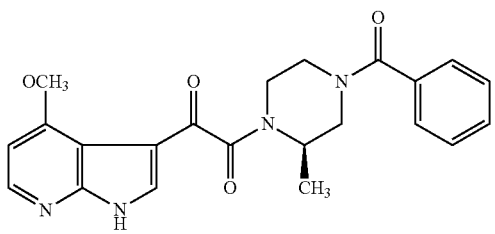 [SMILES: COc1ccnc2[nH]cc(C(=O)C(=O)N3CCN(C(=O)c4ccccc4)C[C@H]3C)c12]

BMS378806: (R)—N-(benzoyl)-3-methyl-N'-[(4-methoxy-7-azaindol-3-yl)-oxoacetyl]-piperazine (Bristol-Myers Squibb)

It was synthesized according to the procedure described in U.S. Pat. No. 6,476,034 (compound 17a).

Nevirapine (Boehringer Ingelheim; Merluzzi et al., 1990) and atazanavir (Bristol-Myers Squibb; Robinson et al., 2000) were purchased from commercial sources. PRO 542 was expressed in Chinese hamster ovary cells and purified as described previously (Allaway et al., 1995). T-20 (Fuzeon®) was synthesized by solid-phase fluroenylmethoxycarbonyl chemistry, was purified by reverse-phase chromatography and was analyzed for purity and size by HPLC and mass spectroscopy as described previously (Nagashima et al., 2001). AZT was purchased from Sigma Chemicals (St. Louis, Mo.). RANTES was purchased from R&D Systems (Minneapolis, Minn.). The anti-CCR5 mAb 2D7 was purchased from Pharmingen (San Diego, Calif.), and the anti-CD4 mAb Leu-3A was purchased from Becton Dickinson (Franklin Lakes, N.J.).

For testing, small molecule compounds were solubilized in dimethylsulfoxide (DMSO) to 10 mM and then diluted in DMSO to 200× the final concentration to be utilized in the antiviral assay. Serial dilutions of small molecules were conducted in DMSO. Subsequent dilutions were conducted in medium to achieve a final DMSO concentration in the assay of 0.5%. Peptides and mAbs were diluted in PBS in the absence of DMSO. Typically, inhibitor concentrations in the RET assay included eleven 3-fold dilutions ranging from 200 nM to 3.0 pM.

Cell Preparation:

HeLa cells were engineered to express HIV-1 gp120/gp41 from the macrophage-tropic primary isolate JRFL as described (HeLa-EnviRFL; Litwin et al., 1996). Briefly, the HIV-1$_{LAI}$ Env gene was excised from the plasmid pMA243 (Dragic et al., 1992) and the HIV-1$_{JRFL}$ Env gene was inserted. The HIV-1JRFL Env gene was amplified from the plasmid pUCFL112-1 (Koyanagi et al., 1987). The resulting plasmid, designated JR-FL-pMA243, was sequenced by standard methods and transfected into HeLa cells using lipofectin (Gibco BRL/Invitrogen, Carlsbad, Calif.). HeLa-Env$_{JRFL}$ transfectants were selected in methotrexate (Sigma, St. Louis, Mo.) and cloned twice by limiting dilution. The transduced human T cell leukemia line CEM NKR-CCR5 cells were obtained from the NIH AIDS Research and Reference Program (Cat. No. 458).

RET Assay:

The HIV-1 RET assay has been described in detail previously (Litwin et al., 1996). Briefly, fluorescein octadecyl ester (F18; Molecular Probes, Eugene, Oreg.; 5 mg/ml in ethanol), was diluted 1:800 in DMEM labeling medium (DMEM; Invitrogen, Carlsbad, Calif.) with 10% fetal bovine serum (FBS; HyClone, Logan, Utah) and adjusted to an $A_{506}$ of 0.34±10%. Octadecyl rhodamine B chloride (R18; Molecular Probes; 10 mg/ml in ethanol) was diluted 1:2050 in labeling medium and adjusted to an $A_{565}$ of 0.52±10%. Both dyes were further diluted 2-fold by addition to cells in T75-cm² flasks. HeLa-Env$_{JRFL}$ and CEM NKR-CCR5 cells were incubated overnight in F18- and R18-containing culture medium, respectively. The following day, medium from HeLa-Env$_{JRFL}$ cells was removed and 10 ml of 0.5 mM EDTA was added and incubated at 37° C. for 5 min. EDTA was removed and the flask was returned to the incubator for another 5 min followed by striking of the flask to dislodge cells. Ten ml of PBS– with 15% FBS were added to the flask and the contents were transferred to a 50-ml conical centrifuge tube. Suspension CEM NKR-CCR5 cells were added directly to a separate 50-ml conical centrifuge tube. Both cell lines were centrifuged at 300×g for 5 min. The supernatant was discarded and cells were resuspended in 10 ml of PBS–/15% FBS. The centrifugation/wash step was repeated twice, after which the cells were counted and concentrations adjusted to $1.5 \times 10^6$ cells/ml. Ten µl of each cell type (15,000 cells) were seeded into wells of a 384-well plate. Inhibitor compounds were added immediately thereafter to bring the final well volume to 40 µl, and the plates were incubated for 4 h at 37° C. Compounds were tested individually and in combination at a fixed molar ratio or mass ratio over a range of serial dilutions. The plates were then read on a fluorescence plate reader (Victor$^2$, Perkin Elmer, Boston, Mass.) using the excitation/emission filter combinations shown in Table 6a.

TABLE 6a

Excitation/emission filter combinations for RET assay

| Scan No. | Excitation wavelength | Emission wavelength |
|---|---|---|
| 1 | 450 nm/50 nm | 530 nm/25 nm |
| 2 | 530 nm/25 nm | 590 nm/35 nm |
| 3 | 450 nm/50 nm | 590 nm/35 nm |

The "% Inhibition" was calculated according to the following formula:

$$\% \text{ Inhibition} = 100 \times [(\text{Max \% RET} - \% \text{ RET for sample well})/(\text{Max \% RET} - \text{Min \% RET})]$$

Where:
Max % RET=average of % RET values for HeLa and CEM cell combination without added inhibitor; and
Min % RET=average of % RET values for HeLa and CEM cell combination in presence of 500 ng/ml of Leu-3a mAb (an antibody that targets CD4 and fully blocks fusion in the RET assay at this concentration).

Fifty percent inhibition ($IC_{50}$) values were determined by fitting the inhibition data with a non-linear, four-parameter, variable slope equation (GraphPad Prism, ver. 4.02; GraphPad Software, San Diego, Calif.). Upper and lower inhibition values were constrained to 100% and 0%, respectively for curve fitting.

Synergy Determinations:
Cooperative inhibition effects of drug combinations were determined by the method of Chou and Talalay (1984). $IC_{50}$ values were generated for all combinations as described above. Combination Index (CI) and Dose Reduction (DR) values were calculated according to the following formulas:

$$CI = \left[\frac{IC_{50}Dcomb1}{IC_{50}Dsolo1}\right] + \left[\frac{IC_{50}Dcomb2}{IC_{50}Dsolo2}\right] + \alpha \left[\frac{(IC_{50}Dcomb1)(IC_{50}Dcomb2)}{(IC_{50}Dsolo1)(IC_{50}Dsolo2)}\right]$$

DR (for compound 1)=($IC_{50}$ Dsolo1/$IC_{50}$ Dcomb1)
DR (for compound 2)=($IC_{50}$ Dsolo2/$IC_{50}$ Dcomb2)
Where:
"$IC_{50}$ Dcomb1"=$IC_{50}$ of drug 1 in combination with drug 2;
"$IC_{50}$ Dsolo1"=$IC_{50}$ of drug 1 when tested alone;
"$IC_{50}$ Dcomb2"=$IC_{50}$ of drug 2 in combination with drug 1;
"$IC_{50}$ Dsolo2"=$IC_{50}$ of drug 2 when tested alone;
$\alpha$=0 if the effects of the two drugs are mutually exclusive; and
$\alpha$=1 if the effects of the two drugs are mutually nonexclusive Combinations with CI<1 are determined to be synergistic, whereas combinations with CI>1 are determined to be antagonistic. Additivity is reflected in combinations for which CI=1.

Ninety five percent Confidence Intervals were calculated in Microsoft Excel using the formula:

=Confidence(alpha,stdev,$n$)

Where:
alpha=0.05 (95% confidence);
stdev=standard deviation of dataset mean; and
n=number of replicates.

Results
Preparation of Small-Molecule Fusion Inhibitors:
SCH-D, TAK-779, UK-427,857, and BMS378806 were prepared by commercial sources. The desired quantities and HPLC purity of the compounds were realized. Purity of the compounds was supported by results obtained from elemental analysis, and the identities of the products were confirmed by proton NMR (proton and carbon-13) and/or mass spectrum data.

Synergistic interactions revealed by RET assay: Synergy experiments were conducted using the cell-cell RET fusion assay to assess initially the potential for cooperative interactions between PRO 140 and small-molecule and peptide-based inhibitors of CCR5, CD4, HIV-1 gp120 and HIV-1 gp41. The experiments were then extended to the CCR5-specific murine monoclonal antibody, 2D7 (Wu et al., 1997).

Experiments measuring inhibition of HIV-1 Env-mediated fusion were first conducted using combinations of PRO 140 with, respectively, PRO 140 itself, 3 small-molecule CCR5 antagonists (SCH-D, TAK-779, UK427857), the natural peptide ligand of CCR5 (RANTES), and an anti-CCR5 mAb (2D7), a peptide-based inhibitor of gp41 (T-20), a protein-based inhibitor of gp120 (PRO 542), a small-molecule inhibitor of gp120 (BMS378806), and an anti-CD4 mAb (Leu3A). Mass ratios of PRO 140 to other entry inhibitors ranged from 0.75 to 364. The results are shown in Table 7.

TABLE 7

Combination Index and Dose Reduction Values for inhibition of HIV-1 Env-mediated fusion with combinations of PRO 140 and entry inhibitors

| | | | | Cell-cell fusion assay | | |
|---|---|---|---|---|---|---|
| PRO 140 in combination with:[a] | No. of tests | Cpd mass ratios[b] | Inhibitor target | Mean CI[c] | Mean Dose Reduction (PRO 140) | Mean Dose Reduction (Cpd in combination) |
| PRO 140 | 9 | 1 | CCR5 | 0.97 ± 0.08 | 2.07 ± 0.18 | 2.07 ± 0.18 |
| TAK-779 | 8 | 282 | CCR5 | 0.36 ± 0.10 | 4.10 ± 2.03 | 15.86 ± 7.10 |
| SCH-D | 9 | 279 | CCR5 | 0.51 ± 0.05 | 4.21 ± 0.96 | 3.90 ± 0.71 |
| UK-427,857 | 3 | 292 | CCR5 | 0.59 ± 0.04 | 4.16 ± 0.41 | 2.98 ± 0.65 |
| RANTES | 4 | 19 | CCR5 | 0.59 ± 0.08 | 4.13 ± 0.99 | 3.24 ± 1.06 |
| 2D7 | 2 | 1 | CCR5 | 0.93 ± 0.04 | 1.87 ± 0.07 | 2.54 ± 0.13 |
| T-20 | 7 | 33 | gp41 | 0.84 ± 0.16 | 1.77 ± 0.40 | 7.47 ± 3.34 |

TABLE 7-continued

Combination Index and Dose Reduction Values for inhibition of HIV-1 Env-mediated fusion with combinations of PRO 140 and entry inhibitors

| | | | | Cell-cell fusion assay | | |
|---|---|---|---|---|---|---|
| PRO 140 in combination with:[a] | No. of tests | Cpd mass ratios[b] | Inhibitor target | Mean CI[c] | Mean Dose Reduction (PRO 140) | Mean Dose Reduction (Cpd in combination) |
| PRO 542 | 6 | 0.75 | gp120 | 0.96 ± 0.17 | 1.59 ± 0.21 | 5.54 ± 1.49 |
| BMS-378806 | 7 | 364 | gp120 | 1.21 ± 0.21 | 1.64 ± 0.30 | 2.85 ± 0.76 |

[a]Compounds were tested at a 1:1 molar ratio.
[b]Mass of PRO 140/mass of other HIV-1 entry inhibitor tested in combination. Molecular weights of inhibitors are: PRO 140 ≈ 150,000 g/mole; SCH-D = 538 g/mole; TAK-779 = 531 g/mole (hydrochloride salt); UK-427,857 = 514 g/mole; RANTES ≈ 7,800 g/mole; 2D7 ≈ 150,000 g/mole; T-20 = 4,492 g/mole; PRO 542 ≈ 200,000 g/mole; BMS-378806 = 412 g/mole.
[c]Combination Index at $IC_{50}$ value. The mutually exclusive CI formula ($\alpha = 0$) was utilized for PRO 140 in combination with molecules that bind CCR5, and the mutually non-exclusive formula ($\alpha = 1$) was utilized for PRO 140 in combination with molecules that bind other targets (Chou and Rideout, 1991).

Two small-molecule CCR5 antagonists, SCH-D and TAK-779, were assayed in combination. PRO 542, a recombinant antibody-like fusion protein in which the heavy- and light-chain variable domains of human IgG2 have been replaced with the D1D2 domains of human CD4, was also tested in combination with the anti-CD4 mAb. Leu-3A. The results of these assays are shown in Table 8.

TABLE 8

Other drug combinations tested in the RET assay for cooperativity

| Drug 1 | Drug 2 | Molar ratios (Drug 1 to 2) | N | Mean CI ± stdev[a] | Mean DR (Drug 1) | Mean DR (Drug 2) |
|---|---|---|---|---|---|---|
| SCH-D | TAK-779 | 1:1 | 4[b] | 1.12 ± 0.32 | 1.48 ± 0.96 | 4.31 ± 1.82 |
| PRO 542 | Leu-3A | 22.9:1 | 2 | 16.9 ± 0.3 | 0.7 ± 0 | 0.16 ± 0 |

[a]CI values were calculated using the mutually exclusive formula for SCH-D vs. TAK-779 (i.e., where $\alpha = 0$) and the mutually non-exclusive formula for PRO 542 vs. Leu-3A (i.e., where $\alpha = 1$; see methods).
[b]One aberrant datapoint was culled from the calculation of Mean CI and Mean DRs.

Figure 4:
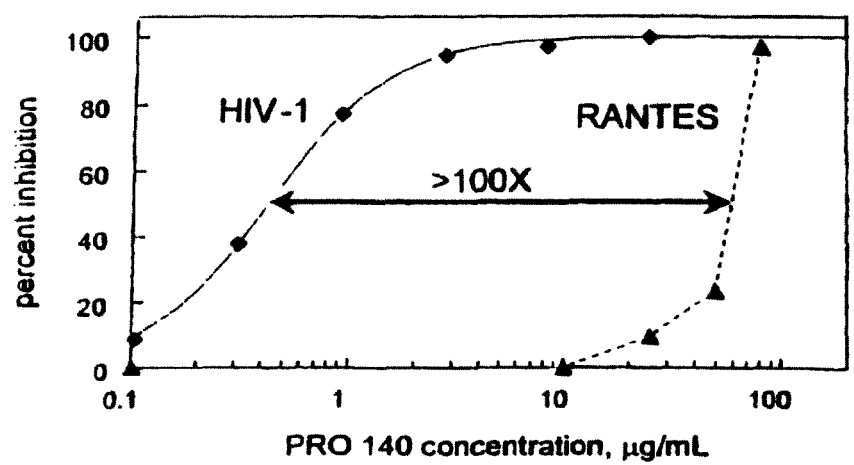
FIG. 4: PRO 140 blocks HIV-1 but not chemokine signaling. The effects of PRO 140 on the inhibition of RANTES-induced calcium mobilization in L1.2-CCR5 cells and on inhibition of HIV-1$_{JR-FL}$ replication in PBMC cultures were determined. Similar results were obtained for MIP-1α and MIP-1β.
Figure 5:
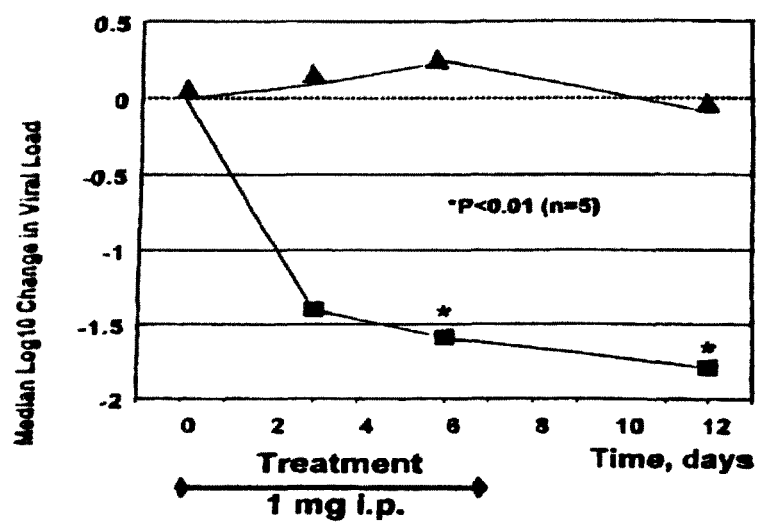
FIG. 5: PRO 140 provides prolonged control of viral replication in HIV-1-infected mice. SCID mice were reconstituted with normal human peripheral blood mononuclear cells and infected 2 weeks later with HIV-1$_{JR-CSF}$. Multiple doses of PRO 140 were administered following attainment of steady state viral levels. Plasma viral loads pre- and post-injection are indicated.

The effect of varying the relative amounts of compounds in the combinations on the level of cooperativity was also measured. Molar ratios of 5:1 and 1:5 PRO 140 were used. The results are tabulated in Table 9, and the mean CI values with 95% confidence intervals are plotted in FIG. 4 for the 1:1 molar ratio data. In addition to PRO 140, the inhibitory activity of mAb 2D7, a CCR5-specific murine antibody (Wu et al., 1997) was also tested in combination with the small-molecule CCR5 antagonists and with RANTES using the fluorescent RET assay. The results are shown in Table 10.

TABLE 9

Combination Index and Dose Reduction Values for inhibition of HIV-1 Env-mediated fusion with combinations of PRO 140 and entry inhibitors

| | | | Cell-cell fusion assay | | |
|---|---|---|---|---|---|
| PRO 140 in combination with: | Ratio[a] | Cpd Mass Ratios[b] | Mean Combination Index[c] | Mean Dose Reduction (PRO 140) | Mean Dose Reduction (Cpd. in combination) |
| PRO 140 | 5:1 | 5 | 1.15 ± 0.09 | 1.05 ± 0.08 | 5.26 ± 0.41 |
| PRO 140 | 1:5 | 0.2 | 1.09 ± 0.08 | 5.54 ± 0.38 | 1.10 ± 0.08 |
| TAK-779 | 5:1 | 1410 | 0.57 ± 0.07 | 1.89 ± 0.14 | 33.59 ± 18.85 |
| TAK-779 | 1:5 | 56.4 | 0.52 ± 0.20 | 5.58 ± 0.52 | 3.78 ± 1.95 |
| SCH-D | 5:1 | 1395 | 0.66 ± 0.10 | 1.92 ± 0.40 | 8.44 ± 1.27 |
| SCH-D | 1:5 | 55.8 | 0.69 ± 0.05 | 9.95 ± 2.03 | 1.73 ± 0.19 |
| UK-427,857 | 5:1 | 1460 | 0.66 ± 0.11 | 2.00 ± 0.35 | 7.25 ± 2.19 |
| UK-427,857 | 1:5 | 58.4 | 0.73 ± 0.05 | 11.31 ± 2.14 | 1.58 ± 0.17 |
| RANTES | 5:1 | 95 | 0.84 ± 0.14 | 1.63 ± 0.43 | 5.39 ± 1.13 |
| RANTES | 1:5 | 3.8 | 0.66 ± 0.06 | 13.64 ± 4.75 | 1.75 ± 0.28 |
| T-20 | 5:1 | 165 | 1.10 ± 0.12 | 0.98 ± 0.11 | 31.85 ± 10.19 |
| T-20 | 1:5 | 6.6 | 0.76 ± 0.27 | 2.93 ± 0.68 | 3.85 ± 1.50 |
| PRO 542 | 5:1 | 3.75 | 1.13 ± 0.10 | 1.01 ± 0.07 | 15.73 ± 4.15 |
| PRO 542 | 1:5 | 0.15 | 1.18 ± 0.17 | 2.83 ± 0.50 | 1.71 ± 0.29 |
| BMS-378806 | 5:1 | 1820 | 1.12 ± 0.10 | 1.14 ± 0.06 | 8.88 ± 4.16 |
| BMS-378806 | 1:5 | 72.8 | 1.55 ± 0.24 | 3.64 ± 0.73 | 1.07 ± 0.31 |

[a]Molar ratio of PRO 140 to other entry inhibitor tested in combination (n = 3 for all experimental results)
[b]Mass of PRO 140/mass of other HIV-1 entry inhibitor tested in combination. Molecular weights of inhibitors are: PRO 140 ≈150,000 g/mole; SCH-D = 538 g/mole; TAK-779 = 531 g/mole (hydrochloride salt); UK-427,857 = 514 g/mole; RANTES ≈ 7,800 g/mole; T-20 = 4,492 g/mole; PRO 542 ≈ 200,000 g/mole; BMS-378806 = 412 g/mole.
[c]Combination Index at $IC_{50}$ value. The mutually exclusive CI formula ($\alpha = 0$) was utilized for PRO 140 in combination with molecules that bind CCR5, and the mutually non-exclusive formula ($\alpha = 1$) was utilized for PRO 140 in combination with molecules that bind other targets (Chou and Rideout, 1991).

TABLE 10

Combination Index and Dose Reduction Values for inhibition of HIV-1 Env-mediated fusion with combinations of 2D7 and entry inhibitors

| 2D7 in combination with:[a] | Cpd Mass Ratios[c] | Inhibitor target | Mean Combination Index[b] | Mean Dose Reduction (2D7) | Mean Dose Reduction (Cpd in combination) |
|---|---|---|---|---|---|
| | | | Cell-cell fusion assay | | |
| TAK-779 | 282 | CCR5 | 0.15 ± 0.03 | 17.20 ± 3.23 | 11.95 ± 4.94 |
| SCH-D | 279 | CCR5 | 0.57 ± 0.10 | 3.25 ± 0.56 | 4.04 ± 0.78 |
| UK427857 | 292 | CCR5 | 0.58 ± 0.03 | 2.45 ± 0.12 | 5.73 ± 0.54 |

TABLE 10-continued

Combination Index and Dose Reduction Values for inhibition of HIV-1
Env-mediated fusion with combinations of 2D7 and entry inhibitors

| 2D7 in combination with:[a] | Cpd Mass Ratios[c] | Inhibitor target | Mean Combination Index[b] | Mean Dose Reduction (2D7) | Mean Dose Reduction (Cpd in combination) |
|---|---|---|---|---|---|
| | | | Cell-cell fusion assay | | |
| RANTES | 19 | CCR5 | 0.62 ± 0.04 | 1.94 ± 0.08 | 10.18 ± 1.86 |
| PRO 140 | 1 | CCR5 | 0.93 ± 0.04 | 2.54 ± 0.13 | 1.87 ± 0.07 |

[a]Compounds were tested at a 1:1 molar ratio (all data are n = 3 except for 2D7 and PRO 140, where n = 2)
[b]Combination Index at $IC_{50}$ value. The mutually exclusive CI formula ($\alpha$ = 0) was utilized for 2D7 in combination with molecules that bind CCR5 (Chou and Rideout, 1991).
[c]Mass of 2D7/mass of other HIV-1 entry inhibitor tested in combination. Molecular weights of inhibitors are: 2D7 ≈ 150,000 g/mole; SCH-D = 538 g/mole; TAK-779 = 531 g/mole (hydrochloride salt); UK-427,857 = 514 g/mole; RANTES ≈ 7,800 g/mole.

Example 2

Combination Testing of PRO 140 with Small Molecule, Peptide and Protein Inhibitors, and HIV-1 in the HIV-1 Pseudovirus Particle (HIV-1pp) Assay Materials and Methods
Preparation of HIV-1 Pseudoparticles:

HIV-1 pseudoparticles (HIV-1pp) are generated in 293T cells by transient coexpression of an HIV-1-based NL4/3luc+env− plasmid and a construct encoding HIV-1$_{JRFL}$ Env. The NL4/3luc+env− plasmid was obtained from the NIH AIDS Research and Reference Reagent Program (Cat. No. 3418), and the HIV-1$_{JRFL}$ Env was inserted into the pcDNA3.1 vector (Invitrogen). Briefly, 293T cells are calcium phosphate transfected with a 1:1 ratio of NL4/3luc+env− reporter vector and Env expression vector in Hepes buffer (Profection Mammalian Transfection Kit, Promega). After 16 h the transfection medium is aspirated and fresh cell culture medium (DMEM with 10% FBS, glutamine and antibiotics) is added and the incubation is continued at 37° C. for an additional 24-32 h. Cell culture supernatants are collected 48 h post-transfection and centrifuged at 1,400 rpm for 10 min to pellet cell debris. The viral supernatant is brought to a final concentration of 5% sucrose and stored aliquoted at −80° C.

Cells:

U87-CD4-CCR5 cells were obtained from the NIH AIDS Research and Reference Program (Cat. No. 4035). These cells are maintained in culture medium (DMEM with 10% FBS; antibiotics and glutamine) containing 0.3 mg/ml G418 and 0.5 mg/ml puromycin. Cells are grown in T175-cm$^2$ flasks at 37° C. and diluted 1:5 every 3-4 days. For assay plate preparation, cells are trypsinized and seeded into wells of 96-well tissue-culture treated flat bottom opaque polystyrene plates (Perkin Elmer, Boston, Mass.) at a density of 3×10$^3$ cells/well. Plates are incubated for no more than 4 h at 37° C. in a humidified 5% $CO_2$ incubator prior to their use in the HIV-1pp susceptibility assay.

Compound Preparation:

Fifty µl of diluted compound at 4× the desired final concentration are added per well. For compounds solubilized in DMSO, the 4× stock will contain 2% DMSO (such that the final DMSO concentration in the assay is always 0.5% for small molecules). Control wells receiving no compound are included on each plate. In addition, an AZT inhibition control is included in each assay. Compounds are tested individually and at a fixed mass or molar ratio over a broad range of concentrations.

Virus Addition:

A vial of frozen, aliquoted HIV-1pp is thawed in a 37° C. waterbath and then placed on wet ice. Virus is diluted in cold cell culture medium as necessary to achieve the desired final virus concentration in the HIV-1pp assay (about 10,000 relative light units (rlu) per well). 50 µl of diluted virus are added per well, bringing the final well volume to 200 µl. A no-virus control (minimum or background luminescence) and a no-compound control (maximum luminescence) are included on each plate. The plates are incubated for 72 h at 37° C. in a humidified 5% $CO_2$ incubator followed by processing for luciferase signal (see below).

Plate Processing for Luciferase Assay:

Assay medium is aspirated and 200 µl of PBS are added to each well. The PBS is aspirated and 501 of 1× Cell Lysis Reagent (Promega—Cat. No. E1531) are added to each well. Assay plates are then frozen for at least 2 h at −80° C. followed by thawing at room temperature and vigorous mixing with an electronic pipettor. 25 µl from each well are transferred to an opaque 96-well plate (Costar #3922). Four replicates are pooled into the same well on the opaque plate. 100 µl of freshly thawed and reconstituted luciferase substrate (Luciferase Assay System, Promega—Cat. No. E1501) are added to each well of the plate with the electronic pipettor, and luminescence is detected immediately on a Dynex MLX plate reader set to medium gain.

Data Analysis:

Neutralization activity is displayed by plotting the percent inhibition of luciferase activity (after background rlu values are subtracted from all datapoints) versus $\log_{10}$ drug concentration. The percent inhibition is derived as follows: [1-(luciferase activity in the presence of drug/luciferase activity in the absence of drug)]×100. $IC_{50}$ values are determined by fitting the inhibition data with a non-linear, four-parameter, variable slope equation (GraphPad Prism, ver. 4.02; GraphPad Software, San Diego, Calif.). Upper and lower inhibition values are constrained to 100% and 0%, respectively for curve fitting.

Synergy Determination:

Cooperative interactions between PRO 140 and small-molecule and peptide-based inhibitors of CCR5, CD4, HIV-1 gp120, HIV-1 gp41 and HIV-1 reverse transcriptase (see Tables 4 and for listing of HIV-1 inhibitors approved for clinical use) are determined as described in Example 1. Cooperative inhibition effects of drug combinations are determined by the method of Chou and Talalay (1984). $IC_{50}$ values are generated for all combinations as described above. Combination Index (CI) and Dose Reduction (DR) values are calculated according to the following formulas:

$$CI = \left[\frac{IC_{50}Dcomb1}{IC_{50}Dsolo1}\right] + \left[\frac{IC_{50}Dcomb2}{IC_{50}Dsolo2}\right] + \alpha\left[\frac{(IC_{50}Dcomb1)(IC_{50}Dcomb2)}{(IC_{50}Dsolo1)(IC_{50}Dsolo2)}\right]$$

DR (for compound 1)=($IC_{50}$ Dsolo1/$IC_{50}$ Dcomb1)
DR (for compound 2)=($IC_{50}$ Dsolo2/$IC_{50}$ Dcomb2)
Where:
"$IC_{50}$ Dcomb1"=$IC_{50}$ of drug 1 in combination with drug 2;
"$IC_{50}$ Dsolo1"=$IC_{50}$ of drug 1 when tested alone;
"$IC_{50}$ Dcomb2"=$IC_{50}$ of drug 2 in combination with drug 1;
"$IC_{50}$ Dsolo2"=$IC_{30}$ of drug 2 when tested alone;
$\alpha$=0 if the effects of the two drugs are mutually exclusive; and
$\alpha$=1 if the effects of the two drugs are mutually nonexclusive.

Combinations with CI<1 are determined to be synergistic, whereas combinations with CI>1 are determined to be antagonistic. Additivity is reflected in combinations for which CI=1.

Example 3

Combination Testing of PRO 140 with Small Molecule, Peptide and Protein Inhibitors in the HIV-1 Authentic Virus Replication Assay Materials and Methods
Preparation of PBMCs:

Replication of authentic HIV-1 is measured in activated peripheral blood mononuclear cells (PBMCs) using the monocyte/macrophage-tropic HIV-1 clone, JRFL (HIV-$1_{JRFL}$), for these studies.

PBMCs are isolated from 4 separate donors (Leukopacks) by centrifugation on a Ficoll gradient. CD8 cells are depleted using RosetteSep CD8 Depletion Cocktail (#15663, StemCell Research, Vancouver, BC). Cells are diluted to $4\times10^6$/ml and added in equal parts to three T175-cm$^2$ flasks and then stimulated by addition of one of the following media: IL-2 Medium [RPMI 1640 (#10-040-CV, Cellgro, Herndon, Va.), 10% FBS (#35-010-CV), 2 mM L-Glutamine (#25-005-CI), 100 U/ml IL-2 (Sigma, St. Louis, Mo.)]; PHA 5 Medium: [IL-2 Medium with 5 ug/ml Phytohemagglutinin PHA-P (PHA) (#L8754, Sigma, St. Louis, Mo.), filtered]; or PHA 0.5 Medium: [IL-2 Medium with 0.5 ug/ml PHA, filtered]. Each flask receives a total of 50-150 ml of medium. Flasks are incubated for 3 days at 37° C. followed by pooling of the contents prior to use in the infection assay.

Virus Titration:

Serial dilutions of virus are tested in quadruplicate on activated PBMCs ($1.4\times10^5$ PBMC/well). Titration Medium [IL-2 Medium with 100 IU/ml penicillin/streptomycin (#30-002-CI, Cellgro)] is utilized for virus titrations. Fifty µl of diluted virus is added to 100 µl of PBMCs in flat bottom, tissue-culture treated 96-well plates (VWR#29442-054, Corning, Corning, N.Y.) and the plates are incubated at 37° C. in a humidified, 5% $CO_2$ incubator. After 7 days, 50 µl are removed from each well and tested for virus levels by p24 antigen ELISA (Perkin Elmer, Boston, Mass.). Virus titer is determined by the method of Reed and Muench (Table 11).

Neutralization Assay:

Stimulated PBMCs are seeded into wells of 96-well flat bottom plates at a density of $1.4\times10^5$ cells/well. Virus is diluted to 2,000 TCIDn/ml and mixed with serial 0.5 $\log_{10}$ dilutions of compound for 1 h at 37° C. prior to addition to the cell plates. The final amount of virus added per well is 100 $TCID_{50}$. The final DMSO concentration in the assay is always 0.5% whenever small molecule inhibitors are being tested. Plates are incubated at 37° C. for 5 days, at which time an aliquot of supernatant is removed for p24 antigen ELISA. If control wells (virus without inhibitor) exhibit low p24 antigen levels then the plates are brought back to full volume with Titration medium and incubated for an additional 24 h.

TABLE 11

Reed and Muench formula for calculating virus titer[a]

| No. of pos. wells | $TCID_{50}$/ml ($10^x$) | No. of pos. wells | $TCID_{50}$/ml ($10^x$) |
|---|---|---|---|
| 1 | 0.74 | 41 | 4.23 |
| 2 | 0.83 | 42 | 4.32 |
| 3 | 0.92 | 43 | 4.41 |
| 4 | 1.00 | 44 | 4.49 |
| 5 | 1.09 | 45 | 4.58 |
| 6 | 1.17 | 46 | 4.67 |
| 7 | 1.26 | 47 | 4.76 |
| 8 | 1.35 | 48 | 4.84 |
| 9 | 1.44 | 49 | 4.93 |
| 10 | 1.52 | 50 | 5.02 |
| 11 | 1.61 | 51 | 5.11 |
| 12 | 1.70 | 52 | 5.19 |
| 13 | 1.79 | 53 | 5.28 |
| 14 | 1.87 | 54 | 5.37 |
| 15 | 1.96 | 55 | 5.46 |
| 16 | 2.05 | 56 | 5.54 |
| 17 | 2.14 | 57 | 5.63 |
| 18 | 2.22 | 58 | 5.72 |
| 19 | 2.31 | 59 | 5.81 |
| 20 | 2.40 | 60 | 5.89 |
| 21 | 2.49 | 61 | 5.98 |
| 22 | 2.57 | 62 | 6.07 |
| 23 | 2.66 | 63 | 6.15 |
| 24 | 2.75 | 64 | 6.24 |
| 25 | 2.83 | 65 | 6.33 |
| 26 | 2.92 | 66 | 6.42 |
| 27 | 3.01 | 67 | 6.50 |
| 28 | 3.10 | 68 | 6.59 |
| 29 | 3.18 | 69 | 6.68 |
| 30 | 3.27 | 70 | 6.77 |
| 31 | 3.36 | 71 | 6.85 |
| 32 | 3.45 | 72 | 6.94 |
| 33 | 3.53 | 73 | 7.03 |
| 34 | 3.62 | 74 | 7.12 |
| 35 | 3.71 | 75 | 7.20 |
| 36 | 3.80 | 76 | 7.29 |
| 37 | 3.88 | 77 | 7.38 |
| 38 | 3.97 | 78 | 7.47 |
| 39 | 4.06 | 79 | 7.55 |
| 40 | 4.15 | 80 | 7.64 |

[a]To calculate virus titer, first multiply the total number of positive wells by 2 (the chart was designed to be used with replicates of 8), then look up the corresponding $TCID_{50}$/mL titer and add 0.7 (the formula requires the addition of a log dilution factor).

Data Analysis:

Neutralization activity is displayed by plotting the percent inhibition of p24 antigen production (after background values are subtracted from all datapoints) versus $\log_{10}$ drug concentration. The percent inhibition is derived as follows [1−(p24 levels in the presence of drug/p24 levels in the absence of drug)]×100. $IC_{50}$ values are determined by fitting the inhibition data with a non-linear, four-parameter, variable slope equation (GraphPad Prism, ver. 4.02; GraphPad Software, San Diego, Calif.). Upper and lower inhibition values are constrained to 100% and 0%, respectively for curve fitting.

Synergy Determinations:

Cooperative interactions between PRO 140 and small-molecule and peptide-based inhibitors of CCR5, CD4, HIV-1 gp120, HIV-1 gp41, HIV-1 reverse transcriptase and HIV-1 protease (Table 8) are determined as described for Example 1. Cooperative inhibition effects of drug combinations are determined by the method of Chou and Talalay (1984). $IC_{50}$ values are generated for all combinations as described above. Combination Index (CI) and Dose Reduction (DR) values are calculated according to the following formulas:

$$CI = \left[\frac{IC_{50}Dcomb1}{IC_{50}Dsolo1}\right] + \left[\frac{IC_{50}Dcomb2}{IC_{50}Dsolo2}\right] + \alpha\left[\frac{(IC_{50}Dcomb1)(IC_{50}Dcomb2)}{(IC_{50}Dsolo1)(IC_{50}Dsolo2)}\right]$$

DR (for compound 1)=($IC_{50}$ Dsolo1/$IC_{50}$ Dcomb1)
DR (for compound 2)=($IC_{50}$ Dsolo2/$IC_{50}$ Dcomb2)
Where:
"$IC_{50}$ Dcomb1"=$IC_{50}$ of drug 1 in combination with drug 2;
"$IC_5$ Dsolo1"=$IC_{50}$ of drug 1 when tested alone;
"$IC_{50}$ Dcomb2"=$IC_{50}$ of drug 2 in combination with drug 1;
"$IC_{50}$ Dsolo2"=$IC_{50}$ of drug 2 when tested alone;
$\alpha$=0 if the effects of the two drugs are mutually exclusive; and
$\alpha$=1 if the effects of the two drugs are mutually nonexclusive.

Combinations with CI<1 are determined to be synergistic, whereas combinations with CI>1 are determined to be antagonistic. Additivity is reflected in combinations for which CI=1.

Discussion

PRO 140 is a CCR5-specific mAb being developed for HIV-1 therapy. It is a humanized IgG4,κ version (see PCT International Publication No. WO 03/072766, published Sep. 4, 2003) of the murine antibody, PA14 (Olson et al., 1999; PCT International Publication No. WO 00/35409, published Jun. 20, 2000), which binds to the CCR5 receptor on the surface of a cell and inhibits CCR5-mediated fusion of HIV-1 to the cell. The studies described herein concern the testing of the antiviral activity of PRO 140 in combination with small-molecule and peptide inhibitors of HIV-1 infection. Data generated from this testing were analyzed for potential cooperative effects on inhibition of HIV-1 infection.

In one series of experiments, inhibition of HIV-1 infection was assayed using a fluorescence resonance energy transfer (RET) assay, which measures the fusion of effector cells (HeLa-Env$_{JRFL}$) expressing recombinant HIV-1 strain JRFL envelope glycoproteins (Env) to target cells (CEM NKR-CCR5) expressing CD4 and CCR5 (Litwin et al., 1996). In this assay, effector cells are labeled with the F18 dye and target cells with the R18 dye. HIV-1 Env-mediated fusion of effector and target cells results in the placement of these two dyes within close proximity in the cell membrane. When F18 is excited at its optimum wavelength (450 nm), it emits light at a wavelength (530 nm) that will excite R18 when the two dyes are co-localized in the same membrane, resulting in R18-specific emission at 590 nm. Drug susceptibility is measured by adding serial concentrations of drugs to target cells prior to addition of effector cells. Inhibition of HIV-L Env-mediated fusion is reflected in a reduction in fluorescence emission due to R18 in a dose-dependent manner, providing a quantitative measure of drug activity.

Initial experiments measuring inhibition of HIV-1 Env-mediated fusion were conducted in order to demonstrate the robustness of the assay system for quantifying cooperative interactions. In these experiments, PRO 140 was run in combination with itself, a combination that should result in combination index (CI) values indicative of additive interactions. Using the methodology of Chou and Talalay (1984), CI values of <1.0, =1.0 and >1.0 are taken to indicate synergistic, additive and antagonistic interactions, respectively. Indeed. PRO 140 run in combination with itself returned a CI value of 0.97±0.08 (n=9; Table 7), indicating that the assay system accurately represented this interaction.

Synergy experiments were then conducted between PRO 140 and 3 small-molecule (SCH-D, TAK-779, UK427857), one peptide (RANTES) and one mAb (2D7) antagonist of CCR5. In addition, cooperative interactions were measured between PRO 140 and T-20 (peptide-based inhibitor of gp41), PRO 542 (protein-based inhibitor of gp120), BMS378806 (small molecule inhibitor of gp120) and Leu-3A (anti-CD4 mAb).

The results (see Table 7) revealed potent synergy between PRO 140 and all 3 small-molecule CCR5 antagonists as well as RANTES. CI values between PRO 140 and these CCR5 antagonists ranged from 0.36±0.10 to 0.59±0.08. Dose reduction values indicated that the compound in combination exerted about a 4-fold effect on PRO 140 activity, whereas the effect of PRO 140 on the compound in combination ranged from about 3- to about 16-fold (Table 7). Modest synergy to additivity was observed between PRO 140 and T-20, PRO 542, BMS-378806 and 2D7 (CI=0.84±0.16, 0.96±0.17, 1.21±0.21, and 0.93±0.04, respectively).

Small molecule antagonists of CCR5 run in combination (SCH-D and TAK-779) returned a mean CI value of 1.12±0.32, indicating a slightly additive interaction (Table 8). Conversely, the combination of the recombinant antibody-like fusion protein PRO 542 with the anti-CD4 mAb, Leu-3A, resulted in a mean CI value of 16.9±0.3, indicating potent antagonism between these two HIV-1 inhibitors (Table 8).

Varying the molar ratios of compounds demonstrated similar patterns of cooperativity. At both 5:1 and 1:5 molar ratios of PRO 140 to SCH-D, TAK-779. UK-427,857 and RANTES, potent synergistic inhibition of HIV-1-Env-mediated entry was observed (Table 9). This represents a broad range of inhibitor mass ratios, from a low of 0.15 to a high of 1,820. CI values between PRO 140 and CCR5 antagonists ranged from 0.52±0.20 to 0.84±0.14. More modest synergy to additivity was observed for combinations of PRO 140 with T-20, PRO 542 or BMS-378806. The results of these investigations identify clearly the potent synergistic activities of PRO 140 with CCR5 antagonists, as well as more modest synergy between PRO 140 and T-20 (see FIG. 4).

The HIV-1 inhibitory activity of the CCR5-specific murine mAb, 2D7, in combination with the small-molecule CCR5 antagonists and with RANTES, was also tested using the fluorescent RET assay. 2D7 was found to act synergistically with these CCR5 antagonists and with RANTES (Table 10). CI values between 2D7 and these CCR5 antagonists ranged from 0.15±0.03 to 0.62±0.04. Dose reduction values indicated that the compound in combination exerted about a 2- to 3-fold effect on 2D7 activity, except for TAK-779 which had an approximately 17-fold effect on 2D7 activity. The effect of 2D7 on the compound in combination ranged from about 2- to about 12-fold (Table 10). As observed previously, PRO 140 and 2D7 in combination were essentially additive or modestly synergistic (CI=0.93±0.04).

These results indicate that synergistic inhibition of HIV-1 Env-mediated cell-cell fusion is observed between multiple mAbs and small molecules that bind to CCR5. This property may be broadly applicable to mAbs that target CCR5, including, for example, the mAb CCR5 mAb004 that has been shown to bind to and antagonize CCR5 and block HIV-1 entry in a cell-cell fusion assay (Roschke et al., 2004). A large and growing number of small molecules have been identified as CCR5 antagonists (see Table 12). Certain of these small molecule CCR5 antagonists may also produce synergistic inhibition of HIV-1 Env-mediated fusion in combination with PRO 140 and other anti-CCR5 mAbs.

An alternative approach for examining synergistic interactions utilizes a virus-cell fusion assay as described previously (Nagashima et al., 2001; Trkola et al., 1998). In this assay an HIV genomic vector (pNLluc$^+$Env$^-$) containing a luciferase reporter gene is pseudotyped with Env from HIV-L$_{JRFL}$. Recombinant pseudotyped virus particles are used to infect U87 cells expressing CD4 and CCR5 (U87-CD4-CCR5). Production of luciferase in target cells is dependent on virus entry and the completion of one round of virus replication. Drug susceptibility is measured by adding serial concentrations of drugs to target cells prior to addition of pseudotyped virus particles. Inhibition of virus entry is reflected in a reduction in luciferase activity in a dose-dependent manner, providing a quantitative measure of drug susceptibility. Since the HIV genomic vector requires expression of functional HIV-1 reverse transcriptase (RT) to drive luciferase expression, this pseudovirus assay is also sensitive to inhibition by nucleotide/nucleoside reverse transcriptase inhibitors (NRTIs) and non-nucleoside reverse transcriptase inhibitors (NNRTIs). As such, the HIV-1pp assay is suitable for examining cooperative interactions between PRO 140 and small-molecule, peptide and protein inhibitors of CCR5, CD4, HIV-1 gp120, HIV-1 gp41 and HIV-1 reverse transcriptase.

TABLE 12

Small-Molecule CCR5 antagonists

| Small-Molecule CCR5 antagonist | Reference |
| --- | --- |
| 1,3,4-trisubstituted pyrrolidines | Kim et al., 2005 |
| Modified 4-piperidinyl-2-phenyl-1-(phenylsulfonylamino)-butanes | Shah et al., 2005 |
| Anibamine•TFA, Ophiobolin C, and 19,20-epoxycytochalasin Q | Jayasuriya et al., 2004 |
| 5-(piperidin-1-yl)-3-phenyl-pentylsulfones | Shankaran et al., 2004a |
| 4-(heteroarylpiperdin-1-yl-methyl)-pyrrolidin-1-yl-acetic acid antagonists | Shankaran et al., 2004b |
| Agents containing 4-(pyrazolyl)piperidine side chains | Shu et al., 2004 |
| Agents containing 4-(pyrazolyl)piperidine side chains. | Shen et al., 2004a; 2004b |
| 3-(pyrrolidin-1-yl)propionic acid analogues | Lynch et al., 2003c |
| [2-(R)-[N-methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)amino]-3-methylbutanoic acid (MRK-1)] | Kumar et al., 2003 |
| 1,3,4 trisubstituted pyrrolidines bearing 4-aminoheterocycle substituted piperidine side chains | Willoughby et al., 2003; Lynch et al., 2003a; Lynch et al., 2003b; Hale et al., 2002 |
| Bicyclic isoxazolidines | Lynch et al., 2002 |
| Combinatorial synthesis of CCR5 antagonists | Willoughby et al., 2001 |
| Heterocycle-containing compounds | Kim et al., 2001b |
| Antagonists containing hydantoins | Kim et al., 2001a |
| 1,3,4 trisubstituted pyrrolidines | Hale et al., 2001 |
| 1-[N-(methyl)-N-(phenylsulfonyl)amino]-2-(phenyl)-4-(4-(N-(alkyl)-N-(benzyloxycarbonyl)amino)piperidin-1-yl)butanes | Finke et al., 2001 |
| Compounds from the plant *Lippia alva* | Hedge et al., 2004 |
| Piperazine-based CCR5 antagonists | Tagat et al., 2004 |
| Oximino-piperidino-piperidine-based CCR5 antagonists | Palani et al., 2003b |
| Rotamers of SCH 351125 | Palani et al., 2003a |
| Piperazine-based symmetrical heteroaryl carboxamides | McCombie et al., 2003 |
| Oximino-piperidino-piperidine amides | Palani et al., 2002 |
| Sch-351125 and Sch-350634 | Este, 2002 |
| SCH-C | Strizki et al., 2001 |
| 1-[(2,4-dimethyl-3-pyridinyl)carbonyl]-4-methyl-4-[3(S)-methyl-4-[1(S)-[4-(trifluoromethyl)phenyl]ethyl]-1-piperazinyl]-piperidine N1-oxide (Sch-350634) | Tagat et al., 2001a |
| 4-[(Z)-(4-bromophenyl)-(ethoxyimino)methyl]-1'-[(2,4-dimethyl-3-pyridinyl)carbonyl]-4'-methyl-1,4'-bipiperidine N-oxide (SCH 351125) | Palani et al., 2001 |
| 2(S)-methyl piperazines | Tagat et al., 2001b |
| Piperidine-4-carboxamide derivatives | Imamura et al., 2005 |
| 1-benzazepine derivatives containing a sulfoxide moiety | Seto et al., 2005 |
| anilide derivatives containing a pyridine N-oxide moiety | Seto et al., 2004a |
| 1-benzothiepine 1,1-dioxide and 1-benzazepine derivatives containing a tertiary amine moiety | Seto et al., 2004b |
| N-[3-(4-benzylpiperidin-1-yl)propyl]-N,N'-diphenylureas | Imamura et al., 2004a |
| 5-oxopyrrolidine-3-carboxamide derivatives | Imamura et al., 2004b |
| Anilide derivatives with a quaternary ammonium moiety | Shiraishi et al., 2000 |
| AK602/ONO4128/GW873140 | Nakata et al., 2005 |
| Spirodiketopiperazine derivatives | Maeda et al., 2001; Maeda et al., 2004 |
| Selective CCR5 antagonists | Thoma et al., 2004 |

A third approach for examining antiviral synergy utilizes a whole virus assay. Cooperativity between all classes of inhibitor molecules can be examined in this assay format.

In both the virus-cell fusion luciferase assay and the whole virus assay, $IC_{50}$ values are generated for all combinations as described herein for the RET assay. Cooperative inhibition effects of drug combinations are determined by the method of Chou and Talalay (1984).

PRO 140 broadly and potently inhibited CCR5-mediated HIV-1 entry without CCR5 antagonism or other immunologic side effects in preclinical testing. More recently, PRO 140 has demonstrated favorable tolerability, PK and immunologic profiles in preliminary results from an ongoing Phase 1a study in healthy volunteers. Thus, in many respects, PRO 140 offers a novel and attractive product profile for anti-HIV-1 therapy. Moreover, the activities of anti-CCR5 mAbs are fundamentally distinct from, but complementary to, those of small-molecule CCR5 antagonists (see Table 2).

It might have been expected that combinations of anti-CCR5 mAbs and non-antibody CCR5 antagonists would produce additive effects in inhibiting fusion of HIV-L to $CD4^+CCR5^+$ target cells since both classes of agents bind to the same target molecule. Surprisingly, however, the data presented herein reveal that anti-CCR5 mAbs, exemplified by PRO 140 and 2D7, exhibited potent and reproducible synergy with non-antibody CCR5 antagonists, exemplified by SCH-D, TAK-779, UK-427,857 and RANTES, in inhibiting HIV-1 Env-mediated cell-cell fusion. Synergies routinely translated into 4- to 10-fold dose reductions, suggesting significant improvement in inhibitory potency for the drug combinations. In contrast, purely additive effects were observed for combinations of non-antibody CCR5 antagonists. These findings likely reflect the different patterns of CCR5 recognition of these molecules: whereas small-molecule CCR5 antagonists bind a common hydrophobic pocket within the transmembrane domains of CCR5, PRO 140 recognizes a hydrophilic, extracellular epitope of CCR5. Overall, the data support the use of PRO 140 in combination with non-antibody HIV-1 entry inhibitors and suggest that PRO 140 represents a distinct subclass of CCR5 inhibitor.

Moreover, the available data suggest that the observed synergy may also be exhibited by combinations involving anti-CCR5 mAbs other than PRO 140, including, but not limited to, mAb CCR5mAb004 (Roschke et al., 2004), as well as non-antibody CCR5 antagonists other than SCH-D, TAK-779, UK-427,857 and RANTES. Thus, these antibodies likely produce synergistic effects in combination with GW873140 (Lalezari et al., 2004), TAK-652 (Baba et al., 2005), and at least certain of the small-molecule CCR5 antagonists listed in Table 12. Accordingly, combination therapy comprising administration of anti-CCR5 mAbs and non-antibody CCR5 antagonists may offer powerfully effective, new approaches to preventing and treating HIV-1 infection. It is expected that such therapy will result in more potent and more durable ant-HIV-1 treatments. Additionally, the synergistic effects described herein may enable a reduction in dosages of drugs administered to a subject as well as a reduction in dosing frequency.

Example 4

Loading and Maintenance Dose Regimens

The loading regimen, which can, for example, be more dose-intensive than the maintenance regimen, can, for example, have the following characteristics:

Number of doses: 1 or more (up to about 5 doses). Dose level: About 25%, 50%, 75%, 100%, 150% or 200% greater than the maintenance dose regimen. Dose frequency: About 1.5×, 2×, 3× or 4× more frequently than the maintenance dose regimen.

As an example, if the maintenance dose regimen is 2 mg/kg every two weeks, the loading dose regimen could comprise weekly 2 mg/kg doses. Alternatively, the loading dose regimen could comprise a single 4 mg/kg dose or multiple 4 mg/kg doses at weekly or biweekly intervals.

The loading dose regimen can be designed, for example, so as to accelerate the achievement of a pharmacokinetic steady state in the subject, as defined by uniform peak and trough blood concentrations of drug between doses. A preferred loading dose regimen can be determined by routine experimentation wherein the drug is administered to the subject by differing loading and maintenance regimens, and blood levels of drug are measured.

Also, in another embodiment, PRO 140 is administered according to a fixed-dose regimen such as, for example, 75 mg, 150 mg, 300 mg and 600 mg per administration.

Part III

Materials And Methods
Inhibitors

PRO 140 was expressed in mammalian cells and purified by protein A, ion exchange and hydroxyapatite chromatographies. UK-427,857 (Doff et al. 2005), SCH-D (Tagat et al. 2004), TAK-779 (Baba et al. 1999), enfuvirtide (T-20 (Wild et al. 1992); BMS-378806 (Lin et al. 2003)) and PRO 542 (CD4-IgG2, (Allaway et al. 1995)) were prepared according to published methods. Zidovudine (azidothymidine, AZT), RANTES, the CCR5 mAb 2D7 and the CD4 mAb Leu-3A were purchased from Sigma Chemicals (St. Louis, Mo.), R&D Systems (Minneapolis, Minn.), Pharmingen (San Diego, Calif.), and Becton Dickinson (Franklin Lakes, N.J.), respectively. UK-427,857 and SCH-D were radiolabeled with tritium by GE Healthcare (Piscataway, N.J.), and PRO 140 was conjugated to phycoerythrin (PE) by Southern Biotech, Inc. (Birmingham, Ala.).

HIV-1 Membrane Fusion Assay:

HIV-1 envelope-mediated membrane fusion was examined using a fluorescence resonance energy transfer (RET) assay (Litwin et al. 1996) with modifications. Briefly, HeLa cells that stably express HIV-$1_{JR-FL}$ gp120/gp41 (Litwin et al. 1996) and CEM.NKR-CCR5 cells (NIH AIDS Research and Reference Reagent Program, (Spenlehauer et al. 2001; Trkola et al. 1999)) were labeled separately overnight with fluorescein octadecyl ester (F18; Molecular Probes, Eugene, Oreg.) and rhodamine octadecyl ester (R18; Molecular Probes), respectively. Cells were washed in phosphate-buffered saline containing 15% fetal bovine serum (PBSF) and co-seeded at 15,000 cells/well into a 384-well plate. Inhibitors were added, and the plates were incubated in PBSF plus 0.5% dimethlysulfoxide (DMSO) for 4 h at 37° C. prior to measurement of RET using a Victor$^2$ plate reader (Perkin-Elmer, Boston, Mass.) as previously described (Litwin et al. 1996). The CD4 mAb Leu3a was used as a control inhibitor, and percent inhibition was calculated as: (RET in the absence of inhibitor−RET in the presence of inhibitor)/(RET in the absence of inhibitor−RET in the presence of Leu3a)×100.

HIV-1 Pseudovirus Assay:

A self-inactivating (SIN) vector was derived from the pNL4-3ΔEnv-luciferase vector (Dragic et al. 1996) by deleting 507 basepairs in the U3 region of the 3' long terminal repeat (LTR) so as to remove the TATA box and transcription factor binding sites. The human cytomegalovirus promoter was inserted upstream of the luciferase (luc) gene to enable expression of luciferase following integration.

Reporter viruses pseudotyped with HIV-1$_{JR-FL}$ or HIV-1$_{SF162}$ envelopes were generated by cotransfection of 293T cells with the SIN vector and the appropriate pcDNA env-expressing vector as previously described (Dragic et al. 1996). U87-CD4-CCR5 cells (8,000/well; NIH AIDS Research and Reference Reagent Program) were infected with 125-375 pg of HIV-L pseudoviruses in 384-well plates in the presence or absence of inhibitor(s). Cultures were incubated for 72 h at 37° C. in DMEM containing 10% fetal bovine serum, 1 mg/mL puromycin, 0.3 mg/mL geneticin, antibiotics, and 0.5% DMSO. Luciferase activity (relative light units or RLU) was measured using BrightGlo reagent (Promega, Madison, Wis.) according to the manufacturer's instructions. Percent inhibition was calculated as: (1−RLU in the presence of inhibitor/RLU in the absence of inhibitor)×100. IC50 and IC90 were used to denote the respective concentrations required for 50% and 90% inhibition of HIV-1.

Synergy Determinations:

Experimental design and data analysis were based on the combination index (CI) method (Chou et al. 1991; Chou et al. 1984). Compounds were tested individually and in combination at a fixed molar ratio over a range of serial dilutions. Entry inhibitors were combined in equimolar amounts, whereas a 1:10 molar ratio was used for PRO 140 in combination with azidothymidine and nevirapine. Dose-response curves were fit using a four-parameter sigmoidal equation with upper and lower inhibition values constrained to 100% and 0%, respectively, in order to calculate concentrations required for 50% (IC50) and 90% (IC90) inhibition (GraphPad Prism, GraphPad Software, San Diego, Calif.). CI values for 50% (CI50) and 90% (CI90) inhibition were calculated as previously described (Chou et al. 1991; Chou et al. 1984). The mutually exclusive CI formula was used for combinations of CCR5 inhibitors, while the mutually non-exclusive formula was utilized for combinations of inhibitors to distinct targets (Chou et al. 1991). Each test was conducted 4-12 times. Synergy, additivity and antagonism are indicated by CI<1, CI=1 and CI>1, respectively.

Competition Binding Assays:

To examine inhibition of PRO 140 binding, CEM.NKR-CCR5 cells were suspended in phosphate-buffered saline with 0.1% sodium azide (PBSA) and incubated with varying concentrations of unlabeled CCR5 antagonists at ambient temperature for 30 minutes. Azide was added to block CCR5 internalization during the assay. Cells were washed in PBSA and incubated with 5 nM PRO 140-PE for an additional 30 minutes prior to washing and analysis by flow cytometry using a FACSCalibur instrument (Becton Dickinson). The extent of PRO 140-PE binding was measured in terms of both the mean fluorescence intensity (MFI) and the percent of cells gated for positive staining.

To examine inhibition of UK-427,857 binding, CEM.NKR-CCR5 cells were pre-incubated with unlabeled CCR5 inhibitors as described above prior to addition of 2 nM $^3$H-UK-427,857 for an additional 30 minutes. The cells were washed in PBSA and lysed with 0.5N HCl prior to scintillation counting using a Wallac1410 instrument. An additional study reversed the order of addition in order to examine the stability of UK-427,857 binding over the course of the assay. Cells were pre-incubated with 2 nM $^3$H-UK-427,857 for 30 min prior to washing, addition of unlabeled inhibitors, and processing as described above. EC50 and EC90 were used to denote the concentrations of unlabeled compound required to inhibit binding of labeled compound by 50% and 90%, respectively.

Statistical Analyses:

Two-tailed t-tests were used to test mean CI50 and CI90 values for the null hypothesis $H_0$: CI=1 (additivity) using GraphPad Prism software. P values were corrected for multiple comparisons from α=0.05 according to the Bonferroni method (Cudeck and O'Dell 1994), excluding the PRO 140/PRO 140 mock combination that was included as an assay control. In the Bonferroni correction, P=α/n, where n is the number of comparisons. Twenty-two synergy comparisons (11 compounds×2 CI values) were made based on data generated in the membrane fusion assay, resulting in a corrected P value of 0.0023. In the pseudovirus assay, 32 synergy comparisons (8 compounds×2 viruses×2 CI values) resulted in a corrected P value of 0.0016.

Results

Figure 15:
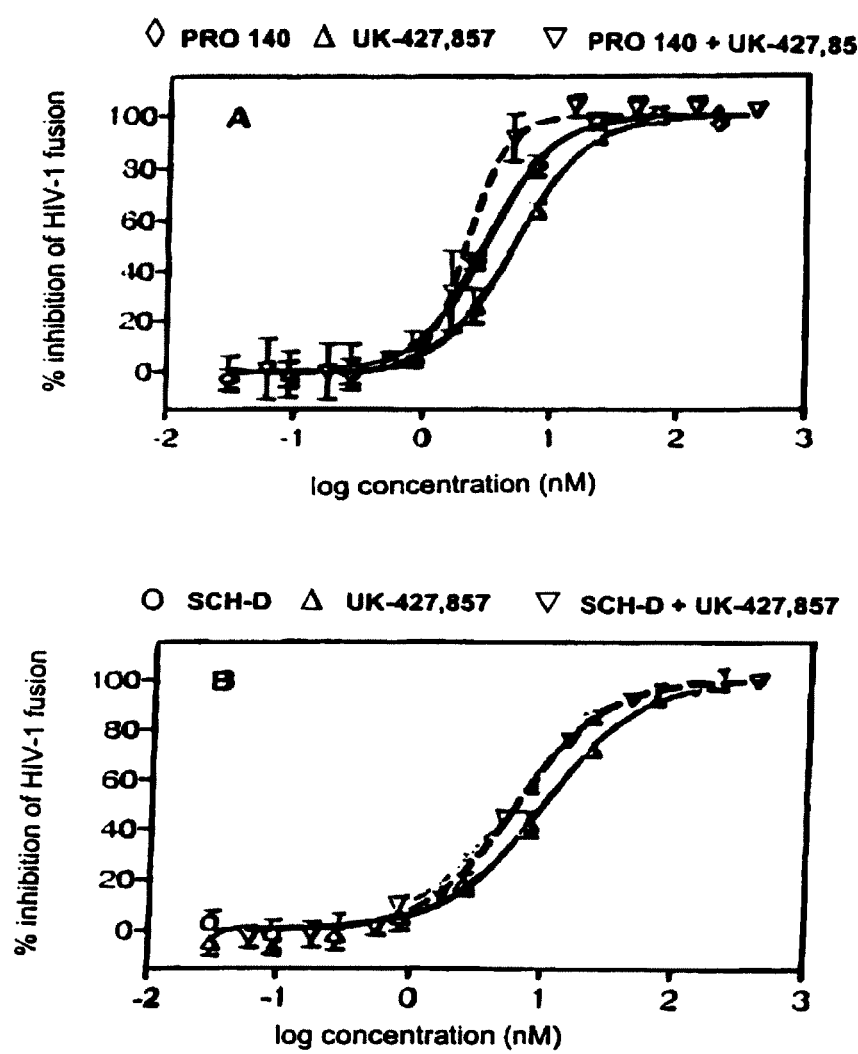
FIG. 15: Dose-response curves for inhibition of HIV-1$_{JR-FL}$ envelope-mediated membrane fusion by combinations of CCR5 inhibitors. Dilutions were analyzed in triplicate wells, and the data points depict the mean and standard deviations of replicates. (A) PRO 140 and UK-427,857 were tested individually and in a 1:1 fixed molar ratio over the indicated range of concentrations. In the experiment depicted, IC50 and IC90 values were 2.9 nM and 111 nM for PRO140, 5.0 nM and 21 nM for UK-427,857, and 2.1 nM and 4.6 nM for the combination. CI50 and CI90 values were 0.58 and 0.32, respectively. (B) SCH-D and UK-427,857 were tested individually and in a 1:1 fixed molar ratio over the indicated range of concentrations. In the experiment depicted, IC50 and IC90 values were 5.5 nM and 34 nM for SCH-D, 9.7 nM and 59 nM for UK-427,857, and 6.1 nM and 31 nM for the combination. CI50 and CI90 values were 0.87 and 0.73, respectively.

Inhibition of HIV-1 Membrane Fusion:

PRO 140 and UK-427,857 were used individually and together to inhibit HIV-1$_{JR-FL}$ envelope-mediated membrane fusion in the RET cell-cell fusion assay, and representative dose-response curves for the individual agents and combination are illustrated in FIG. 15A. Although both PRO 140 and UK-427,857 individually blocked HIV-1 fusion at low nanomolar potency, the combination was markedly more potent. In this assay, 50% inhibition was obtained using 2.9 nM PRO 140 alone, 5.0 nM UK-427,857 used alone, or 2.1 nM of the combination (1.05 nM PRO 140 plus 1.05 nM UK-427,857). This supra-additive effect is indicative of antiviral synergy between the two agents. In contrast, the combination of SCH-D and UK-427,857 was no more potent than individual agents (FIG. 15B). In this example, the dose-response curves for the individual inhibitors and the combination were overlapping, with 50% inhibition requiring 9.7 nM UK-427,857, 5.5 nM SCH-D and 6.1 nM of the combination. The data suggest purely additive effects for these inhibitors.

These studies were extended to additional CCR5 (TAK-779, RANTES and 2D7), gp120 (BMS-378806 and PRO 542) and gp41 (enfuvirtide) inhibitors, and were repeated four or more times for each condition. CI50 and CI90 values were calculated for each condition and averaged across the independent assays. Cooperativity was assessed using t-tests to determine if the CI50 and CI90 values were significantly different from one. As a test of these methods, a PRO 140/PRO 140 mock combination was examined by adding PRO 140 to the assay wells in two separate additions. CI50 and CI90 values for the PRO 140/PRO 140 combination were 0.96 and 0.97, respectively (Table 13); therefore, purely additive effects were observed for this mock combination, as expected.

TABLE 13

CI values for inhibition of HIV-1$_{JR-FL}$ envelope-mediated membrane fusion[a]

| 1$^{st}$ Inhibitor | Target | IC50, nM | IC90, nM | 2$^{nd}$ Inhibitor | CI50 | P value | CI90 | P value |
|---|---|---|---|---|---|---|---|---|
| PRO 140 | CCR5 | 2.5 | 8.6 | PRO 140 | 0.97 ± 0.07 | 0.13 | 0.96 ± 0.14 | 0.37 |
| UK-427,857 | CCR5 | 5.3 | 27 | PRO 140 | *0.61 ± 0.05* | *<0.0001* | *0.40 ± 0.06* | *<0.0001* |
| SCH-D | CCR5 | 3.2 | 16 | PRO 140 | *0.51 ± 0.05* | *<0.0001* | *0.36 ± 0.06* | *<0.0001* |
| TAK-779 | CCR5 | 11 | >200 | PRO 140 | *0.38 ± 0.08* | *<0.0001* | N/A | N/A |
| RANTES | CCR5 | 2.4 | 38 | PRO 140 | *0.59 ± 0.08* | *0.0022* | *0.43 ± 0.05* | *0.0002* |
| RANTES | CCR5 | 2.4 | 38 | UK-427,857 | *0.48 ± 0.03* | *0.0017* | *0.18 ± 0.01* | *<0.0001* |
| SCH-D | CCR5 | 3.2 | 16 | UK-427,857 | 0.86 ± 0.03 | 0.016 | 0.75 ± 0.02 | 0.0033 |
| SCH-D | CCR5 | 3.2 | 16 | TAK-779 | 1.3 ± 0.18 | 0.12 | N/A | N/A |
| 2D7 | CCR5 | 3.7 | 58 | PRO 140 | 1.0 ± 0.14 | 0.61 | 1.9 ± 0.61 | 0.024 |
| enfuvirtide | gp41 | 8.6 | 66 | PRO 140 | 0.84 ± 0.16 | 0.040 | 0.89 ± 0.20 | 0.19 |
| PRO 542 | gp120 | 8.9 | 91 | PRO 140 | 0.96 ± 0.17 | 0.56 | 0.94 ± 0.19 | 0.45 |
| BMS-378806 | gp120 | 5.2 | 20 | PRO 140 | *1.3 ± 0.19* | *0.0015* | 1.1 ± 0.22 | 0.19 |

[a]Statistically significant results (P < 0.0023 after application of the Bonferroni correction for multiple comparisons) are indicated in italicized bold text.
IC50 and IC90 denote values for the 1$^{st}$ inhibitor.
N/A = not applicable;
TAK-779 did not consistently achieve 90% inhibition in the assay.
CI values represent the means and standard deviations of 4-12 independent assay.

Potent synergy was observed for PRO 140 in combination with each of three small-molecule CCR5 antagonists (UK-427,857, SCH-D and TAK-779), and the findings were statistically significant even when the data were corrected for multiple comparisons via the Bonferroni method (Table 13). CI values ranged from 0.36 to 0.61, and these synergies translated into dose reductions ranging from 3- to 8-fold across the different conditions. Synergies were greater at 90% inhibition than at 50% inhibition. Synergy between PRO 140 and small-molecule CCR5 antagonists was robust in that it was observed at both the 50% and 90% inhibition levels in every instance. The exception was TAK-779, which did not mediate 90% inhibition when used individually, and therefore a CI90 was not determined. Similarly potent synergy was observed when RANTES was used in combination with either PRO 140 or UK-427,857 (Table 13). Additional tests examined combinations of two small-molecule CCR5 antagonists (SCH-D/UK-427,857 and SCH-D/TAK-779) or two CCR5 mAbs (PRO 140/2D7). No significant synergy was observed for these combinations, although the SCH-D/UK-427,857 CI90 values trended towards significance. The findings are consistent with prior observations of overlapping binding sites for PRO 140 and 2D7 (Olson et al. 1999) and for SCH-D and TAK-779 (Seibert et al. 2006). PRO 140 was also tested in combination with the gp41 fusion inhibitor enfuvirtide and with the gp120 attachment inhibitors PRO 542 and BMS-378806 (Table 13). CI values ranged from 0.84 to 1.28, and none of these combinations demonstrated synergy that met the criteria for statistical significance. For the PRO 140/BMS-378806 combination, modest antagonism was observed at 50% but not 90% inhibition. The biological significance of this result is unclear.

Inhibition of HIV-1 Psendoviruses:

Single-cycle HIV-1 reporter viruses were used to examine whether the synergistic effects were limited to cell-cell fusion or whether they extended to other modes of HIV-1 entry. Signals in this assay require both viral entry and reverse transcription, so that both NRTI and NNRTI may be included in the analyses. Each combination was tested against reporter viruses pseudotyped with envelopes from HIV-1$_{JR-FL}$ and HIV-1$_{SF162}$ in at least 4 independent assays per virus. A PRO 140/PRO 140 mock combination was again included as an assay control, and demonstrated additive effects against both HIV-1$_{JR-FL}$ and HIV-1$_{SF162}$ pseudoviruses, as expected (Table 14).

PRO 140 potently synergized with both UK-427,857 and SCH-D in blocking virus-cell fusion, and the results met the criteria for statistical significance. Comparable levels of synergy were observed against both HIV-1$_{JR-FL}$ and HIV-1$_{SF162}$ pseudoviruses at 50% and 90% inhibition (Table 14), with CI values ranging from 0.18 to 0.64. These synergies translated into dose reductions ranging to 14-fold. These results are in good agreement with those obtained in the cell-cell fusion assay (Table 13). Neither TAK-779 nor RANTES mediated consistent, high-level inhibition of HIV-1 pseudovirus entry, and therefore these compounds were not included in this analysis (data not shown).

TABLE 14

CI values for inhibition of HIV-1 reporter viruses pseudotyped with envelopes from HIV-1$_{JR-FL}$ and HIV-1$_{SF162}$.[a]

| 1$^{st}$ Inhibitor | Target | HIV-1 Envelope | IC50, nM | IC90, nM | 2$^{nd}$ Inhibitor | CI50 | P value | CI90 | P value |
|---|---|---|---|---|---|---|---|---|---|
| PRO 140 | CCR5 | JRFL | 2.2 | 28 | PRO 140 | 1.2 ± 0.32 | 0.16 | 0.90 ± 0.15 | 0.047 |
|  |  | SF162 | 1.3 | 20 | PRO 140 | 1.0 ± 0.27 | 1.0 | 0.86 ± 0.33 | 0.21 |
| SCH-D | CCR5 | JRFL | 2.4 | 44 | PRO 140 | *0.47 ± 0.15* | *<0.001* | *0.18 ± 0.04* | *<0.001* |
|  |  | SF162 | 0.34 | 14 | PRO 140 | *0.60 ± 0.17* | *<0.001* | *0.28 ± 0.11* | *<0.001* |
| UK-427,857 | CCR5 | JRFL | 7.4 | 46 | PRO 140 | *0.44 ± 0.06* | *<0.001* | *0.24 ± 0.11* | *<0.001* |
|  |  | SF162 | 0.87 | 13 | PRO 140 | *0.64 ± 0.07* | *<0.001* | *0.31 ± 0.11* | *<0.001* |
| UK-427,857 | CCR5 | JRFL | 7.4 | 46 | SCH-D | 0.71 ± 0.11 | 0.16 | 1.2 ± 0.15 | 0.32 |
|  |  | SF162 | 0.87 | 13 | SCH-D | 0.87 ± 0.06 | 0.19 | 0.86 ± 0.28 | 0.61 |

TABLE 14-continued

CI values for inhibition of HIV-1 reporter viruses pseudotyped with envelopes from HIV-1$_{JR-FL}$ and HIV-1$_{SF162}$.[a]

| 1$^{st}$ Inhibitor | Target | HIV-1 Envelope | IC50, nM | IC90, nM | 2$^{nd}$ Inhibitor | CI50 | P value | CI90 | P value |
|---|---|---|---|---|---|---|---|---|---|
| 2D7 | CCR5 | JRFL | 8.8 | >200 | PRO 140 | 1.5 ± 0.25 | 0.024 | N/A | N/A |
|  |  | SF162 | 2.2 | 74 | PRO 140 | 1.1 ± 0.47 | 0.61 | 1.0 ± 0.16 | 0.65 |
| PRO 542 | Gp120 | JRFL | 0.19 | 2.9 | PRO 140 | 1.2 ± 0.32 | 0.22 | 1.0 ± 0.18 | 0.92 |
|  |  | SF162 | 0.36 | 7.1 | PRO 140 | 0.98 ± 0.28 | 0.84 | 0.64 ± 0.26 | 0.010 |
| BMS-378806 | Gp120 | JRFL | 1.2 | 11 | PRO 140 | 1.2 ± 0.38 | 0.43 | 0.74 ± 0.23 | 0.059 |
|  |  | SF162 | 0.03 | 0.42 | PRO 140 | 1.1 ± 0.28 | 0.36 | 0.82 ± 0.21 | 0.068 |
| nevirapine | RT | JRFL | 30 | 310 | PRO 140 | 1.2 ± 0.38 | 0.36 | 0.73 ± 0.28 | 0.068 |
|  |  | SF162 | 42 | 280 | PRO 140 | 1.2 ± 0.34 | 0.30 | 0.63 ± 0.19 | 0.033 |
| zidovudine | RT | JRFL | 140 | 1900 | PRO 140 | 1.1 ± 0.38 | 0.37 | 0.85 ± 0.26 | 0.21 |
|  |  | SF162 | 86 | 2100 | PRO 140 | 0.99 ± 0.27 | 0.91 | 1.0 ± 0.38 | 1.0 |

[a]Statistically significant results (P < 0.0016 after application of the Bonferroni correction for multiple comparisons) are indicated in italicized bold text.
IC50 and IC90 refer to values for the 1$^{st}$ inhibitor.
NA = not applicable;
2D7 did not consistently achieve 90% inhibition in the assay.
CI values represent the means and standard deviations of 4 or more independent assays Additive effects were observed for both the UK-427,857/SCH-D and PRO 140/2D7 combinations (Table 14). Similarly, additivity was observed for PRO 140 used in combination with the gp120 inhibitors PRO 542 and BMS-378806. No antagonism was observed for the PRO 140/BMS-378806 combination against either virus. Overall, these findings are consistent with those seen for cell-cell fusion. Lastly, additive effects were observed for PRO 140 in combination with either zidovudine (NRTI) or nevirapine (NNRTI).

Competition Binding Studies:

As described above, additive antiviral effects were observed for inhibitors known (PRO 140 and 2D7) or inferred (UK-427,857 and SCH-D) to compete for CCR5 binding; however, little is known regarding the competitive binding of synergistic compounds (e.g. PRO 140/UK-427,857 and PRO 140/SCH-D). Since non-competitive binding provides a possible mechanism for synergy between CCR5 inhibitors, this issue was explored using labeled forms of UK-427,857 and PRO 140.

Flow cytometry was used to examine inhibition of PRO 140-PE binding to CEM.NRK.CCR5 cells by unlabeled PRO 140, UK-427,857 and SCH-D. PRO 140-PE binding was efficiently inhibited by unlabeled PRO 140, as expected. Complete inhibition was observed in terms of both MFI values (FIG. 16A) and the percent of cells gated for positive binding (FIG. 16B). The EC50 based on MFI data was 2.5 nM (FIG. 16A), and this value compares favorably with the antiviral IC50 of PRO 140 (Tables 13 and 14). Since percent cells gated is a readout for essentially complete inhibition of binding, an EC90 value was calculated as 17 nM, and this value is similar to the antiviral IC90 values observed for PRO 140 (Tables 13 and 14). 2D7 also completely inhibited binding of PRO 140-PE to CEM.NKR-CCR5. The CCR5 specificity of PRO 140-PE was also demonstrated by its inability to bind parental CEM.NKR cells.

Figure 16:
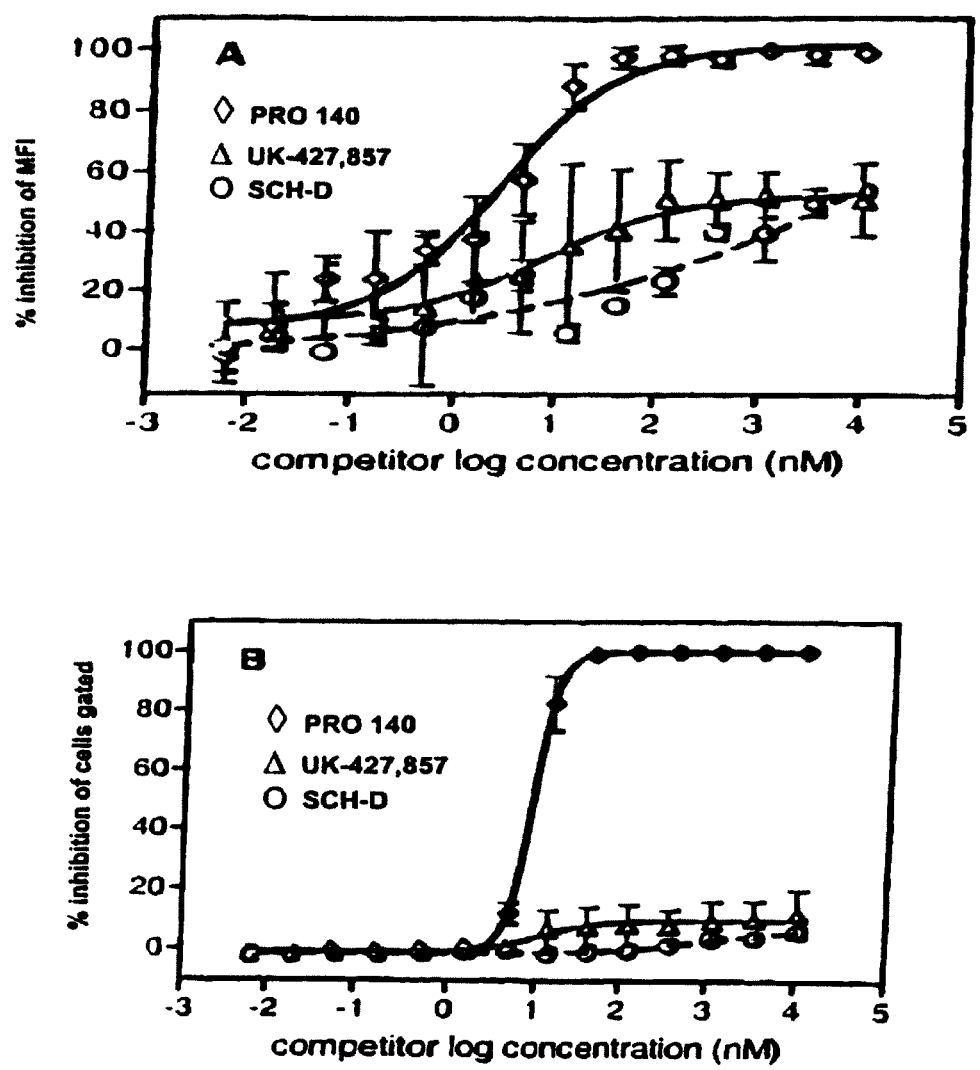
FIG. 16: Inhibition of PRO 140-PE binding to CEM.NKR-CCR5 cells by unlabeled PRO 140, UK-427,857 and SCH-D. CEM.NKR-CCR5 cells were incubated with varying concentrations of unlabeled PRO 140, UK-427,857 or SCH-D for 30 min at room temperature in PBSA buffer prior to addition of 5 nM PRO 140-PE for an additional 30 min. Cells were washed and then analyzed by flow cytometry for both the mean fluorescence intensity (MFI) of binding and the percent of cells gated for positive binding of PRO 140-PE. Inhibition was assessed on the basis of both MFI (A) and percent cells gated (B).

In sharp contrast, modest levels of inhibition were observed for UK-427,857 and SCH-D (FIG. 16). Micromolar concentrations of UK-427,857 and SCH-D reduced PRO 140-PE MFI values by 50% or less (FIG. 16A). More dramatically, UK-427,857 and SCH-D had little impact on the percent of cells gated for positive binding of PRO 140-PE (FIG. 16B). The findings suggest that UK-427,857 and SCH-D partially reduce the number of PRO 140-PE molecules bound per cell; however, these compounds do not reduce the number of cells that bind measurable amounts of PRO 140-PE.

Therefore, UK-427,857 and SCH-D represent partial antagonists of PRO 140 binding, and this finding provides a mechanism for the antiviral synergy observed between PRO 140 and these small-molecule CCR5 antagonists.

Figure 17:
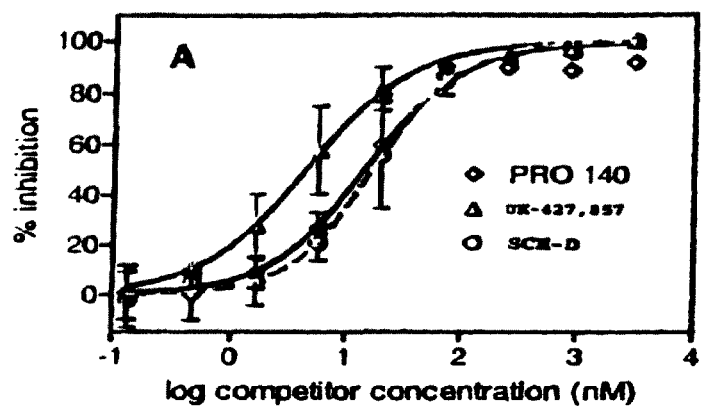
FIG. 17: Inhibition of $^3$H-UK-427,857 binding by unlabeled UK-427,857, SCH-D and PRO 140. (A) CEM.NKR-CCR5 cells were pre-incubated with varying concentrations of unlabeled UK-427,857, SCH-D or PRO 140 for 30 min in PBSA buffer at ambient temperature prior to the addition of at 2 nM $^3$H-UK-427,857 for an additional 30 min. Cells were washed and then analyzed for radioactivity by scintillation counting. (B) The stability of UK-427,857 binding under the assay conditions was examined by pre-incubating CEM.NKR-CCR5 cells with 2 nM $^3$H-UK-427,857 prior to washing, addition of unlabeled compounds for 30 min, and processing as described above.
Figure 17:
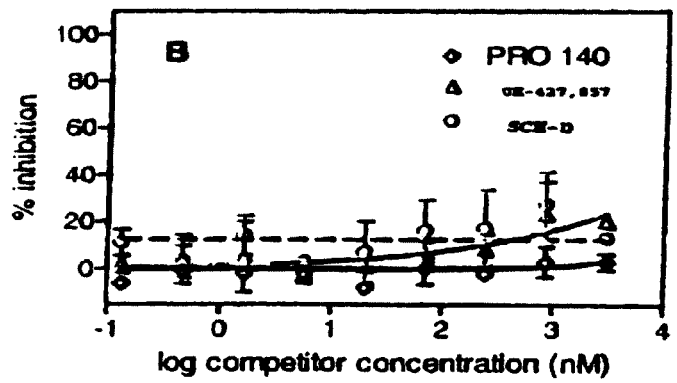

Inhibition of $^3$H-UK-427,857 binding by unlabeled UK-427,857, SCH-D and PRO 140 was next examined. Binding of $^3$H-UK-427,857 to CEM.NKR-CCR5 cells was efficiently inhibited by unlabeled UK-427,857 (FIG. 17A). The EC50 for binding was 4.3 nM and is similar to the antiviral IC50 values observed for UK-427,857 (Tables 13 and 14).

SCH-D also blocked $^3$H-UK-427,857 binding to background levels (FIG. 17A). However, there was no correlation between the compounds' antiviral potency and their potency in blocking $^3$H-UK-427,857 binding. For example, whereas SCH-D demonstrated equal or slightly greater antiviral potency than UK-427.857 (Tables 13 and 14), SCH-D was less potent in blocking $^3$H-UK-427,857 binding (EC50=17 nM, FIG. 17A). This result is consistent with minor differences in the CCR5 binding sites of these compounds.

Surprisingly, PRO 140 also blocked $^3$H-UK-427,857 binding to background levels (FIG. 17A), and this result contrasts with the modest inhibition of PRO 140-PE binding by UK-427,857 (FIG. 16). PRO 140 inhibited $^3$H-UK-427,857 binding with an EC50 of 14 nM, which is 5-10 fold higher than the antiviral IC50 of PRO 140 (Tables 13 and 14).

A final experiment examined the stability of UK-427,857 binding to CEM.NKR-CCR5 cells under the conditions of the competition assay. For this, cells were pre-incubated with $^3$H-UK-427,857 and then the dissociation was examined in the presence of unlabeled UK-427,857, SCH-D and PRO 140. As indicated in FIG. 17B, there was minimal dissociation of $^3$H-UK-427,857 over 30 min at ambient temperature, and UK-427,857 wasn't displaced by either PRO 140 or SCH-D. Therefore, the inability of UK-427,857 to efficiently compete PRO 140 binding to CCR5 (FIG. 16) is not due to rapid dissociation of UK-427,857 from CCR5 during the course of the assay. Collectively, the data indicate that PRO 140 can bind CCR5 in the presence of pre-bound UK-427,857.

Discussion

This study explores interactions between mAb and small-molecule CCR5 inhibitors and examines combinations of CCR5 drugs that currently are in development for HIV-1 therapy. Surprisingly, potent antiviral synergy between the CCR5 mAb PRO 140 and each of three structurally distinct small-molecule CCR5 antagonists was observed. Consistent, high-level synergy was observed across varying assay systems, viral isolates, target cells and inhibition levels. PRO 140 and small-molecule CCR5 antagonists were more potently synergistic when used together rather than in combination with inhibitors that block other stages of HIV-1 entry. In contrast, additive effects were observed for combinations of two small-molecule CCR5 antagonists. Competition binding studies revealed complex and non-reciprocal patterns of CCR5 binding by mAb and small-molecule CCR5 inhibitors, and suggest that the synergistic interactions occur at the level of receptor binding.

Robust synergy between mAb and small-molecule CCR5 inhibitors was observed in this study. Potent synergy was observed for both cell-cell and virus-cell fusion, and there was a good concordance of findings in these two well-established assay systems. Comparable levels of synergy were observed for PRO 140 in combination with each of 3 small-molecule CCR5 antagonists from unrelated chemical series. In addition, consistent synergy was observed for each of two well-characterized HIV-1 envelopes and two CCR5 target cells. Synergy increased with increasing levels of viral inhibition and translated into in vitro dose reductions of up to 14-fold. Viewed alternatively, this degree of synergy provides a corresponding increase in antiviral pressure at a given concentration of drugs, thereby improving viral suppression and potentially delaying the emergence of drug-resistant virus. This is supported by preliminary studies indicating the mAb and small-molecule CCR5 inhibitors possess complementary patterns of viral resistance (Kuhmann et al. 2004 and Marorsan et al. 2005). The present findings provide a rationale for clinical exploration of regimens that combine mAb and small-molecule CCR5 inhibitors.

Potent synergy was also observed for RANTES used in combination with either UK-427,857 or PRO 140. Endogenous levels of RANTES may afford some protection against HIV-1 disease progression during natural infection (Garzino-Demo et al. 1999; Lui et al. 1999), and therefore this finding of synergy has important and positive implications for CCR5-targeted therapies of HIV-1. Antiviral synergy between RANTES and PRO 140 is not surprising based on a prior observation that RANTES signaling is not blocked by antiviral concentrations of murine PRO 140 (PA14) (Olson et al. 1999). Synergy between RANTES and UK-427,857 is less easily explained given that UK-427,857 is a potent CCR5 antagonist. However, these findings are consistent with prior observations of synergy between the small-molecule CCR5 antagonist SCH-C and aminooxypentane-RANTES (AOP-RANTES) (Tremblay et al. 2002), a RANTES derivative that has been evaluated as a potential topical microbicide (Kawamura et al. 2000).

In contrast to the robust synergy observed between mAb and small-molecule CCR5 antagonists, additive effects were observed for combinations of small-molecule CCR5 antagonists. Lack of cooperativity is consistent with the view that these molecules compete for binding to a common pocket on CCR5 (Dragic et al. 2000; Nishikawa et al. 2005; Tsamis et al. 2003; Watson et al. 2005). The in vitro studies do not provide a basis for combining small-molecule CCR5 antagonists in the clinic based solely on inhibition of wild-type virus.

Similarly, potent synergy was not observed between PRO 140 and inhibitors of HIV-1 attachment (PRO 542 and BMS-378806), fusion (enfuvirtide), or reverse transcriptase (zidovudine and nevirapine), and these findings underscore the significance of the synergy observed for PRO 140 and small-molecule CCR5 antagonists. A number of prior studies have examined interactions between various small-molecule CCR5 antagonists (UK-427,857, SCH-C, TAK-220, TAK-652 and E913) and drugs from each of the existing HIV-1 treatment classes. Most (Tremblay et al. 2005 Antivir. Ther.; Tremblay et al. 2005 Antimicrob. Agents Chemother: Tremblay et al. 2002) but not all (Dorr et al. 2005; Maeda et al. 2001) studies have reported broad synergy between CCR5 inhibitors and the other HIV-1 treatment classes, and the divergent results may reflect differences in the compounds and methods used for antiviral testing as well as differences in the methods used for data analysis. When UK-427,857 was tested against 20 licensed antiretroviral agents, additive effects were observed in all but three cases, where modest synergy was reported (Dorr et al. 2005). This result is consistent with the present findings for combinations of PRO 140 and HIV-1 inhibitors that do not target CCR5.

Without intending to be bound by theory, synergy between anti-HIV-1 drugs may stem from a variety of mechanisms. In mixed virus cultures, one compound may inhibit virus resistant to a second compound (Johnson et al. 1991), and NRTI/NNRTI combinations may overcome specific RT-mediated resistance mechanisms (Basavapathruni et al. 2004; Borkow et al. 1999). Metabolic interactions between inhibitors may increase their effective intracellular drug concentrations (Molla et al. 2002), and synergistic entry inhibitors may disrupt interdependent steps in the entry cascade (Nagashima et al. 2001; Tremblay et al. 2000). The present study examined clonal viral envelopes rather than mixed populations, and the extracellular nature of the target argues against metabolic interactions. Multiple domains of gp120 contribute to CCR5 binding (Cormier et al. 2002), but it is unclear at present whether these interactions represent separate or discrete events during infection.

The present findings indicate that antiviral synergy between mAb and small-molecule CCR5 inhibitors may occur at the level of the receptor. As discussed above, mAbs and small molecules bind distinct loci on CCR5 (Dragic et al. 2000; Nishikawa et al. 2005; Tsamis et al. 2003; Olson et al. 1999; Watson et al. 2005). When pre-incubated with CCR5 cells in the present study, PRO 140 completely blocked subsequent binding of UK-427,857 to the receptor; although the PRO 140 concentrations were higher than those needed to block HIV-1 entry into the same cells. In contrast, pre-incubation of CCR5 cells with super-saturating concentrations of UK-427,857 or SCH-D reduced PRO 140 binding by 50% or less. As one possible explanation, PRO 140 could recognize CCR5 conformers that are not bound by UK-427,857 or SCH-D. Although cell-surface CCR5 exists in multiple conformations (Lee et al. 1999), it seems unlikely that the small-molecule antagonists could demonstrate potent antiviral activity while failing to bind a significant fraction of cell-surface CCR5. In this regard, it is important to note that a common cellular background (CEM.NKR-CCR5 cells) was used for competition binding and antiviral studies, and therefore the findings are not related to cell-specific differences in CCR5 expression.

Without intending to be bound by theory, another plausible explanation for the present findings is that PRO 140 is capable of forming a ternary complex with UK-427,857-bound CCR5, and this ternary complex provides an increased barrier to HIV-1 entry. Within the context of this model, PRO 140 may bind UK-427,857-bound CCR5 somewhat less efficiently than free CCR5, as evidenced by the modest reduction in PRO 140 binding in the presence of UK-427,857.

The combination index method is widely used to assess drug-drug interactions. In this method, cooperativity often is defined on the basis of empirical CI values (e.g., <0.9 for synergy and >1.1 for antagonism) irrespective of inter-assay variability. Statistical analyses are performed infrequently, and even more rarely are adjustments made for multiple comparisons. In the absence of such analyses, there is increased potential to overestimate the number of synergistic combinations.

A rigorous and conservative approach to identifying synergistic effects was employed. CI values were tested for statistical significance against the null hypothesis of additivity (CI=1). In addition, these studies determined 20-30 different CI values per experiment (Tables 13 and 14), as is common in synergy studies. In order to reduce the potential for spurious positive results, the significance level was reduced using the Bonferroni correction. A mock combination was also evaluated as a test of these methods for antiviral testing and data analysis. It was therefore concluded that numerous apparent synergies (CI<0.9) could not be distinguished from inter-assay variation based on the available data. However, despite the rigorous nature of these methods, PRO 140 and small-molecule inhibitors demonstrated significant synergy under every test condition, lending credence to this finding. Combinations with CI values that trended towards significance in the present survey could be explored in future studies. For example, data for the PRO 140/enfuvirtide combination suggested modest synergy that trended towards significance; thus this combination may also be useful for treating HIV-1 infection.

A growing body of data indicates that mAb and small-molecule CCR5 antagonists represent distinct subclasses of CCR5 inhibitors, and a number of important parallels can be drawn between NRTI and NNRTI on the one hand and between mAb and small-molecule CCR5 antagonists on the other. In each instance, there are distinct binding loci for the inhibitors on the target protein (reverse transcriptase or CCR5). One set of inhibitors (NNRTI or small-molecule CCR5 antagonists) acts via allosteric mechanisms, while the other set (NRTI or CCR5 mAbs) acts as a competitive inhibitor. Like NRTI and NNRTI, mAb and small-molecule CCR5 inhibitors are synergistic and possess complementary patterns of viral resistance in vitro in preliminary testing (Kuhmann et al. 2004; Marozsan et al. 2005). NRTI and NNRTI represent important and distinct treatment classes even though they target the same protein, and mAb and small-molecule CCR5 inhibitors similarly may offer distinct HIV-1 treatment modalities.

Part IV

Materials and Methods:

PRO 140 and small-molecule CCR5 antagonists were prepared and/or obtained as described herein above. The primary R5HIV-1 isolates JR-FL and Case C 1/85 (CC1/85) were passaged weekly in vitro on peripheral blood mononuclear cells (PBMCC) in the presence or absence of progressively increasing concentrations of PRO 140 or SCH-D, and viral cultures were examined for susceptibility to these and other CCR5 inhibitors. For susceptibility testing, viruses were cultured in vitro on stimulated PBMC. In the presence and absence of serially diluted drug, and the extent of viral replication was determined by p24 ELISA.

Results:

For both JR-FL and CC1/85, drug-resistant variants were generated in the presence of PRO 140 and SCH-D. At passage 12, the escape mutants were approximately 10- to 100-fold less susceptible to the drug used for selection. In each case, the escape mutants continued to require CCR5 for replication on PBMC. Complementary patterns of resistance were observed: SCH-D escape mutants were efficiently inhibited by PRO 140 and PRO 140 escape mutants were efficiently inhibited by SCH-D.

Discussion:

PRO 140 escape mutants continue to require CCR5 for entry and remain susceptible to small-molecule CCR5 antagonists. In addition, PRO 140 is active against viruses resistant to small-molecule CCR5 antagonists. These findings indicate that PRO 140 and small-molecule CCR5 antagonists may represent distinct subclasses of CCR5 inhibitors.

Part V

Phase 1b Clinical Trial Study:

A Phase 1b, double-blind, randomized, single-dose, dose-cohort escalation study was conducted in which PRO 140 or placebo control was administered intravenously to adult (male and female) HIV-infected subjects. The efficacy data collected during the study were changes in viral load and CD4 counts over time. The safety data collected during the study were serious adverse events (SAEs)/adverse events (AEs) and changes in laboratory parameters (hematology, chemistry), physical exam, viral tropism and ECGs over time. The exploratory data collected included PK, immunogenicity (anti-PRO 140 antibody production), RANTES, and CCR5 lymphocyte coating over time.

Subjects and Methods:

Study Design:

A randomized, double-blind, placebo-controlled, dose-ascending study was conducted to evaluate the tolerability, antiviral activity and PK of single IV doses of PRO 140 in HIV-infected adults. Subjects were ≥18 years of age with plasma HIV-1 RNA ≥5,000 copies/mL, R5-tropic HIV-1 only, $CD4^+$ cells ≥250/µL with no documented nadir ≤200/µL and no antiretroviral therapy for at least 3 months. Major exclusion criteria included pregnancy, history of AIDS-defining illness, the presence of X4-tropic HIV-1, and acute or symptomatic viral hepatitis within the prior 6 months. Eligible subjects were randomized 10:3 to receive a single IV infusion of PRO 140 or placebo in one of three ascending dose cohorts, and then followed for 58 days. PRO 140 is a humanized IgG4,κ form of the CCR5 mAb PA14. PRO 140 (10 mg/mL nominal concentration) and matched placebo were provided as sterile phosphate-buffered solutions, pH 7.2. PRO 140 concentrations and dose levels are nominal values based on a theoretical ultraviolet spectroscopy extinction coefficient. The actual concentrations and doses of PRO 140 are 10% lower.

Virological Analyses:

Plasma HIV-1 RNA levels were determined with the Cobas Amplicor HIV-1 Monitor Test (Version 1.5; Roche Diagnostics, Branchburg, N.J.). Samples <400 copies/mL were re-analyzed with the Ultrasensitive Monitor Method. Co-receptor tropism was determined at screening and Days 1, 8, 29 and 59 (Trofile™ assay, Monogram Biosciences, Inc., South San Francisco, Calif.). Viral susceptibility was determined on Days 1 and 59 with the Phenosense™ HIV Entry assay. Results obtained with CCR5⁺ target cells were reported as Fold Change or relative $EC_{50}$ ($rEC_{50}$), which was defined as ($EC_{50}$ test isolate)/($EC_{50}$ reference virus). $EC_{50}$ is the concentration required for 50% inhibition of viral replication and was determined by logistical fit of the inhibition data. Maximum percent inhibitions were determined from the plateaus of the inhibition curves. The reference virus was HIV-$1_{92HT594}$, a low-passage dual-tropic isolate. GeneSeq™ (Monogram Biosciences) was used to assess HIV-1 subtype and genotypic susceptibility to protease and reverse transcriptase inhibitors.

Safety Evaluations:

Evaluations of clinical subjects included physical examinations, 12-lead electrocardiograms, vital signs, concomintant medications, and adverse events reporting. Clinical laboratory tests evaluated serum chemistries, hematology and urinalysis.

Bioanalylcal and Pharmacokinetic Methods:

Serum concentrations of PRO 140 and of antibodies to PRO 140 were measured using validated enzyme-linked immunosorbent assays (ELISA). The assay for PRO 140 had a lower limit of quantification (LLOQ) of 80 ng/mL and utilized a mouse anti-idiotype MAb (Progenics Pharmaceuticals, Inc.) for capture, and a mouse anti-IgG4-Fc antibody linked to horseradish peroxidase (The Binding Site, San Diego, Calif.) for detection. Samples below the LLOQ were assigned a value of zero. PK metrics were estimated using non-compartmental methods. The area under the serum concentration-time curve from time zero to infinity (AUC) was calculated using the linear trapezoidal rule. The terminal serum half-life was calculated by regression of the terminal portion of the concentration-time curve. Anti-PRO 140 antibodies were detected by capture onto PRO 140-coated microtiter plates, followed by sequential addition of biotinylated PRO 140, streptavidin-conjugated horseradish peroxidase and substrate. Sera were tested at a 1:10 dilution initially, and positive samples were serially diluted for titer analysis.

Lymphocyte and RANTES Analyses:

CCR5⁺ and CD4⁺ lymphocytes were measured by flow cytometry. CCR5⁺ lymphocytes were analyzed using phycoerythin (PE)-labeled PRO 140, CTC5 (R&D Systems) and isotype-control antibodies. Unlabeled PRO 140 blocks CCR5 binding by PRO 140-PE but not CTC5-PE. Therefore, analyses with PRO 140-PE and CTC5-PE assess the level of coating and depletion of CCR5 lymphocytes, respectively. CTC5-PE data were used to determine the absolute number of circulating CCR5⁺ lymphocytes pre- and post-treatment. RANTES was measured in platelet-depleted plasma using a validated ELISA.

Statistical and Pharmacodynamic Analyses:

Statistical analyses were performed on $log_{10}$ transformed HIV-1 RNA data, and changes were calculated relative to baseline (Day 1 pre-dose). Treatment and placebo groups were compared using an analysis of variance (ANOVA) model. If the overall F test was found to be statistically significant, each treatment group was compared to placebo using pairwise 2-sided t-tests. In addition, 2-sided paired t-tests were used to evaluate changes from baseline in CCR5⁺ lymphocytes. Where necessary, end-of-study lymphocyte data were used in place of missing baseline data. WinNonLin 4.1 (Pharsight Corporation, Mountain View, Calif.) was used to fit antiviral and PK data to an $E_{max}$ model:

$$E = E_{max} \times AUC/(AUC + AUC_{50})$$

where E=change in HIV-1 RNA, $E_{max}$=the maximum predicted change in HIV-1 RNA, and $AUC_{50}$=the AUC required to achieve 50% of $E_{max}$. The $R^2$ values, residuals and standard errors of the best-fit parameters indicated that the goodness of fit was adequate. $AUC_\infty$ values for individual subjects were used in the model.

Clinical Trial Design and Study Results:

This multi-center, double-blind, randomized, placebo-controlled Phase 1b trial examined three single intravenous escalating doses of PRO 140: 0.5 mg/kg, 2.0 mg/kg and 5.0 mg/kg. The study was designed to assess the safety, tolerability, pharmacology and antiviral activity of PRO 140 through day 59 and was conducted at 10 sites in the United States. Thirty-nine HIV-infected individuals who had taken no antiretroviral therapy within the preceding three months and who had plasma HIV RNA levels (viral loads) greater than or equal to 5,000 copies/mL were enrolled to receive PRO 140 monotherapy or placebo. The HIV-infected individuals in the study had a CD4+ count of >250 cells/µg. The subjects comprised 31 males and 8 females, and their median age, CD4 counts and plasma HIV-1 RNA levels at baseline were 40.3 years, 484 cells/µL and 26,900 copies/mL, respectively Fifteen subjects reported prior use of antiretroviral therapy, and seven were co-infected with hepatitis C virus (HCV). All viruses were subtype B, and baseline genotypic resistance to existing drugs was limited to single-class resistance in two subjects in the 2 mg/kg group and a single subject in each of the other groups. The mean infusion time was 36 minutes, and all subjects completed the 58-day follow-up period. All patients were screened prior to the study for the presence of virus that utilizes only CCR5 as the entry coreceptor, i.e., CCR5-tropic virus. Of the 13 patients in each cohort, 10 patients received PRO 140 and three received placebo (10:3). A summary of the baseline characteristics of the patients in the study is presented in Table 15.

TABLE 15

| Characteristic | Placebo (n = 9) | 0.5 mg/kg (n = 10) | 2 mg/kg (n = 10) | 5 mg/kg (n = 10) | All Subjects (n = 39) |
|---|---|---|---|---|---|
| Subject Baseline Characteristics | | | | | |
| Age median (range) | 40.3 (23.8-50.2) | 37.1 (24.1-53.2) | 37.6 (23.2-51.5) | 42.8 (22.9-61.1) | 40.3 (22.9-61.1) |
| Gender (n) male/female | 8/1 | 10/0 | 8/2 | 5/5 | 31/8 |
| Race (n) black/white/other | 4/5/0 | 4/4/2 | 4/6/0 | 5/4/1 | 17/19/3 |
| Prior ARV therapy (n) | 3 | 6 | 3 | 3 | 15 |

TABLE 15-continued

Subject Baseline Characteristics

| Characteristic | Placebo (n = 9) | 0.5 mg/kg (n = 10) | 2 mg/kg (n = 10) | 5 mg/kg (n = 10) | All Subjects (n = 39) |
|---|---|---|---|---|---|
| HCV Seropositive | 1 | 1 | 3 | 2 | 7 |
| Weight, kg median (range) | 81.4 (57.3-101.7) | 81.0 (54.2-111.4) | 81.7 (55.9-142.9) | 73.4 (52.7-86.8) | 80.9 (52.7-142.9) |
| CD4, cells/μl median (range) | 439 (281-555) | 493 (443-762) | 438 (269-613) | 535 (303-853) | 484 (269-853) |
| $Log_{10}$ HIV RNA, copies/mL median (range) | 4.44 (3.98-5.61) | 4.45 (3.79-5.54) | 4.44 (3.89-4.94) | 4.37 (3.81-5.36) | 4.43 (3.79-5.61) |

Antiviral Effects:

The primary efficacy endpoint was the reduction in plasma HIV RNA level as measured by the Roche Amplicor™ Assay. The primary efficacy endpoint is the maximum change from baseline in viral load, defined as HIV-1 copies/ml, as measured by the Roche Amplicor™ Assay. In the Phase 1b study, dose-dependent, and highly statistically significant reductions in HIV-1 RNA were observed for the two highest doses tested. HIV-infected individuals who received 5.0 mg/kg of PRO 140 achieved an average maximum decrease of viral load of 1.83 $log_{10}$ (98.5%; P<0.0001), with individual reductions ranging up to 2.5 $log_{10}$ (99.7%) at the 2.0 mg/kg and 5.0 mg/kg dose levels. At nine days post-treatment, mean HIV RNA values nadired, and these same individuals achieved a mean viral load reduction of 1.70 $log_{10}$ (98%; P<0.0001). At this time, mean PRO 140 serum concentrations were 1.4 and 4.1 μg/ml in the 2.0 mg/kg and 5.0 mg/kg dose levels, respectively. In the 5.0 mg/kg cohort, mean viral load was suppressed by 1.0 $log_{10}$ (90%) within four days of dosing and persisted at or below the 1.0 $log_{10}$ level of reduction for two to three weeks in patients before returning to baseline at approximately 30 days. The response rate among the treatment groups (percentage of patients with a ≥1 $log_{10}$ decrease in HIV RNA at any time) increased with PRO 140 dose, reaching a maximum of 100% in the highest dose cohort (P<0.0001).

Mean HIV-1 RNA reductions of 0.39, 0.58, 1.20 (p=0.0002) and 1.83 $log_{10}$ (p<0.0001) were observed for the placebo, 0.5 mg/kg, 2 mg/kg and 5 mg/kg groups, respectively (Table 16). Individual reductions ranged to 2.5 $log_{10}$ (99.7%) in both the 2 mg/kg and 5 mg/kg groups. For subjects in the 5 mg/kg group, individual HIV-1 RNA nadirs were observed on or between Days 8 and 15. In univariate linear regressions analyses with the Bonferroni correction for multiple comparisons, no significant correlation was observed between the maximum viral load reduction and baseline HIV-1 RNA, CD4+ cell count, or CCR5+ cell count.

Figure 21:
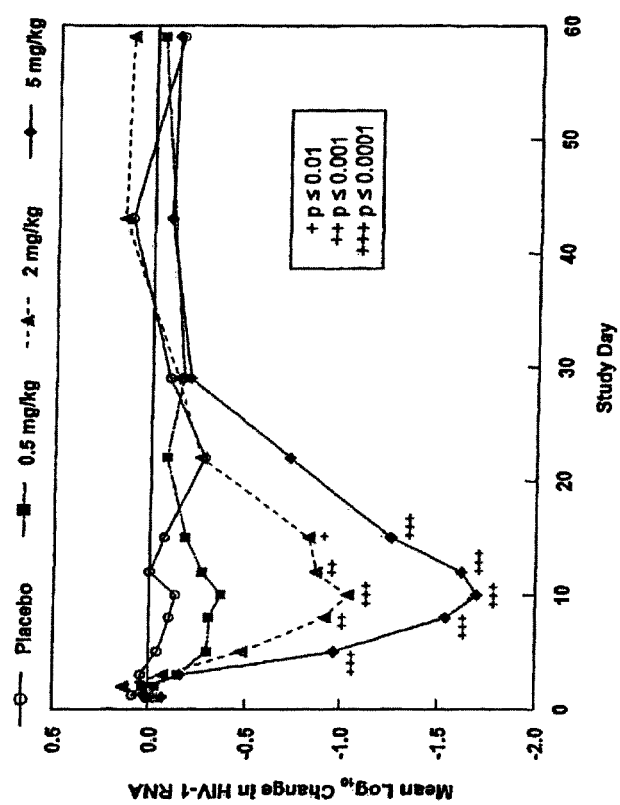
FIG. 21: Graph depicting mean $\log_{10}$ change from baseline in HIV-1 RNA for the different treatment groups in the Phase 1b study. P values are derived from ANOVA and reflect 2-sided t tests.

Antiviral effects exhibited a rapid onset and extended duration (FIG. 21). At 5 mg/kg, mean viral load reductions of 1 $log_{10}$ were first observed at Day 5 and then persisted until 2-3 weeks post-treatment. Viral load reductions were statistically significant at p≤0.0001 from Day 5 to Day 15 for the 5 mg/kg group and at p≤0.01 from Day 8 to Day 15 for the 2 mg/kg group. At Day 10, the mean $log_{10}$ declines in viral load were 0.13, 0.37, 1.04 (p=0.0001) and 1.70 (p<0.0001) for the placebo and ascending PRO 140 dose groups, respectively. For the placebo group, there was no significant change from baseline in HIV-1 RNA at any time post-treatment. (FIG. 21). Viral loads returned to baseline by Day 29 in all treatment groups.

Figure 22:
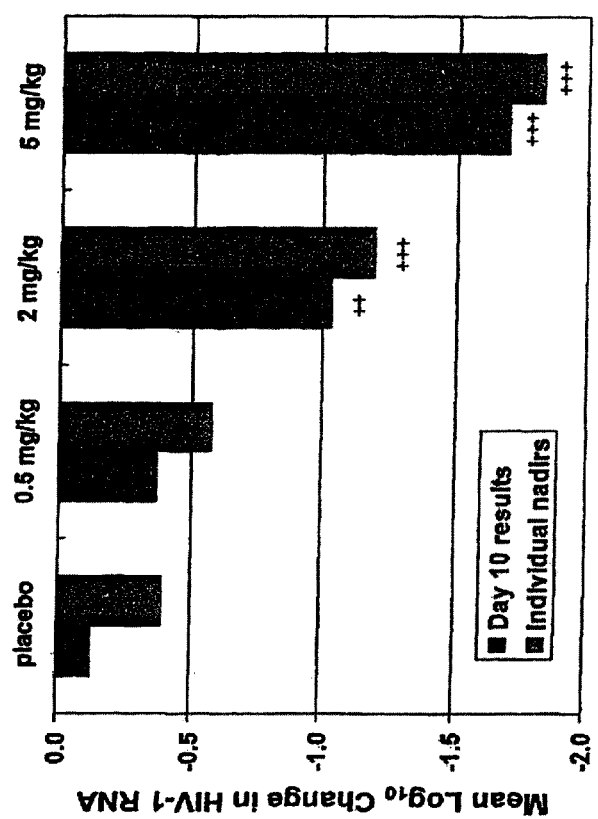
FIG. 22: Graph depicting mean $\log_{10}$ change in HIV RNA, day 10 results and individual subject nadirs.

Mean $log_{10}$ HIV RNA changes of −0.13, −0.37, −1.04 (P=0.0001) and −1.70 (P=0.0001) were observed at Day 10 post-treatment for the placebo, 0.5 mg/kg, 2.0 mg/kg and 5.0 mg/kg groups, respectively, as shown in FIG. 22; and a >10-fold decrease in HIV RNA was observed in 0/9, 1/10, 6/10 (P=0.01) and 10/10 (P=0.0001) individuals in these respective treatment groups. All PRO 140-treated individuals had exclusively R5 virus at pre-dose (baseline) and at end of study; there was no change in viral susceptibility to PRO 140 during the course of the study. Antiviral effects were evaluated as functions of PRO 140 serum levels, CCR5 receptor occupancy and viral susceptibility.

Antiviral response was defined as percent of subjects who achieved a ≥1.0 $log_{10}$ reduction in HIV-1 RNA at any time post-treatment. The antiviral response rate was 100% at 5 mg/kg (p<0.0001), 60% at 2 mg/kg (p=0.011), and 10% at 0.5 mg/kg. No placebo subject experienced a ≥1.0 $log_{10}$ reduction in HIV-1 RNA. The duration of response also increased with increasing dose (p=0.0059). Viral load was reduced to <400 copies/mL in four 5 mg/kg subjects and in one 2 mg/kg subject. The lowest documented HIV-1 RNA level on study was 61 copies/mL.

TABLE 16

Antiviral Effects of PRO 140

| $Log_{10}$ change from baseline in HIV-1 RNA | Placebo | 0.5 mg/kg | 2 mg/kg | 5 mg/kg |
|---|---|---|---|---|
| Mean (±SD) of individual nadirs | −0.39 ± 0.20 | −0.58 ± 0.30 | −1.20 ± 0.63 (p = 0.0002) | −1.84 ± 0.41 (p < 0.0001) |
| Mean (±SD) at Day 10 | −0.13 ± 024 | −0.37 ± 0.54 | −1.04 ± 0.45 (p = 0.0001) | −1.70 ± 0.49 (p < 0.0001) |
| Number of subjects (%) with ≥1 $log_{10}$ decrease in HIV RNA | 0/9 (0%) | 1/10 (10%) | 6/10 (60%) (p = 0.01) | 10/10 (100%) (p < 0.0001) |
| Number of subjects (%) with <400 copies HIV-1 RNA/mL | 0/9 (0%) | 0/10 (0%) | 1/10 (10%) | 4/10 (40%) |

SD = standard deviation

Lymphocyte and Chemokine Analyses:

Baseline CD4+ cells ranged from 269 to 853 cells/μL (Table 15). At 5 mg/kg PRO 140, there was a trend toward increased CD4+ cells over baseline. The mean changes were +129, +96 and +83 cells/μL at days Days 8, 15 and 22, respectively, and <+10 cells/μL at days Days 29 and 59. In contrast, the mean change in CD4+ cells ranged from −24 to +26 cells/μL in the placebo group. No significant change in CD4+ cells was observed for the 0.5 and 2 mg/kg groups.

Figure 27:
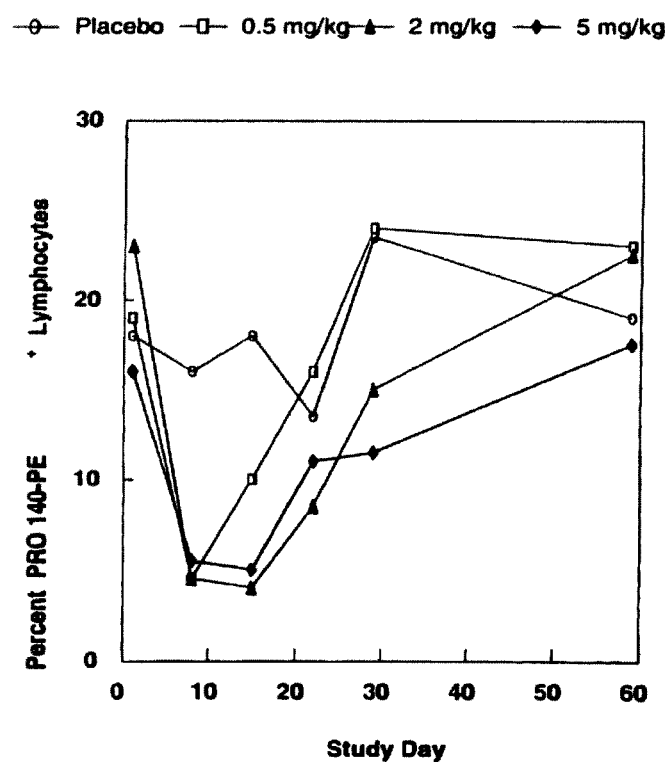
FIG. 27: Coating of CCR5 lymphocytes. Results of ex vivo flow cytometry analysis of lymphocytes using labeled PRO 140-PE. Blood samples were analyzed by flow cytometry using PRO 140-PE, and the median percentage of lymphocytes that stained positive is plotted by treatment group over time. CCR5$^+$ lymphocytes were not depleted from circulation following treatment. Therefore, decreased staining with PRO 140-PE reflects coating of CCR5 by the PRO 140 study drug.

Compared to CD4+ cells, CCR5+ cells showed greater intersubject variation. Pre-dose values ranged from 65 to 736 cells/μL, with a median of 296 cells/μL. There was no depletion of CCR5+ cells following treatment, and end-of-study values ranged from 64 to 1244 cells/μL, with a median of 348 cells/μL. Significant coating or masking of the PRO 140 epitope on CCR5+ lymphocytes was observed as a post-treatment reduction in ex vivo staining by fluorescently labeled PRO 140 (FIG. 27). Coating was maximal at Day 8 for all PRO 140 treatment groups and continued through Day 15 for the 2 mg/kg and 5 mg/kg groups. Coating was significant ($p<0.05$) for 2-4 weeks for all PRO 140 treatment groups; no significant CCR5 coating was observed for the placebo group ($p\geq0.18$ at all timepoints). Plasma RANTES levels varied from 2.5 to 24.2 ng/mL at baseline and were unaffected by treatment ($p\geq0.18$ for all dose levels and timepoints).

The conclusions that can be determined from the Phase 1b study are presented below:

PRO140 at single doses of 2.0 mg/kg and 5.0 mg/kg were effective in reducing viral load.

A dose response and an ineffective dose were identified.

Figure 19:
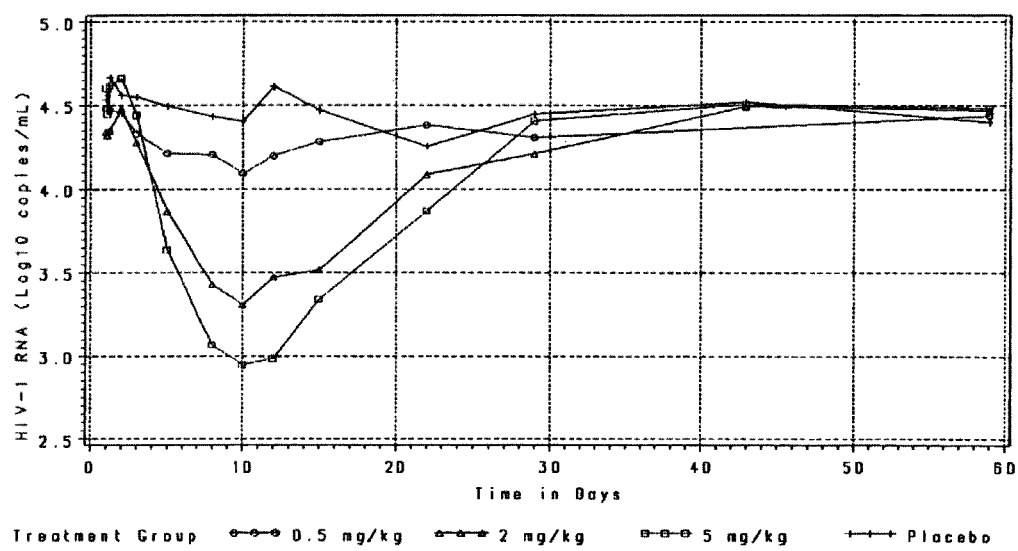
FIG. 19: Graph depicting change in viral load from baseline in Phase 1b Study.

PRO 140 5 mg/kg efficacy was dramatic, as evidenced by:

Maximum decrease of viral load at any time is −1.8 log, $p<0.0001$, as shown in FIGS. 19 and 21.

Viral load decrease was statistically significant by day 5, remained statistically significant through day 15 (day 22 was −0.73, $p=0.05^2$), nominal p values, as shown in FIG. 19.

Patients with >1 log decrease (anytime) 10/10 (100%), $p<0.0001$, as shown in FIG. 18.

AUC viral load is significantly decreased ($p=0.022$), as shown in FIG. 18.

Patients with <400 copies/mL (anytime) 4/10 (40%), $p=0.087$, as shown in FIG. 18.

Figure 20:
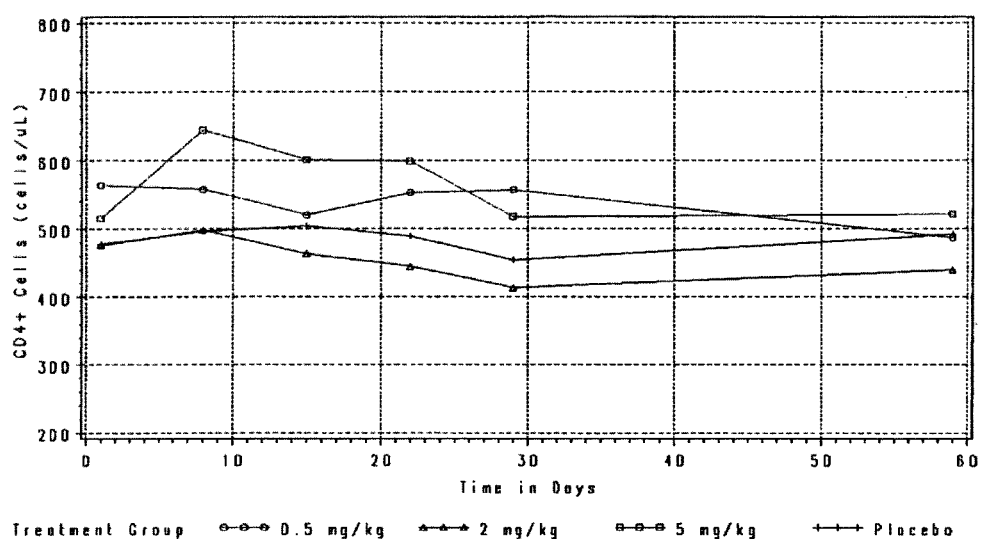
FIGS. 20A and 20B: Graphs depicting change in CD4+ cell counts in Phase 1b Study.
Figure 20:
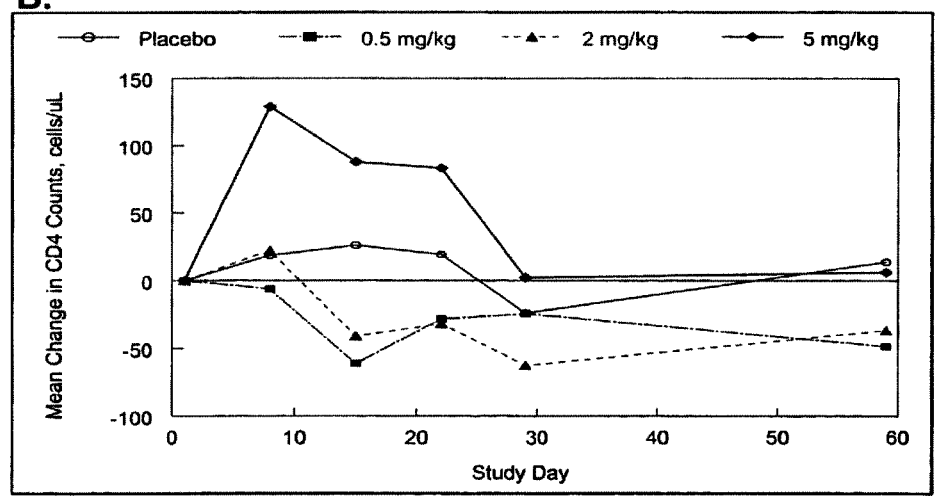

At 5 mg/kg, transient rise in and trend toward increased CD4+ lymphocytes (129 cells/mm$^3$ (29%) average increase at Day 8), $p=0.055$, nominal p values as shown as shown in FIGS. 20A and 20B. Levels remained elevated for 3 weeks post-treatment.

Safety

PRO 140 doses were generally well-tolerated in all study groups.

No treatment related SAEs and no apparent dose-related AEs were observed. With the exception of one individual in the 0.5 mg/kg group, all PRO 140 and placebo subjects reported at least one adverse event (AE). The most frequently reported AEs were headache in 12 subjects (31%), lymphadenopathy in 11 subjects (28%), and diarrhea and fatigue in 8 subjects (21%) each. No dose-proportional trend in the frequency of AEs was observed. The majority of events were judged by the investigator to be either not related or unlikely to be related to study medication. Shortly after infusion, one subject in the 5 mg/kg group experienced self-limiting symptoms (headache, fever, aches, nausea and emesis) similar to those commonly associated with IV infusion of immunoglobulins. No drug-related serious adverse events or dose-limiting toxicity was reported. There was no clinically relevant drug-related effect on QTc intervals or other electrocardiogram parameters. There were no remarkable findings in laboratory analyses for liver function, renal function, hematology, serum electrolytes or other parameters.

No change in plasma RANTES (CCL5) chemokine levels was observed.

No difference relative to placebo in HIV co-receptor tropism. No tropism shift (e.g., from CCR5 tropism to CXCR4 tropism) on treatment with PRO 140. All subjects screened for R5-only virus. Dual/mixed tropism result observed post-treatment in 1/9 placebo subjects (11%) and in 1/30 PRO 140 subjects (3%; 0.5 mg/kg group).

Immunogenicity

One patient in the 5 mg/kg cohort had a positive titer (1:40) for anti-PRO 140 antibody at day 59.

All other subjects in all cohorts tested negative.

Pharmacokinetics (PK)

Figure 26:
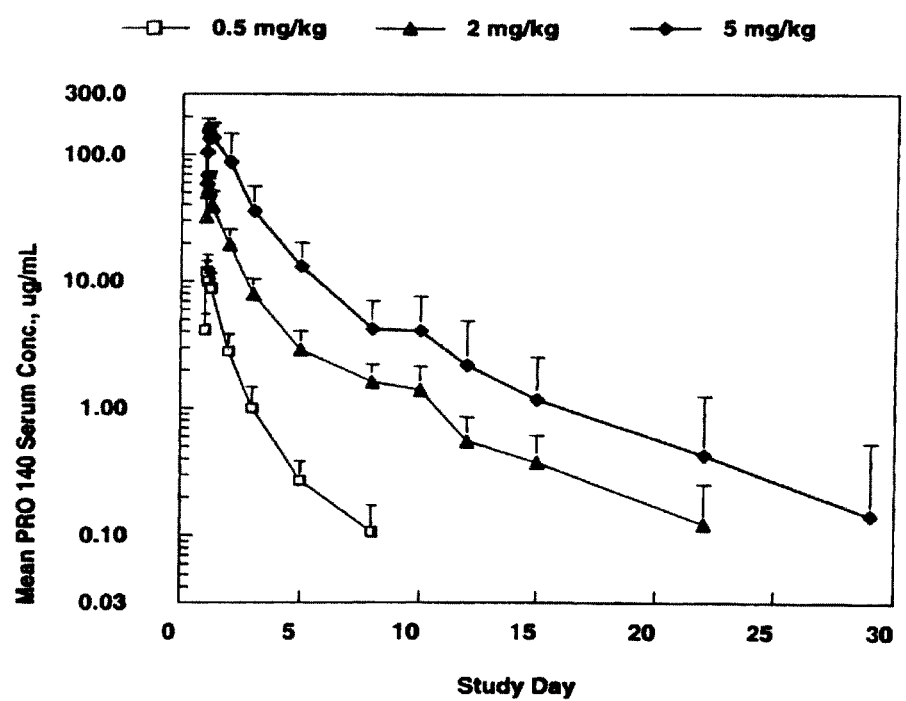
FIG. 26: Graph depicting the mean PRO 140 concentration (µg/mL) in serum over time by treatment group. The error bars depict standard deviations.

Mean serum concentrations of PRO 140 are illustrated in FIG. 26. Peak concentrations typically were observed 30 to 60 minutes post-infusion and averaged 13, 61 and 173 μg/mL for the ascending treatment groups. Concentrations [of PRO 140 in plasma] are 1% of Cmax by days 6-7. The mean time to last observation ($t_{last}$) was 6.1, 18.2 and 18.9 days for the 0.5, 2 and 5 mg/kg groups, respectively. The corresponding area under the PRO 140 concentration-time curve from time zero to infinity ($AUC_\infty$) values were 11.1, 74.3 and 278 mg×day/L, and these values are a ≤6% extrapolation of the AUC from time zero to $t_{last}$. Mean terminal half-lives were 3.9 and 3.5 days for the two highest dose groups. A smaller mean value (1.5 days) was observed in the low-dose group, perhaps due to insufficient data from the terminal phase. The rate of clearance decreased with increasing dose, and respective mean values were 4.1, 3.0 and 1.6 L/day. The volume of distribution exceeded the plasma volume and averaged 8.4, 13.8 and 7.1 L for the 0.5, 2 and 5 mg/kg dose groups, respectively. PK metrics were not significantly influenced by age, gender, body weight, or race. All tests for anti-PRO 140 antibodies were negative with the exception of a single low-titer (1:40) result at Day 59 for a 5 mg/kg subject. The antibodies had no obvious effect on PK metrics or antiviral response.

Coating of CCR5 Lymphocytes

Lymphocytes analyzed by flow cytometry ex vivo with fluorescently-labeled PRO 140 and non-competing CCR5 antibody.

No depletion of CCR5+ lymphocytes.

Obvious coating of CCR5 lymphocytes by PRO 140.

Duration of coating maximal for 1-2 weeks and consistent with duration of antiviral effects. (FIG. 27 and PART VI).

Virus Susceptibility

All viruses in PRO 140-treated subjects were susceptible to PRO 140 at baseline, with minimal variation. Mean rIC50=2.0 (range: 0.83-5.1). Mean Maximum Percent Inhibition (MPI)=99% (range: 93-100%).

Figure 25:
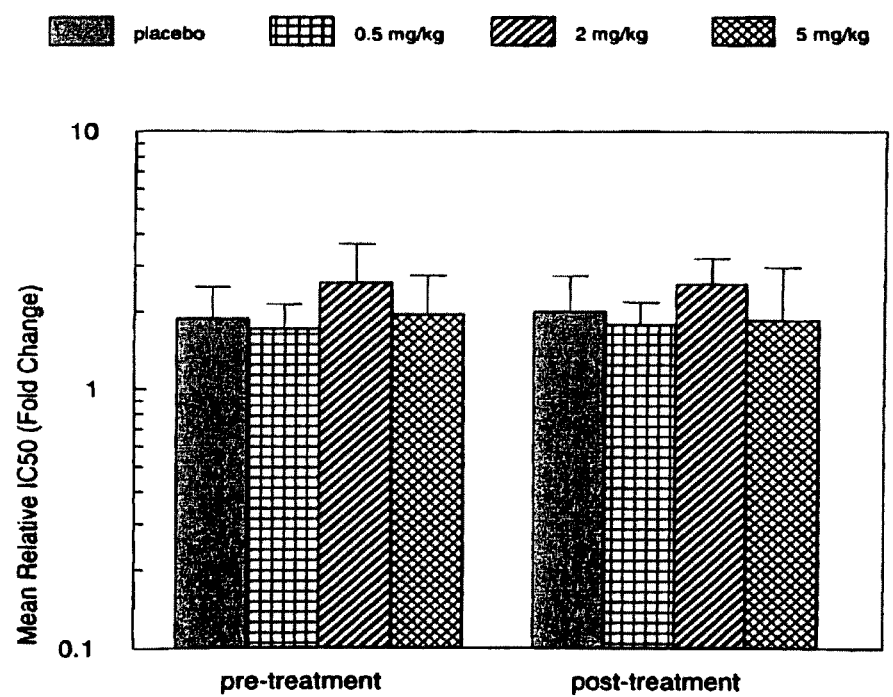
FIG. 25: Graph depicting virus susceptibility to PRO 140. All viruses in PRO 140-treated subjects were susceptible to PRO 140 at baseline with no change in virus susceptibility to PRO 140 post-treatment.

No change in susceptibility post-treatment. Less than 2-fold change in rIC50 for all subjects. Mean rIC50=2.1 (range: 0.98-4.71). Mean MPI=99% (range: 93-100%). (FIG. 25).

No change from baseline to day 59 in either the IC50 or the Fold Change of PRO 140 or Fuzeon, as determined by the PhenoSense™ Assay.

Correlates of Efficacy

PRO 140 dose was correlated with both the magnitude of HIV-1 RNA reduction (p=0.0001) and the duration of the response (p=0.0059).

Figure 28:
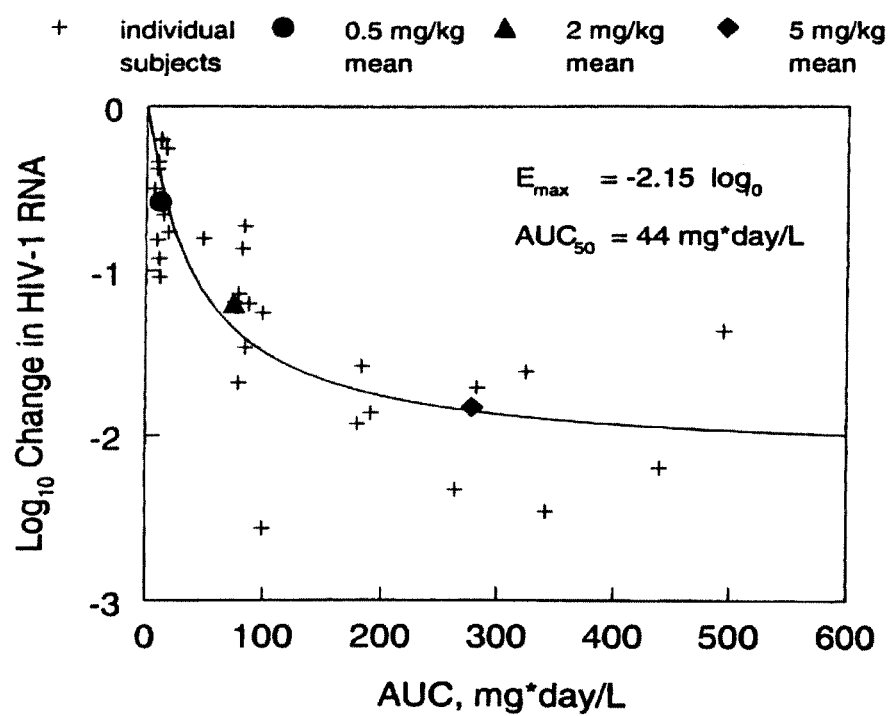
FIG. 28: Graph depicting correlate of efficacy ($E_{max}$ analysis). Maximum $\log_{10}$ change in HIV-1 RNA was plotted against $AUC_\infty$ for individual subjects, and data were fit to a Michaelis-Menton equation: $E=E_{max}\times AUC/(AUC+AUC_{50})$. The best-fit parameters are $-2.15\pm0.22$ $\log_{10}$ and $43.7\pm15.6$ mg×day/L. Mean data for the different treatment groups are plotted for illustration but were not used in the model.
Figure 29:
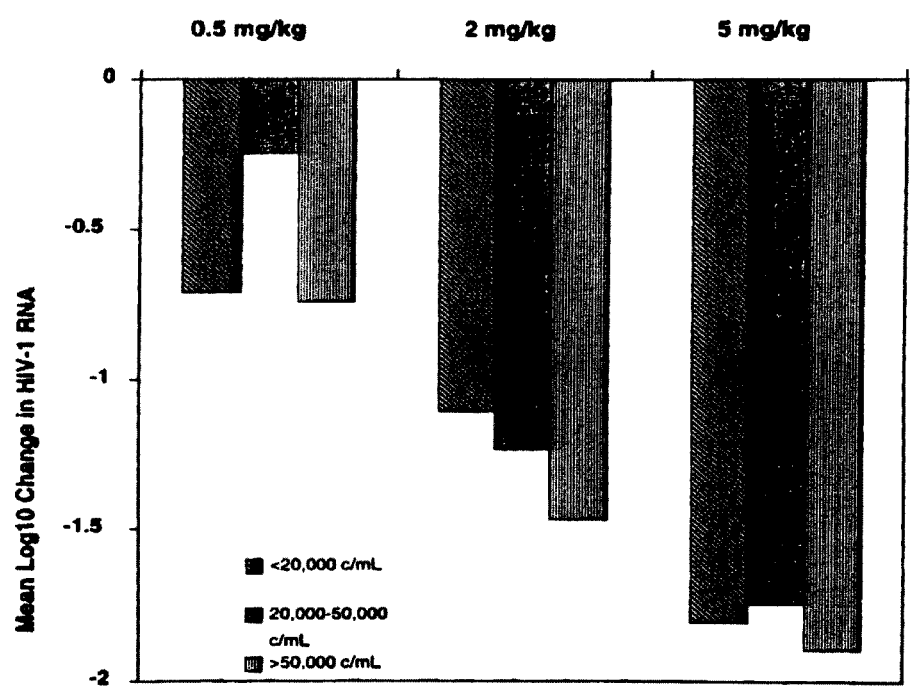
FIG. 29: Graph depicting correlate of efficacy. Mean $\text{Log}_{10}$ change in HIV-1 RNA. The results showed that HIV-1 RNA nadirs were not correlated with baseline HIV-1 RNA, baseline CD4+ cells, or baseline CCR5+ cells.

Correlation between HIV-1 RNA reduction and PRO 140 exposure ($E_{max}$ analysis). The relationship between antiviral response and PRO 140 exposure was examined using an $E_{max}$ model (FIG. 28). At saturation, the model predicted a 2.15±0.22 $\log_{10}$ decline in HIV-1 RNA for single-dose PRO 140. The exposure required to achieve 50% of this reduction was 43.7±15.6 mg×day/L.

HIV-1 RNA nadirs were independent of baseline HIV-1 RNA, baseline CD4+ cells and baseline CCR5+ cells. Accordingly, antiviral effects correlated with PRO 140 dose and exposure, but not with baseline HIV-1 RNA, CD4 cells, or CCR5 cells.

Preclinical studies support clinical use and feasibility of SC delivery

Safety and tolerability of SC administration in a six-month, preclinical animal model study.

Repeat SC dosing feasible.

Weekly and q2 weeks SC dosing expected to provide exposure similar to that of q2 weeks 5 mg/kg IV dose and may reduce differences in peak and trough concentrations.

Figure 23:
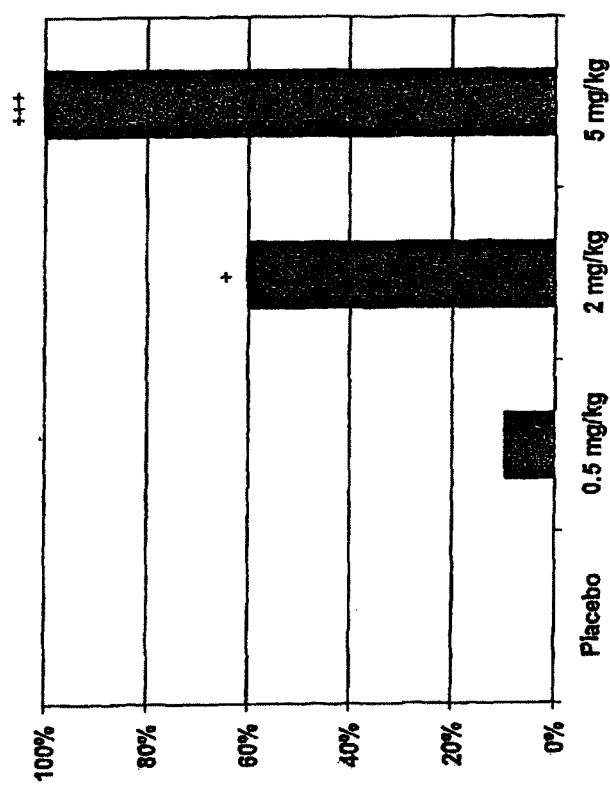
FIG. 23: Graph depicting virological response rate determined at the completion of the study. Percent of subjects in study cohorts with ≥1 $\log_{10}$ reduction in HIV-1 RNA.
Figure 24:
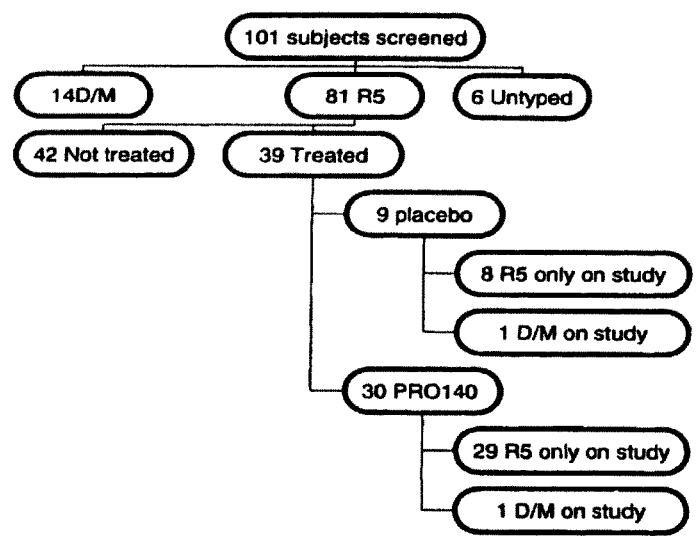
FIG. 24: Coreceptor virus tropism (Trofile™, Monogram Biosciences).

Co-Receptor Tropism and Viral Susceptibility to PRO 140:

The virological response rate was determined at the completion of the Phase 1b study, as shown in FIG. 23. Coreceptor tropism results (Trofile™, Monogram Biosciences) are shown in FIG. 24. One hundred and one individuals were screened for the study, and co-receptor tropism data were obtained for 95 individuals, of which 81 (85%) exhibited R5-only tropism and 14 (15%) had dual/mixed tropism results. R5-only tropism results were observed in all treated subjects at all times with two exceptions. One of the 9 placebo subjects (11%) had an R5-only tropism result at screening and dual/mixed tropism results thereafter. One of 30 PRO 140-treated subjects (3.3%; 0.5 mg/kg group) had a dual/mixed tropism result at Day 8, and R5-only results at all other times, including study end.

Clonal analyses were performed on the gp160 envelopes isolated from the one 0.5 mg/kg PRO 140-treated subject in whom a change from R5 to Dual/Mixed (DM) viral tropism was observed, to determine the likely source of CXCR4-using virus. Viruses isolated from the subject were analyzed for co-receptor tropism using Trofile™ at screening and at Days 1 (pre-treatment), 8, 15, 29 and 59 (study end). Multiple env clones were sequenced and analyzed for co-receptor tropism at baseline, Day 8 and Day 59. Sequence analysis was performed on nucleotide alignments of gp120, as well as full length gp160. Phylogenetic analysis was performed using PHYLIP 3.65. As a result of this analysis, DM virus was identified by Trofile™ at Day 8 only and was associated with a transient 0.66 $\log_{10}$ reduction in HIV-1 RNA. In clonal analyses, ~30% of Day 8 samples were DM. Phylogenetic analyses showed that most of the DM viruses from Day 8 were more closely related to baseline R5 viruses than to Day 8 R5 viruses. There was no difference in nonsynonymous/synonymous (dN/dS) ratio rates between R5 viruses at baseline and the DM day 8 viruses. Day 8 R5 viruses displayed different dN/dS rates from the baseline R5 viruses, suggesting a narrowing of the R5 virus population following treatment. The results of the phylogenetic analysis indicated that DM viruses were present at baseline. Therefore, the DM tropism result in the one individual reflects the outgrowth of pre-existing virus rather than mutation of an R5 virus to a DM virus following treatment with PRO 140.

In the study described in Part V, all pre-treatment viruses were susceptible to PRO 140. The relative $EC_{50}$ ($rEC_{50}$) values were 1.9±0.6, 1.7±0.4, 2.6±1.1 and 1.9±0.8 for the placebo and ascending PRO 140 dose groups, respectively. Baseline and end-of-study $rIC_{50}$ values were constant to within a factor of two for all subjects. Maximum percent inhibitions of 98.9±1.5% and 99.0±1.0% were observed at baseline and end-of-study, respectively. Overall, the in vitro analyses revealed no change in viral susceptibility following treatment.

Additionally, the study described in PART V demonstrates PRO 140 as a potent antiretroviral agent with prolonged activity following a single dose. The 1.83 $\log_{10}$ mean decrease in HIV-1 RNA resulting from treatment with PRO 140 is the largest mean decrease reported after a single dose of any HIV-1 drug. The antiviral data and favorable tolerability profile of PRO 140 serve to support the subcutaneous (SC) administration of PRO 140 as a potentially long-acting therapy for treating HIV-1 infection.

In accordance with the invention, there are fundamental differences in how PRO 140 and small-molecule CCR5 antagonsists recognize CCR5 and inhibit R5HIV-1. Without wishing to be bound by theory, PRO 140 binds hydrophilic extracellular regions on CCR5 and likely inhibits HIV-1 via competitive mechanisms, while small-molecule CCR5 antagonists bind a hydrophobic cavity and inhibit via allosteric mechanisms. Studies have shown that, relative to small-molecule CCR5 antagonists, PRO 140, or the parent murine PA14 monoclonal antibody, has demonstrated less potent inhibition of the natural activity of CCR5 in vitro. PRO 140, or the parent murine PA14 monoclonal antibody, has also shown limited viral cross-resistance relative to small molecule CCR5 antagonists. Additionally, relative to small-molecule CCR5 antagonists, studies have demonstrated that PRO 140 exhibits more potent antiviral synergy with diverse small molecule CCR5 antagonists in vitro. In many respects, these distinctions between PRO 140 and small-molecule CCR5 antagonists parallel the distinctions between nucleoside-analog and non-nucleoside reverse transcriptase inhibitors (NRTI and NNRTI).

PRO 140 bound CCR5 without depleting CCR5+ cells from the circulation. Masking or coating of CCR5 by PRO 140 was maximal for 1 week at the 0.5 mg/kg dose and for 2 weeks at the higher dose levels. These kinetics were broadly consistent with the timing of antiviral effects. In addition, there was a coincident trend toward increased numbers of CD4+ cells in the 5 mg/kg group. This finding may reflect redistribution of these cells from tissues to the periphery, which often accompanies potent antiviral suppression. However, regardless of mechanism, the trend is encouraging given that CD4+ cells are an established surrogate marker for monitoring the course of HIV-1 therapy.

The clearance of PRO 140 was similar to that reported for CCR5 mAb004, a human IgG4 mAb to CCR5 that also has been tested in HIV-infected individuals. However, both mAbs were cleared more rapidly than total IgG4. The PK metrics of PRO 140 are consistent with a saturable, antigen-mediated, clearance pathway. CCR5 internalizes constitutively in vitro, and internalizing antigens are known to accelerate clearance of cognate mAbs in vivo. While there was no obvious correlation between PRO 140 clearance and baseline CCR5+ cells, the flow cytometry assay assesses only circulating CCR5+ cells, which may not reflect the potentially greater reservoir of tissue-resident CCR5+ cells in the body. PRO 140's antiviral effects were also independent of baseline HIV-1 RNA and circulating CD4 cells.

The findings also support the subcutaneous (SC) delivery of PRO 140. SC mAb products include adalimumab (Humira™, Abbott Laboratories), omalizumab (Xolair™, Genentech and Novartis), and efalizumab (Raptiva™, Genentech). These mAbs are administered weekly to monthly either chronically or on a 12-week cycle at doses ranging to 375 mg. PRO 140 has shown favorable SC tolerability and bioavailability in preclinical studies, and SC dosing every 1 or 2 weeks has the potential to provide appropriate drug exposure.

Toxicities have been reported for all existing HIV-1 drugs and are among the leading causes for switching, discontinuing and non-adherence to therapy. Events such as hepatotoxicity, postural hypotension, QTc prolongation and possible malignancy, which have been reported for small-molecule CCR5 antagonists, have not been observed as safety concern signals in studies employing PRO 140. Favorable tolerability, infrequent dosing and potent antiviral activity are factors that are likely to enhance adherence to therapy.

Recent clinical trials of entry, integrase and newer protease inhibitors have demonstrated that complete viral suppression (<50 copies/mL) is possible for many patients with multidrug-resistant virus. However, incomplete viral suppression was noted in a majority or sizeable minority of treated subjects within 24-48 weeks of initiating treatment with the new agent and an optimized background regimen. Outcomes were markedly improved when 2 or more active agents were present in the regimen, and current guidelines recommend that subjects remain on a failing regimen until 2 or more active agents are available. Clearly, new agents and treatment classes are required to better manage the care of treatment-experienced individuals.

Results of the present study support a new standard for single-dose efficacy of HIV-1 drugs. As supported by the studies described herein, PRO 140 has been shown to be a potent, long-acting monoclonal antibody with a favorable tolerability profile and limited potential drug-drug or food interactions. Based on the study findings, PRO 140 could provide a new approach for HIV-1 therapy.

Part VI

This example describes the interplay between virological and immunological parameters following treatment with PRO 140. As discussed in PART V, PRO 140 demonstrated dose-dependent, highly significant antiviral effects that were both potent and prolonged in the Phase 1b study.
Methods:

Subjects were treated with single infusions of placebo or PRO 140 at doses of 0.5 mg/kg, 2 mg/kg, or 5 mg/kg and were monitored for 58 days. Plasma HIV-1 RNA, viral susceptibility to PRO 140 and enfuvirtide, CD4+ and CCR5+ lymphocytes and plasma RANTES levels were measured pre- and post-treatment by Amplicor, PhenoSense™ HIV Entry, flow cytometry and ELISA assays, respectively. Drug susceptibility was reported as relative IC50 values (rIC50), which equaled the IC50 observed for the test isolate divided by the IC50 for a reference virus tested in parallel.
Results and Conclusion:

HIV-1 RNA reductions averaged 0.39, 0.58, 1.20 and 1.83 $\log_{10}$ for the placebo and ascending PRO 140 treatment groups, respectively. Similarly, the duration of the antiviral response increased with dose (p=0.0059). Median HIV-1 RNA and CD4+ lymphocyte levels were 26,900 (range: 6,200-40,700) copies/mL and 484 (range: 269-853) cells/μL (Table 15), respectively, at baseline, and there was a trend (p=0.55) toward increased CD4+ cells following treatment with the 5 mg/kg dose of PRO 140. Baseline CCR5+ lymphocyte values demonstrated considerable inter-subject variation (range: 65-736 cells/μL); however, there was no obvious relationship between these values and antiviral responses to PRO 140. Similarly, baseline viral load had no impact on the antiviral response to PRO 140. High-level coating of CCR5 cells was observed for 2 weeks at the two highest dose levels of PRO 140, with kinetic properties consistent with the antiviral effects following administration of PRO 140. Across the 39 subjects, baseline rIC50 values for PRO 140 and enfuvirtide varied by 6.2-fold and 53-fold, respectively, and end-of-study analyses indicated no change in susceptibility to either agent. Plasma RANTES levels averaged 10.8 ng/ML at baseline and were unaffected by treatment.

Viral load reductions and high-level coating of CCR5+ lymphocytes exhibited similar durations of effect following treatment with single-dose PRO 140. Baseline CCR5+ cells showed greater inter-subject variation than CD4+ cells, but neither parameter significantly influenced antiviral responses. Similarly, antiviral responses were independent of the relatively modest variation in viral susceptibility to PRO 140 in vitro. Overall, these results contribute to defining determinants of the antiviral activity of PRO 140 in HIV-1 infected individuals.

Part VII

A phase 2 clinical study program involving PRO 140 for the treatment of HIV is designed to identify and evaluate both intravenous and subcutaneous formulations of PRO 140 in HIV-infected individuals with measurable levels of virus. The first two multi-center, randomized double-blind, placebo-controlled studies are conducted in volunteers with early-stage HIV disease who have not taken any antiretroviral therapy within the previous three months. A third study involves individuals who currently are on a failing currently available antiretroviral treatment regimens. Participants receive up to three doses of study medication, e.g., PRO 140, and are monitored for antiviral effects, safety, pharmacokinetics, immunogenicity and blood levels of PRO 140. For all studies, prospective participants are screened for the presence of CCR5-only tropic virus, i.e., R5-only HIV-1.

The initial phase 2 (e.g., 2a) trial assesses the feasibility of infrequent intravenous dosing intervals (e.g., monthly). A total of 30 patients are randomized into three groups (cohorts), ten patients per group, to be dosed with placebo, with PRO 140 at 5 mg/kg, or with PRO 140 at 10 mg/kg in an 8 week study. As described herein, a phase 1b dose-escalation study of intravenous PRO 140 in a similar patient population revealed that the magnitude and duration of antiviral effects increased with increasing dose. Based on this observation, the phase 2a program evaluates higher intravenous doses, potentially to extend the dose-response range and duration of antiviral activity.

Another phase 2 (e.g., 2a) trial evaluates subcutaneous delivery of PRO 140 on a weekly and biweekly basis. A total of 40 patients are randomized into four groups to receive placebo weekly, PRO 140 at 162 mg weekly, or PRO 140 at 324 mg, either weekly or bi-weekly for 8 weeks. More particularly, dosing comprises 162 mg q1wx3, 324 mg q1wx3, 324 mg q2wx2. Subcutaneous PRO 140 offers a long-acting, self-administered therapy for HIV infection.

A third phase 2 (e.g., 2a) study evaluates the tolerability, pharmacokinetics and antiviral activity of intravenous and subcutaneous forms of PRO 140 in individuals who have failed treatment with existing HIV-1 drugs.

Results

Less frequent dosing for HIV infective may improve compliance over current daily regimens. PRO 140, a humanized CCR5 monoclonal antibody, demonstrates potent, extended activity following a single intravenous dose. Here a subcutaneous (sc) regimen, suitable for self administration, is evaluated. A phase 2 trial was conducted on 44 infected individuals. The results show PRO 140 demonstrated positive clinical activity, a favorable tolerability profile and the potential for the convenience of weekly self administration Methods:

In the phase 2 trial of subcutaneous PRO 140, a total of 44 HIV-infected individuals who were treatment naïve or had discontinued therapy for at least three months were randomized to receive three weekly doses of 162 mg PRO 140, two bi-weekly (every-other week) doses of 324 mg PRO 140, three weekly doses of 324 mg PRO 140, or placebo. Subjects were followed for a total of 58 days for safety and antiviral effects. Entry criteria included: HIV-1 RNA >5,000 copies/mL, R5 virus, CD4>300/µL, no antiretroviral therapy <12 weeks. Subjects (n=44) randomized to one of four groups: (1) placebo: Days 1, 8, 15; (2) PRO 140 162 mg: Days 1, 8, 15; (3) 324 mg: Days 1, 15; (4) 324 mg: Days 1, 8, 15.

Results:

Baseline HIV-1 RNA values and CD4 counts are similar for the 4 groups. Changes in HIV-1 RNA from baseline after initiation of treatment are shown in Table 17.

In this study, for the 324 mg weekly dose group, a 1.65 log 10 mean maximum reduction in viral load ($p<0.0001$) was observed, with a 1.51 log 10 mean reduction in viral load ($p<0.0001$) observed at day 22. For the 324 mg dose tested on a bi-weekly basis, a 1.37 log 10 mean maximum reduction in viral load ($p=0.0001$) was observed, with a 1.20 log 10 mean reduction in viral load ($p=0.0001$) observed at day 22. For the 162 mg weekly dose group, a 0.99 log 10 mean maximum reduction in viral load ($p=0.0093$) was observed, with a 0.75 log 10 mean reduction in viral load ($p=0.0072$) observed at day 22.

TABLE 17

|  | Placebo<br>N = 10 | PRO 140 | | |
|---|---|---|---|---|
|  |  | 162 mg<br>Days 1, 8, 15<br>N = 11 | 324 mg<br>Days 1, 15<br>N = 12 | 324 mg<br>Days 1, 8, 15<br>N = 11 |
| Max viral load reduction ($\log_{10}$) | 0.2 | 0.99 | 1.37 | 1.65 |
| Range | 0.28 to −0.71 | −0.23 to −1.92 | −0.35 to −3.53 | −0.76 to −2.50 |
| p value (vs placebo) |  | .0093 | .0001 | <.0001 |
| % subjects with ≥1 $\log_{10}$ drop | 0 | 55 | 67 | 73 |
| Mean duration in days ≥1 $\log_{10}$ drop | 0 | 14 | 18 | 20 |

Subcutaneous PRO 140 was generally well tolerated compared to placebo. Administration site reactions for subcutaneous dosing, reported in a minority of subjects, were mild in intensity and resolved within one to two days. There were no drug-related serious adverse events. There was no apparent dose-limiting toxicity, nor any pattern of toxicity related to the various dosing forms.

Figure 30:
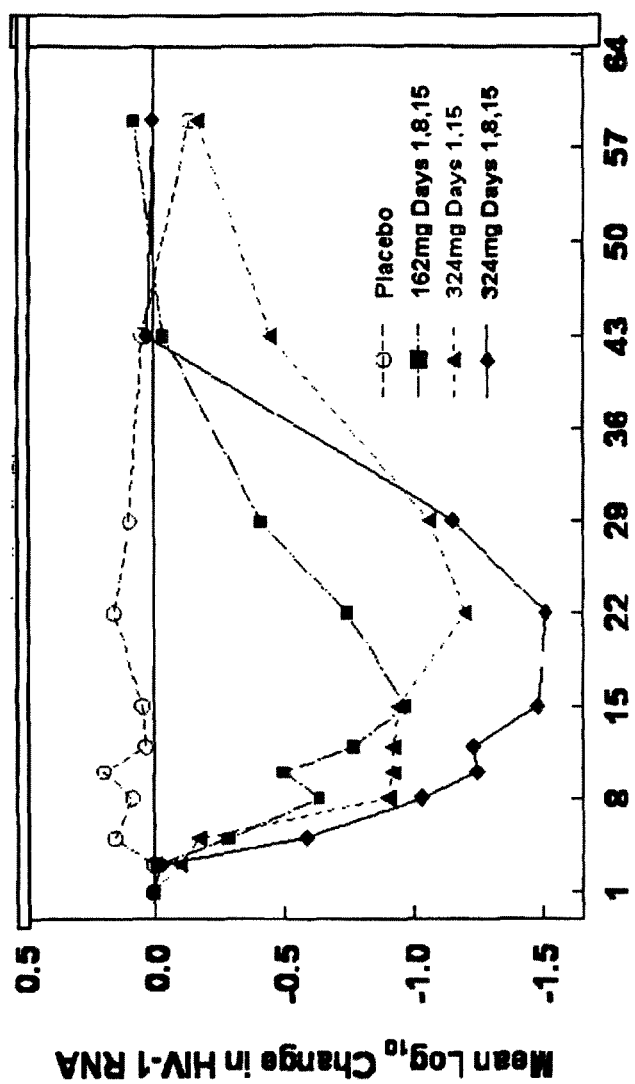
FIG. 30: Mean change in viral load over time (days) for HIV-infected individuals receiving multiple doses of subcutaneous PRO 140. 162 mg dose of PRO 140 given subcutaneously on days 1, 8 and 15. 324 mg dose of PRO 140 given subcutaneously on days 1 and 15, or on days 1, 8 and 15.
Figure 31:
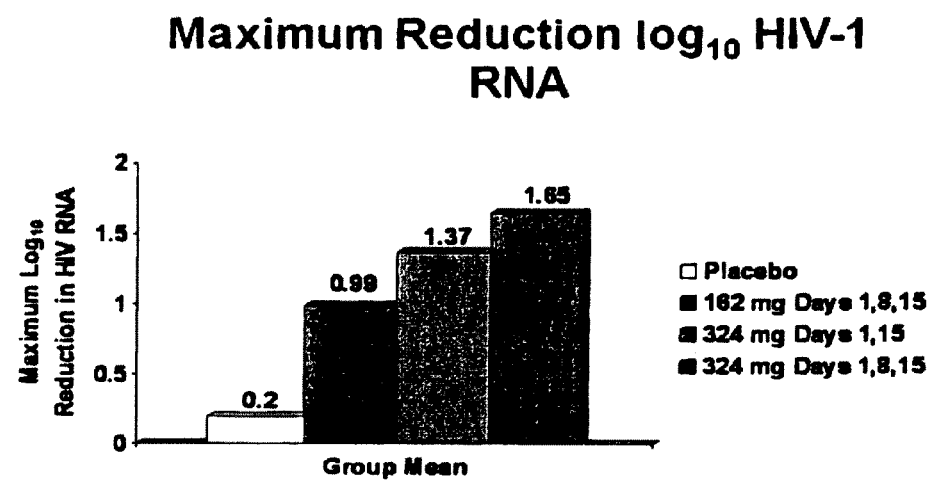
FIG. 31: The maximum $\log_{10}$ reduction in HIV-1 RNA in tested subjects. In the placebo group, N=10; in the 162 mg, Days 1, 8 and 15 group, N=11 (p=0.0093 compared to placebo); in the 324 mg, Days 1, 15 group, N=12 (p≤0.0001 compared to placebo); and in the 324 mg. Days 1, 8, 15 group, N=11 (p≤0.0001 compared to placebo).
Figure 32:
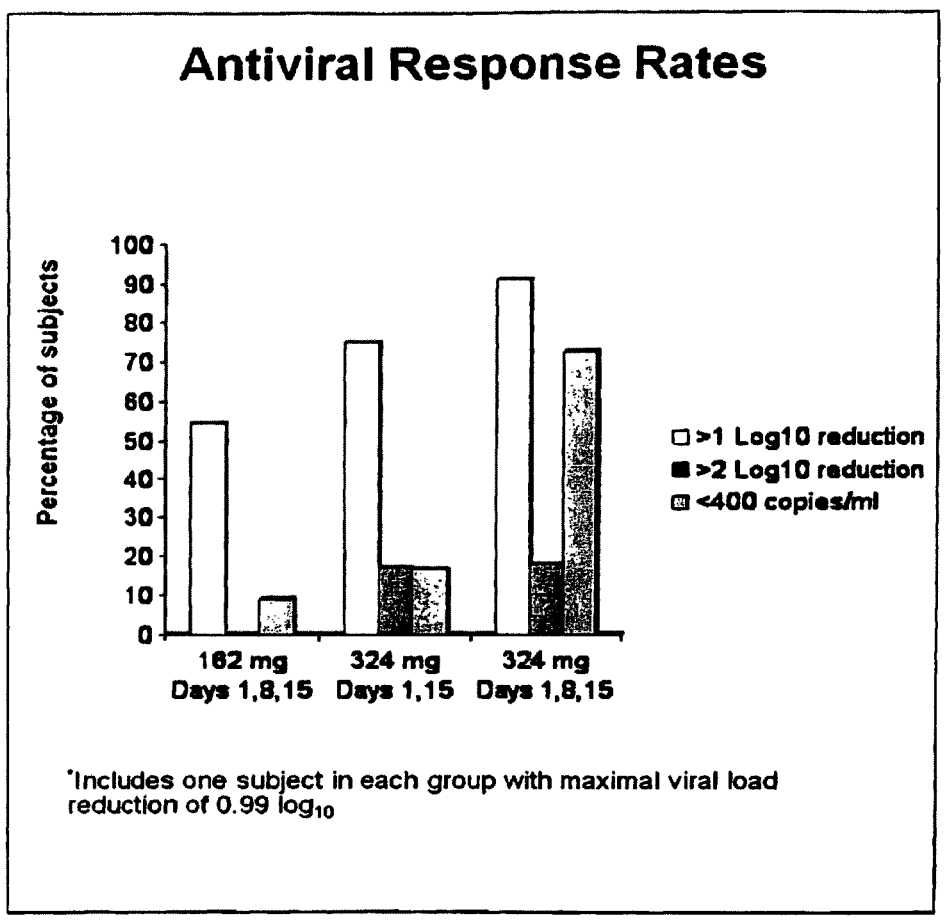
FIG. 32: The percentage of subjects responding with different $\log_{10}$ reductions of HIV-1 RNA. In the 162 mg, Days 1, 8 and 15 group, N=11; in the 324 mg, Days 1, 15 group, N=12; and in the 324 mg, Days 1, 8, 15 group, N=1.

FIG. 30 depicts the mean change in viral load over time (days) for the four dose groups. For all PRO 140 dose groups, the mean viral load decreased with each successive treatment, indicating sustained viral suppression by PRO 140. FIG. 31 shows the maximum reduction Log 10 HIV-1 RNA, and FIG. 32 shows the percentage of subjects with different Log 10 reductions of HIV-1 RNA.

As seen in Table 18, baseline $\log_{10}$ HIV-1 RNA values and CD4 counts in patients receiving subcutaneous doses of PRO 140 ranged from 3.61 to 6.68 and from 307 to 911/µL, respectively.

TABLE 18

| Characteristic | Placebo<br>(n = 10) | 162 mg<br>Days 1, 8, 15<br>(n = 11) | 324 mg<br>Days 1, 15<br>(n = 12) | 324 mg<br>Days 1, 8, 15<br>(n = 11) | Totals<br>(n = 44) |
|---|---|---|---|---|---|
| Age, median (range) | 44.9<br>(32.3-51.6) | 40<br>(29.1-44.6) | 45.9<br>(31.0-59.6) | 41.1<br>(34.8-53.6) | 42.3<br>(29.1-59.6) |
| Gender (n), male/female | 9/1 | 10/1 | 11/1 | 10/1 | 40/4 |

TABLE 18-continued

| Characteristic | Placebo (n = 10) | 162 mg Days 1, 8, 15 (n = 11) | 324 mg Days 1, 15 (n = 12) | 324 mg Days 1, 8, 15 (n = 11) | Totals (n = 44) |
|---|---|---|---|---|---|
| Race (n), black/white | 3/7 | 5/6 | 5/7 | 4/7 | 17/27 |
| Weight, kg median (range) | 82.3 (59.4-107.0) | 77 (59.3-94.4) | 88.3 (58.9-102.0) | 69.0 (60.8-83.6) | 79.1 (58.9-107) |
| CD4, cells/mL median (range) | 409.5 (312-878) | 352 (307-611) | 493 (357-911) | 389 (341-638) | 409.5 (307-911) |
| $Log_{10}$ HIV-1 RNA, copies/mL median (range) | 4.09 (3.94-5.13) | 4.43 (3.92-4.97) | 4.60 (4.03-6.68) | 4.19 (3.61-4.77) | N/A |

Figure 33:
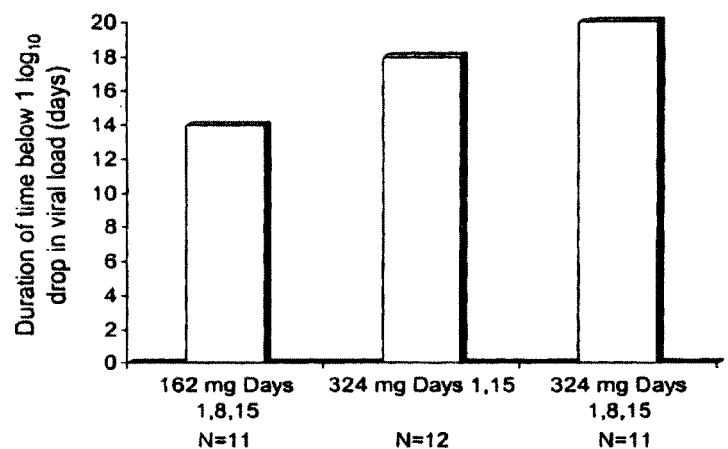
FIG. 33: The durability and extent of viral load drop in patients receiving subcutaneous doses of PRO 140.
Figure 34:
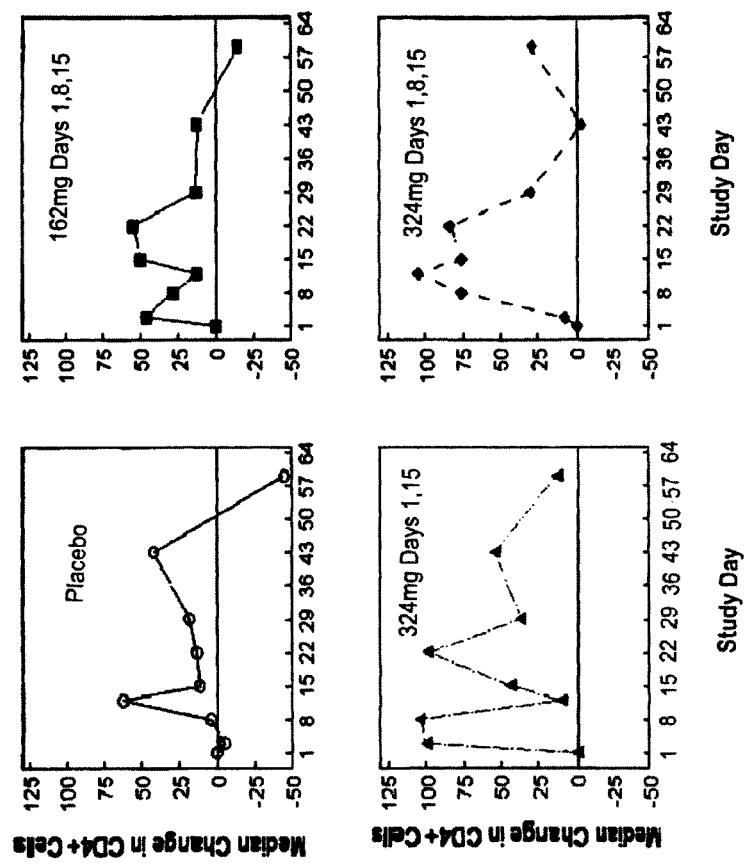
FIG. 34: Median change in CD4+ cells in patients receiving weekly or biweekly subcutaneous doses of PRO 140. In the placebo group, N=10; in the 162 mg, Days 1, 8 and 15 group, N=11 (p=0.0093 compared to placebo); in the 324 mg, Days 1, 15 group, N=12 (p≤0.0001 compared to placebo); and in the 324 mg, Days 1, 8, 15 group, N=11 (p≤0.0001 compared to placebo).

FIG. 33 shows the durability and extent of viral load drop in patients receiving subcutaneous doses of PRO 140. FIG. 34 presents the change in CD4+ cells in patients receiving placebo; patients receiving 162 mg of PRO 140 subcutaneously on days 1, 8 and 15; patients receiving 324 mg of PRO 140 subcutaneously on days 1 and 15; and patients receiving 324 mg of PRO 140 subcutaneously on days 1, 8 and 15. Table 19 presents maximum $log_{10}$ changes in HIV-1 RNA.

TABLE 19

| HIV-1 RNA | Placebo | 162 mg Days 1, 8, 15 | 324 mg Days 1, 15 | 324 mg Days 1, 8, 15 |
|---|---|---|---|---|
| Mean | −0.23 | −0.99 | −1.37 | −1.65 |
| Median | −0.17 | −1.06; p = 0.0093 | −1.16; p = 0.0001 | −1.74; p < 0.0001 |
| Day 22 Mean | 0.15 | −0.75 | −1.20 | −1.51 |
| Median | | −0.77; p = 0.0072 | −1.03; p < 0.0001 | −1.50; p < 0.0001 |

CONCLUSIONS

The results from the study show that PRO 140 demonstrated positive clinical activity, a favorable tolerability profile and suitability for the convenience of weekly self administration. In this study, subcutaneously (SC) administered PRO 140 demonstrated potent and highly significant antiviral effects at all doses examined. All doses were generally well tolerated, with SC PRO 140 demonstrating potent and prolonged antiretroviral activity without significant local or systemic toxicity. A mean maximum reduction in plasma levels of HIV RNA of 1.65 log 10 (98%) was observed following three weekly doses of 324 mg, the highest dose tested. Declines in HIV viral load were seen with all dosing regimens, with maximal reductions of 1.65 log 10 observed with 324 mg SC at days 1, 8 and 15. For the 324 mg SC dose of PRO 140 at days 1, 8 and 15, no significant viral rebound was observed between weekly dosing, and suppression continued for 7 days following the last dose. This finding is significant in view of the fact that, currently, all available HIV drugs are given between one and three times daily; therefore, a weekly administered therapy could have many advantages for compliance.

REFERENCES

U.S. Pat. No. 4,816,567, issued Mar. 28, 1989 to Cabilly et al.
U.S. Pat. No. 5,225,539, issued Jul. 6, 1993 to Gregory Winter.
U.S. Pat. No. 5,229,275, issued Jul. 20, 1993 to Goroff.
U.S. Pat. No. 5,545,806, issued Aug. 13, 1996 to Lonberg et al.
U.S. Pat. No. 5,545,807, issued Aug. 13, 1996 to Surani et al.
U.S. Pat. No. 5,565,332, issued Oct. 15, 1996 to Hoogenboom et al.
U.S. Pat. No. 5,567,610, issued Oct. 22, 1996 to Borrebaeck et al.
U.S. Pat. No. 5,585,089, issued Dec. 17, 1996 to Queen et al.
U.S. Pat. No. 5,591,669, issued Jan. 7, 1997 to Krimpenfort et al.
U.S. Pat. No. 5,693,761, issued Dec. 2, 1997 to Queen et al.
U.S. Pat. No. 6,150,584, issued Nov. 21, 2000 to Kucherlapati et al.
U.S. Pat. No. 6,476,034 B2, issued Nov. 5, 2002 to Wang et al.
U.S. Pat. No. 6,759,519 B2, issued Jul. 6, 2004 to Li et al.
PCT International Publication No. WO 90/07861, published Jul. 26, 1990.
PCT International Publication No. WO 00/35409, published Jun. 22, 2000.
PCT International Publication No. WO 01/55439, published Aug. 2, 2001.
PCT International Publication No. WO 01/90106 A2, published Nov. 29, 2001.
PCT International Publication No. WO 02/22077, published Mar. 21, 2002.
PCT International Publication No. WO 01/62255 A1, published Aug. 30, 2001.
PCT International Publication No. WO 03/082289 A1, published Oct. 9, 2003.
Alkhatib, G., et al. (1996) Science 272:1955.
Allaway, G. P., et al. (1993) AIDS Res. Hum. Retrovir. 9: 581-587.
Allaway, G. P., et al. (1995) AIDS Research and Human Retroviruses. 11: 533-539.
Baba, M., et al. (2005) 12th Conference on Retroviruses and Opportunistic Infections. Boston, Mass., Feb. 22-25, 2005, Abstract 541.
Baba, M., et al. (1999) Proc. Natl. Acad. Sci. USA 96: 5698-5703.
Balotta, C, P. et al. (1997) AIDS 11: F67-F71.

Basavapathruni, A., et al. (2004) J Biol. Chem. 279:6221-6224
Berger, E. A. (1997) AIDS 11 (Suppl A): S3-S16.
Bieniasz, P. D. and B. R. Cullen (1998) Frontiers in Bioscience 3: d44-58.
Biti, R., R. et al. (1997) Nature Med. 3: 252-253.
Borkow, G., et al. (1999) Antimicrob. Agents Chemother. 43:259-263
Burkly, L., et al. (1992) J. Immunol. 149: 1779-1787.
Burkly, L., et al. (1995) J. Virol. 69: 4267-4273.
Choe, H., et al. (1996) Cell 85: 1135-1148.
Chou, T. C. and D. C. Rideout (1991) Synergism and antagonism in chemotherapy. Academic Press, New York.
Chou, T. C. and P. Talalay (1984) Adv. Enzyme Regulation 22: 27-55.
Cocchi, F., et al. (1995) Science 270: 1811-1815.
Combadiere, C, et al. (1996) J. Leukocyte Biol. 60: 147-152.
Connor, R. I., et al. (1997) J. Exp. Med. 185: 621-628.
Cormier, E. G. and T. Dragic (2002) J. Virol. 76:8953-8957.
Cudeck, R. and L. L. O'Dell (1994) Psychol. Bull. 115:475-487.
Dalgleish, A. G., et al. (1984) Nature 312: 763-766.
Demarest, J., et al. (2004) 11th Conference on Retroviruses and Opportunistic Infections, Abstract 139. San Francisco, Calif., Feb. 8-11, 2004.
Deng, H., et al. (1996) Nature 381: 661-666.
Dorr, P., et al. (2003) 10th Conference on Retroviruses and Opportunistic Infections, Boston, Mass., Feb. 10-14, 2003, Paper #12.
Dorr, P., et al. (2005) Antimicrobial Agents and Chemotherapy 49:4721-4732.
Dragic, T., et al. (1997) Advances in Research and Therapy 7: 2-13.
Dragic, T., et al. (1992) J. Virol. 66: 4794-4802.
Dragic, T., et al. (1996) Nature 381: 667-673.
Dragic, T., et al. (2000) Proc Natl Acad Sci USA 97:5639-44.
Este J A. (2002) Curr. Opin. Investig. Drugs. 3: 379-383.
Falkenheuer, G., et al. (2005) Nat Med 11:1170-1172.
Feng, Y., et al. (1996) Science 272: 872-877.
Finke, P. E. et al. (2001) Bioorg. Med. Chem. Lett. 11: 2475-2479.
Garzino-Demo, A., et al. (1999) Proc Natl Acad Sci USA. 96:11986-11991.
Hale, J. J. et al. (2001) Bioorg. Med. Chem. Lett. 11: 2741-2745.
Hale, J J. et al. (2002) Bioorg. Med. Chem. Lett. 12: 2997-3000.
Hegde, V. R. et al. (2004) Bioorg. Med. Chem. Lett. 12: 5339-5342.
HGS Press Release (2004) Human Genome Sciences characterizes panel of novel human monoclonal antibodies that specifically antagonize the CCR5 receptor and block HIV-1 entry. Nov. 2, 2004.
HGS Press Release (2005) Human Genome Sciences begins dosing of patients in a phase 1 clinical trial of CCR5 mAb in patients infected with HIV-1. Mar. 30, 2005.
Huang, Y., et al. (1996) Nature Med. 2: 1240-1243.
Huffnagle, G. B., et al. (1999) Immunol. 163: 4642-4646.
Y. Iizawa, et al. (2003) 10th Conference on Retroviruses and Opportunistic Infections. Boston, Mass., Feb. 10-14, 2003
Imamura, S. et al. (2004a) Bioorg. Med. Chem. 12: 2295-2306.
Imamura, S. et al. (2004b) Chem. Pharm. Bull. (Tokyo) 52: 63-73.
Imamura, S. et al. (2005) Bioorg. Med. Chem. 13: 397-416.
Jayasuriya, H. et al. (2004) J. Nat. Prod. 67: 1036-1038.
Johnson, V. A., et al. (1991) Journal of Infectious Diseases 164:646-655.
Kawamura. T., et al. (2000) J Exp Med. 192:1491-1500.
Kuhmann, S. E., et al. (2004) J Virol 78:2790-2807.
Ketas, T J., et al. (2003) J. Virol. 77: 2762-2767.
Kim D. et al. (2001a) Bioorg. Med. Chem. Lett. 11: 3099-3102.
Kim D. et al. (2001b) Bioorg. Med. Chem. Lett. 11: 3103-3106.
Kim D. et al. (2005) Bioorg. Med. Chem. Lett. 15: 2129-2134.
Klatzmann, D., et al. (1984) Nature 312: 382-385.
Koyanagi, Y., et al. (1987) Science 236: 819-822.
Kuhmann, S. E. et al. (2004) J. Virol. 78: 2790-2807.
Kumar, S et al. (2003) J. Pharmacol. Exp. Ther. 304: 1161-1171.
Laal, S., et al. (1994) J. Virol. 68: 4001-4008.
Lalezari, J. P., et al. (2003) New Engl. J. of Med. 348: 2175-2185.
Lalezari, J., et al. (2004) 44th Annual Interscience Conference on Antimicrobial Agents and Chemotherapy, Abstract 2871, Washington, D.C., Oct. 30-Nov. 2, 2004.
Lalezari, J., et al. (2005) AIDS 19:1443-1448.
Lapidot, T. (2001) Ann. N.Y. Acad. Sci. 938: 83-95.
Lazzarin, A., et al. (2003) New Engl. J. Med. 348: 2186.
Lee, B., et al. (1999) Journal of Biological Chemistry 274:9617-9626.
Li, A., et al. (1997) AIDS Res. Hum. Retrovir. 13: 647-656.
Li, A., et al. (1998) J. Virol. 72: 3235-3240.
Lin, P. F., et al. (2003) Proc. Natl. Acad. Sci. USA 100: 11013-11018.
Lin, P. F., et al. (2002) 9th Conference on Retroviruses and Opportunistic Infections. Seattle, Wash., Feb. 24-28, 2002
Littman, D. R. (1998) Cell 93: 677-680.
Litwin, V., et al. (1996) J. Virol. 70: 6437-6441.
Liu, R., et al. (1996) Cell 86: 367-377.
Liu, H., et al. (1999) Proceedings of the National Academy of Sciences of the United States of America 96:4581-4585
Lynch, C. L. et al. (2003a) Bioorg. Med. Chem. Lett. 12: 3001-3004.
Lynch, C. L. et al. (2003b) Bioorg. Med. Chem. Lett. 13: 119-123.
Lynch, C. L. et al. (2002) Bioorg. Med. Chem. Lett. 12: 677-679.
Lynch, C. L. et al. (2003cOrg. Lett. 5: 2473-2475.
Maddon, P. J., et al. (1986) Cell 47: 333-348.
Maeda, K. et al. (2004) J. Virol. 78: 8654-8662.
Maeda, K. et al. (2001) J. Biol. Chem. 276: 35194-35200.
Marozsan, A J. et al. (2005) Virology 338: 182-199.
McCombie, S. W. et al. (2001) Bioorg. Med. Chem. Lett. 13: 567-571.
McDougal, J. S., et al. (1986) Science 231: 382-385.
Merluzzi, V J., et al. (1990) Science 250: 1411-1413.
Michael, N. L., et al. (1997) Nature Med. 3: 338-340.
Molla, A., et al. (2002) Antimicrob. Agents Chemother. 46:2249-2253.
Moore, J. P., Q J. Sattentau, P J. Klasse and L. C. Burkly (1992) J. Virol. 66: 4784-4793.
Nagashima, K. A., et al. (2001) J. Infect. Dis. 183: 1121-1125.
Nakata, H. et al. (2005) J. Virol. 79: 2087-2096.
Nishikawa, M., et al. (2005) Antimicrob. Agents Chemother. 49:4708-4715.
O'Brien, T. R., et al. (1997) Lancet 349: 1219.
Olson, W. C, et al. (1999) J. Virol. 73: 4145-4155.
Olson, W. C. and P. J. Maddon (2003) Current Drug Targets—Infectious Disorders 3:283-294.

Palani, A, et al. (2002) J. Med. Chem. 45: 3143-3160.
Palani, A, et al. (2001) J. Med. Chem. 44: 3339-3342.
Palani, A, et al. (2003a) Bioorg. Med. Chem. Lett. 13: 705-708.
Palani, A, et al. (2003b) Bioorg. Med. Chem. Lett. 13: 709-712.
Palella, F. J., et al. (1998) The New England Journal of Medicine 338:853.
Raport, C. J., et al. (1996) J. Leukocyte Biol. 59: 18-23.
Ray, N. and R. W. Doms (2006) Curt. Top. Microbiol. Immunol. 303:97-120.
Report of an FDA/FCHR Joint Public Meeting, May 31, 2006, Forum for Collaborative HIV Research, Apr. 24, 2007, Department of Prevention and Community Health, The George Washington University School of Public Health and Health Services, Written by J. Fry and J. B. Grossman; Ed. V. Miller.
Reyes, G. (2001) Development of CCR5 antagonists as a new class of anti-HTV therapeutic. 8th Conference on Retroviruses and Opportunistic Infections. Chicago, Ill., Feb. 5, 2001.
Reynes, J., et al. (2002) SCH C: Safety and antiviral effects of a CCR5 receptor antagonist in HIV-1 infected subjects. 9th Conference on Retroviruses and Opportunistic Infections. Seattle, Wash., Feb. 25, 2002
Robinson, B. S., et al. (2000) Antimicrob. Agents Chemother. 44: 2093-2099.
Roschke, V., et al. (2004) 44th Annual Interscience Conference on Antimicrobial Agents and Chemotherapy, Abstract 2871, Washington, D.C., Oct. 30-Nov. 2, 2004, Abstract #2871.
Samson, M., et al. (1997) J. Biol. Chem. 272: 24934-24941.
Schecter, A. D., et al. (2000) J. Biol. Chem. 275: 5466-5471.
Schols, D., et al. (1997) J. Ex. Med. 186: 1383-1388.
Schuh, J. M., et al. (2002) FASEB J. 16: 228-230.
Schurmann, D., et al. (2004) Abstract 140LB, San Francisco, Calif., Feb. 8-11, 2004.
Seibert, C., et al. (2006) Virology 349(1):41-54.
Seto, M. et al. (2005) Bioorg. Med. Chem. Lett. 13: 363-386.
Seto, M. et al. (2004a) Chem. Pharm. Bull. (Tokyo). 52: 818-829.
Seto, M. et al. (2004b) Chem. Pharm. Bull. (Tokyo). 52: 577-590.
Shah, S. K. et al. (2005) Bioorg. Med. Chem. Lett. 15: 977-982.
Shankaran, K. et al. (2004a) Bioorg. Med. Chem. Lett. 14: 3589-3593.
Shankaran, K. et al. (2004b) Bioorg. Med. Chem. Lett. 14: 3419-3424.
Shen, D. M. et al. (2004a) Bioorg. Med. Chem. Lett. 14: 935-939.
Shen, D. M. et al. (2004b) Bioorg. Med. Chem. Lett. 14: 941-945.
Shiraishi, M., et al. (2000) J. Med. Chem. 43: 2049-2063.
Shu, M. et al. (2004) Bioorg. Med. Chem. Lett. 14: 947-52.
Si, Z., et al. (2004) Proc. Natl. Acad. Sci. USA 101:5036-5041.
Simmons, G., et al. (1996) J. Virol. 70: 8355-8360.
Spenlehauer, C., et al. (2001) Virology 280:292-300.
Strizki, J. M. et al. (2001) Proc. Natl. Acad. Sci. USA. 98: 12718-12723.
Tagat, J. R. et al. (2001a) J. Med. Chem. 44: 3343-3346.
Tagat, J. R. et al. (2001b) Bioorg. Med. Chem. Lett. 11: 2143-2146.
Tagat, J. R., et al. (2004) J. Med. Chem. 47: 2405-2408.
Takashima, K., et al. (2005) Antimicrob. Agents Chemother. 49:374-3482.
Thali, M., et al. (1992) J. Acquir. Immune Defic. Syndr. 5: 591-599.
Thoma, G. et al. (2004) J. Med. Chem. 47: 1939-1955.
Tilley, S. A., et al. (1992) AIDS Res. Hum. Retrovir. 8: 461-467.
Tran, E. H., et al. (2000) Eur. J. Immunol. 30: 1410-1415.
Tremblay, C., et al. (2000) Journal of Acquired Immune Deficiency Syndromes and Human Retrovirology 25:99-102
Tremblay, C. L., et al. (2002) Antimicrobal Agents and Chemotherapy 46:1336-1339.
Tremblay, C. L., et al. (2005) 12th Conference on Retroviruses and Opportunistic Infections. Boston, Mass., Feb. 22-25, 2005, Abstract 542.
Tremblay, C. L., et al. (2005) Antivir. Ther. 10:967-968.
Tremblay, C. L., et al. (2005) Antimicrob. Agents Chemother. 49:3483-3485.
Trkola, A., et al. (2001) J. Virol. 75: 579-588.
Trkola, A., et al. (1999) Journal of Virology 73:8966-8974.
Trkola, A., et al. (1998) J. Virol. 72: 1876-1885.
Tsamis, F., et al. (2003) Journal of Virology 77:5201-5208.
Vijh-Warrier, S., et al. (1996) J. Virol. 70: 4466-4473.
Watson, C., et al. (2005) Mol. Pharmacol. 67:1268-1282.
Wild, C., et al. (1992) PNAS 89:10537-10541.
Willoughby, C. A. et al. (2001) Bioorg. Med. Chem. Lett. 11: 3137-41.
Willoughby, C. A. et al. (2003) Bioorg. Med. Chem. Lett. 13: 427-431.
Wu, L., et al. (1997) J. Exp. Med. 186: 1373-1381.
Zhou, Y., et al. (1998) J. Immunol. 160: 4018-4025.
Zhu, P. et al. (2001) J. Virol. 75: 6682-6686.

What is claimed is:

1. A CCR5 receptor antagonist formulation consisting of a therapeutically effective single subcutaneous dose of a humanized monoclonal antibody designated PRO 140, or a fragment thereof, in an amount 5 mg/kg of body weight for an HIV-infected subject, wherein said formulation results in suppression of HIV-1 viral replication.

2. The CCR5 receptor antagonist formulation of claim 1, wherein the PRO 140 comprises (i) two light chains, each light chain comprising the light chain variable ($V_L$) and constant ($C_L$) regions encoded by the plasmid designated pVK:HuPRO140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPR0140 HG2-VH (ATCC Deposit Designation PTA-4098) or by the plasmid designated pVg4:HuPR0140 (mut B+D+I)-VH (ATCC Deposit Designation PTA-4099), or a fragment thereof.

3. The CCR5 receptor antagonist formulation of claim 1, wherein the therapeutically effective dose is about 324 mg.

4. The CCR5 receptor antagonist formulation of claim 1, wherein the dose accounts for viral suppression for the HIV-infected subject for about seven days following the last dose.

5. The CCR5 receptor antagonist formulation of claim 1, wherein the dosing regimen accounts for viral suppression for the HIV-infected subject for at least two weeks.

6. A therapeutic composition comprising a therapeutically effective single subcutaneous or intravenous dose of a CCR5 receptor antagonist in an amount of 5 mg/kg for an HIV-infected subject that results in suppression of HIV-1 viral replication, wherein the CCR5 receptor antagonist is a humanized monoclonal antibody designated PRO 140 or a fragment thereof, or a conjugate of said CCR5 receptor antagonist.

7. The therapeutic composition of claim 6, wherein the CCR5 receptor antagonist comprises (a) a humanized monoclonal antibody designated PRO 140 which comprises (i) two light chains, each light chain comprising the light chain variable ($V_L$) and constant ($C_L$) regions encoded by the plasmid designated pVK:HuPR0140-VK (ATCC Deposit Designation PTA-4097), and (ii) two heavy chains, each heavy chain comprising the heavy chain variable ($V_H$) and constant ($C_H$) regions encoded either by the plasmid designated pVg4:HuPR0140 HG2-VH (ATCC Deposit Designation PTA-4098) or by the plasmid designated pVg4: HuPR0140 (mut B+D+I)-VH (ATCC Deposit Designation PTA-4099), or (b) a fragment thereof.

8. The CCR5 receptor antagonist formulation of claim 1, wherein the therapeutically effective single subcutaneous dose does not result in an administration site reaction lasting more than two days.

9. The CCR5 receptor antagonist formulation of claim 6, wherein the therapeutically effective single subcutaneous or intravenous dose does not result in an administration site reaction lasting more than two days.

10. The therapeutic composition of claim 6, wherein the prolonged viral suppression is characterized by about a 1.83 $\log_{10}$ decrease in HIV-1 RNA.

11. The CCR5 receptor antagonist formulation of claim 1, wherein the prolonged viral suppression is characterized by about a 1.83 $\log_{10}$ decrease in HIV-1 RNA.

12. A pharmaceutical composition comprising a CCR5 receptor antagonist subcutaneous formulation consisting of a therapeutically effective single subcutaneous dose of a humanized monoclonal antibody (mAb) designated PRO 140, or a fragment thereof, in an amount of 5 mg/kg of body weight for an HIV-1-infected subject, wherein said composition results in suppression of HIV-1 viral replication.

* * * * *